US009580384B2

(12) United States Patent
Furukawa et al.

(10) Patent No.: US 9,580,384 B2
(45) Date of Patent: Feb. 28, 2017

(54) ARYLOXYUREA COMPOUND AND PEST CONTROL AGENT

(71) Applicant: Nippon Soda Co., Ltd., Chiyoda-ku, Tokyo (JP)

(72) Inventors: Hironori Furukawa, Odawara (JP); Takehiko Nakamura, Shimada (JP); Tetsuo Tamai, Odawara (JP); Daisuke Hanai, Odawara (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 14/676,921

(22) Filed: Apr. 2, 2015

(65) Prior Publication Data

US 2015/0203448 A1    Jul. 23, 2015

Related U.S. Application Data

(63) Continuation of application No. 13/877,769, filed as application No. PCT/JP2011/073082 on Oct. 6, 2011, now Pat. No. 9,029,601.

(30) Foreign Application Priority Data

Oct. 12, 2010 (JP) ................................. 2010-229617

(51) Int. Cl.
*C07C 275/64* (2006.01)
*A61K 31/17* (2006.01)
(Continued)

(52) U.S. Cl.
CPC ............ *C07C 275/64* (2013.01); *A01N 47/28* (2013.01); *A01N 47/30* (2013.01); *A01N 47/32* (2013.01); *A01N 47/34* (2013.01); *A61K 31/17* (2013.01); *A61K 31/197* (2013.01); *A61K 31/216* (2013.01); *A61K 31/277* (2013.01); *A61K 31/341* (2013.01); *A61K 31/381* (2013.01); *A61K 31/41* (2013.01); *A61K 31/415* (2013.01); *A61K 31/4196* (2013.01); *A61K 31/42* (2013.01); *A61K 31/421* (2013.01); *A61K 31/426* (2013.01); *A61K 31/4245* (2013.01); *A61K 31/44* (2013.01); *A61K 31/4402* (2013.01); *A61K 31/4406* (2013.01); *A61K 31/4409* (2013.01); *A61K 31/4412* (2013.01); *A61K 31/4418* (2013.01); *A61K 31/4439* (2013.01); *A61K 31/4453* (2013.01); *A61K 31/47* (2013.01); *A61K 31/4709* (2013.01); *A61K 31/4725* (2013.01); *A61K 31/498* (2013.01); *A61K 31/4965* (2013.01); *A61K 31/50* (2013.01); *A61K 31/505* (2013.01); *A61K 31/506* (2013.01); *A61K 31/53* (2013.01); *C07C 271/40* (2013.01); *C07C 317/22* (2013.01); *C07C 381/10* (2013.01); *C07D 211/60* (2013.01); *C07D 213/30* (2013.01); *C07D 213/40* (2013.01); *C07D 213/54* (2013.01); *C07D 213/61* (2013.01); *C07D 213/62* (2013.01); *C07D 213/64* (2013.01); *C07D 213/74* (2013.01); *C07D 213/75* (2013.01); *C07D 213/79* (2013.01); *C07D 213/83* (2013.01); *C07D 213/84* (2013.01); *C07D 213/89* (2013.01); *C07D 215/20* (2013.01); *C07D 215/22* (2013.01); *C07D 217/22* (2013.01); *C07D 231/12* (2013.01); *C07D 237/08* (2013.01); *C07D 239/26* (2013.01); *C07D 241/12* (2013.01); *C07D 249/08* (2013.01); *C07D 253/06* (2013.01); *C07D 253/065* (2013.01); *C07D 257/04* (2013.01); *C07D 261/08* (2013.01); *C07D 263/10* (2013.01); *C07D 271/06* (2013.01); *C07D 277/28* (2013.01); *C07D 295/16* (2013.01); *C07D 295/192* (2013.01); *C07D 307/42* (2013.01); *C07D 307/52* (2013.01); *C07D 333/16* (2013.01); *C07D 333/20* (2013.01); *C07D 401/12* (2013.01); *C07D 417/12* (2013.01); *C07C 2101/02* (2013.01); *C07C 2101/08* (2013.01); *C07C 2101/14* (2013.01); *C07C 2101/16* (2013.01); *C07C 2102/08* (2013.01); *C07C 2102/10* (2013.01)

(58) Field of Classification Search
CPC .................................................... C07C 275/64
See application file for complete search history.

(56) References Cited

U.S. PATENT DOCUMENTS 8,268,755 B2    9/2012  Furukawa et al.
2011/0144374 A1  6/2011  Furukawa et al.

FOREIGN PATENT DOCUMENTS

EP    0 183 174 A2   6/1986
EP    0 270 683      6/1988
(Continued)

OTHER PUBLICATIONS

Supplementary European Search Report dated Jan. 27, 2014, in EP 11832476.3.
(Continued)

*Primary Examiner* — Paul A Zucker
*Assistant Examiner* — Mark Luderer
(74) *Attorney, Agent, or Firm* — Foley & Lardner LLP

(57) ABSTRACT

The present invention provides a pest control agent, acaricide or fungicide that contains, as the active ingredient thereof, at least one type of compound selected from the aryloxyurea compounds represented by formula (V) (wherein $R^1$ to $R^5$ each independently represents an alkyl group or the like, X is a halogen atom or the like, n is an integer of 0 to 5, and Z is an oxygen atom or sulfur atom) or salts thereof.

(Continued)

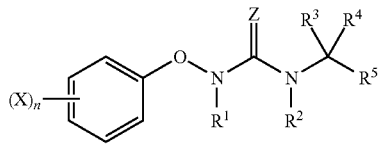

4 Claims, No Drawings

(51) Int. Cl.

| | | |
|---|---|---|
| A61K 31/197 | (2006.01) |
| A61K 31/216 | (2006.01) |
| A61K 31/277 | (2006.01) |
| A61K 31/341 | (2006.01) |
| A61K 31/381 | (2006.01) |
| A61K 31/41 | (2006.01) |
| A61K 31/415 | (2006.01) |
| A61K 31/4196 | (2006.01) |
| A61K 31/42 | (2006.01) |
| A61K 31/421 | (2006.01) |
| A61K 31/4245 | (2006.01) |
| A61K 31/426 | (2006.01) |
| A61K 31/44 | (2006.01) |
| A61K 31/4402 | (2006.01) |
| A61K 31/4406 | (2006.01) |
| A61K 31/4409 | (2006.01) |
| A61K 31/4412 | (2006.01) |
| A61K 31/4418 | (2006.01) |
| A61K 31/4439 | (2006.01) |
| A61K 31/4453 | (2006.01) |
| A61K 31/47 | (2006.01) |
| A61K 31/4709 | (2006.01) |
| A61K 31/4725 | (2006.01) |
| A61K 31/4965 | (2006.01) |
| A61K 31/498 | (2006.01) |
| A61K 31/50 | (2006.01) |
| A61K 31/505 | (2006.01) |
| A61K 31/506 | (2006.01) |
| A61K 31/53 | (2006.01) |
| C07C 271/40 | (2006.01) |
| C07C 317/22 | (2006.01) |
| C07C 381/10 | (2006.01) |
| C07D 213/40 | (2006.01) |
| C07D 213/61 | (2006.01) |
| C07D 213/62 | (2006.01) |
| C07D 213/64 | (2006.01) |
| C07D 213/74 | (2006.01) |
| C07D 213/75 | (2006.01) |
| C07D 213/79 | (2006.01) |
| C07D 213/83 | (2006.01) |
| C07D 213/84 | (2006.01) |
| C07D 213/89 | (2006.01) |
| C07D 215/20 | (2006.01) |
| C07D 215/22 | (2006.01) |
| C07D 217/22 | (2006.01) |
| C07D 231/12 | (2006.01) |
| C07D 237/08 | (2006.01) |
| C07D 239/26 | (2006.01) |
| C07D 241/12 | (2006.01) |
| C07D 249/08 | (2006.01) |
| C07D 253/06 | (2006.01) |
| C07D 257/04 | (2006.01) |
| C07D 261/08 | (2006.01) |
| C07D 263/10 | (2006.01) |
| C07D 271/06 | (2006.01) |
| C07D 277/28 | (2006.01) |
| C07D 295/16 | (2006.01) |
| C07D 307/52 | (2006.01) |
| C07D 333/20 | (2006.01) |
| C07D 401/12 | (2006.01) |
| C07D 417/12 | (2006.01) |
| A01N 47/28 | (2006.01) |
| A01N 47/32 | (2006.01) |
| A01N 47/34 | (2006.01) |
| C07D 213/30 | (2006.01) |
| C07D 295/192 | (2006.01) |
| C07D 307/42 | (2006.01) |
| C07D 333/16 | (2006.01) |
| A01N 47/30 | (2006.01) |
| C07D 211/60 | (2006.01) |
| C07D 213/54 | (2006.01) |
| C07D 253/065 | (2006.01) |

(56) References Cited

FOREIGN PATENT DOCUMENTS

| | | |
|---|---|---|
| JP | 61-126065 A | 6/1986 |
| JP | 01-131146 A | 5/1989 |
| JP | 05-004973 A | 1/1993 |
| JP | 2005-517642 A | 6/2005 |
| JP | 2005-537230 A | 12/2005 |
| JP | 2006-507338 A | 3/2006 |
| JP | 2006-507339 A | 3/2006 |
| WO | WO 87/07269 A1 | 12/1987 |
| WO | WO 01/98301 A1 | 12/2001 |
| WO | WO 03/048128 A1 | 6/2003 |
| WO | WO 03/097604 A1 | 11/2003 |
| WO | WO 2004/047537 A1 | 6/2004 |
| WO | WO 2004/047538 A1 | 6/2004 |
| WO | WO 2005/035508 A2 | 4/2005 |

OTHER PUBLICATIONS

Kohler et al., "Pseudo bases in the isoxazole series. Fourth paper," Journal of the American Chemical Society, 1931, 53:644-650, XP002718816.
Translation of JPH1-131146, "Aryloxyurea, production method thereof and herbicide comprising the same as active component," May 24, 1989, pp. 1-50.
Translation of JPH05-004973, 24 pages (in U.S. Appl. No. 13/877,769).

ARYLOXYUREA COMPOUND AND PEST CONTROL AGENT

CROSS-REFERENCE TO RELATED APPLICATIONS

This application is a Continuation of U.S. application Ser. No. 13/877,769, which is the National Stage application of PCT/JP2011/073082, filed Oct. 6, 2011, which claims priority from Japanese Patent Application No. 2010-229617, filed Oct. 12, 2010, the contents of which are incorporated herein by reference.

TECHNICAL FIELD

The present invention relates to a novel pest control agent. More specifically, the present invention relates to an aryloxyurea compound, which is superior in acaricidal activity and/or fungicidal activity, superior in properties and safety, and which can be industrially and advantageously synthesized, and an acaricide and/or fungicide including the aryloxyurea compound as an active ingredient.

BACKGROUND ART

Compounds represented by formulas (A) to (E), which are structurally relevant to the compound of the present invention, are disclosed in Patent documents 1 to 5.

[Chemical formula 1]

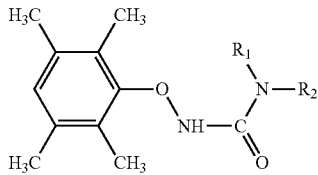

(A)

In the formula, $R_1$ represents a C1-6 alkyl group.
$R_2$ represents a hydrogen atom.

[Chemical formula 2]

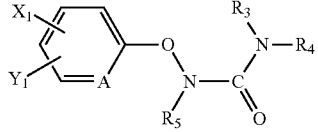

(B)

In the formula, $X_1$ represents a hydrogen atom, chlorine atom or the like.
$Y_1$ represents a hydrogen atom, chlorine atom or the like.
$R_3$ represents a phenyl group or the like.
$R_4$ represents a hydrogen atom, lower alkyl group or the like.
$R_5$ represents a hydrogen atom.
A represents a carbon atom or nitrogen atom.

[Chemical formula 3]

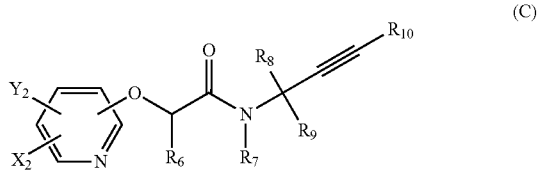

(C)

In the formula, $X_2$ represents a hydrogen atom, halogen atom, C1-8 alkyl group or the like.
$Y_2$ represents a hydrogen atom, halogen atom, C1-8 alkyl group or the like.
$R_6$ represents a phenyl group, cyano group, C1-4 alkyl group or the like.
$R_7$ represents a hydrogen atom, C1-4 alkyl group or the like.
$R_8$ and $R_9$ each independently represents a hydrogen atom, C1-3 alkyl group or the like.
$R_{10}$ represents a halogen atom, C1-4 alkyl group or the like.

[Chemical formula 4]

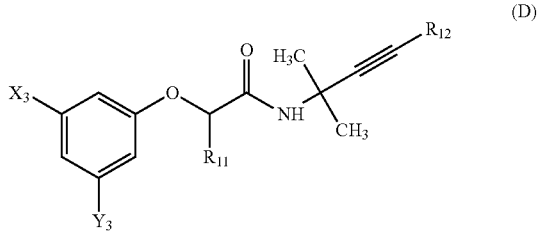

(D)

In the formula, $X_3$ represents a chlorine atom, bromine atom or methyl group.
$Y_3$ represents a chlorine atom, bromine atom or methyl group.
$R_{11}$ represents an ethyl group or an n-propyl group.
$R_{12}$ represents an ethyl group.

[Chemical formula 5]

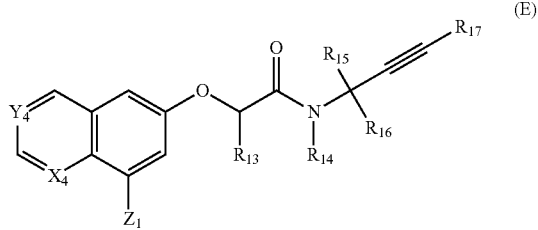

(E)

In the formula, one of $X_4$ and $Y_4$ represents a nitrogen atom or nitrogen oxide, and the other one represents CR (wherein R represents a hydrogen atom, halogen atom or the like), or both $X_4$ and $Y_4$ represent a nitrogen atom.
$Z_1$ represents a hydrogen atom, halogen atom or the like.
$R_{13}$ represents an alkyl group, alkenyl group or the like.
$R_{14}$ represents a benzyloxymethyl group, in which the phenyl ring of the benzyl moiety is optionally substituted with a C1-4 alkoxy group.

$R_{15}$ and $R_{16}$ each independently represents a hydrogen atom, a C1-3 alkyl group or the like, provided that they do not simultaneously represent hydrogen atoms, and when both of them are not hydrogen atoms, the combined number of carbon atoms does not exceed 4.

$R_{17}$ represents a C1-4 alkyl group, C3-6 cycloalkyl group or the like.

PRIOR ART LITERATURE

Patent Documents

Patent document 1: Japanese Unexamined Patent Application Publication No. Sho 61-126065
Patent document 2: Japanese Unexamined Patent Application Publication No. Hei 1-131146
Patent document 3: Japanese Unexamined Patent Application Publication No. 2005-517642
Patent document 4: Japanese Unexamined Patent Application Publication No. 2006-507338
Patent document 5: Japanese Unexamined Patent Application Publication No. 2006-507339

DISCLOSURE OF INVENTION

Problems to be Solved by the Invention

The objective of the present invention is to provide a novel pest control agent, particularly, an acaricide and/or fungicide including as an active ingredient an aryloxyurea compound, which is superior in acaricidal activity and/or fungicidal activity, superior in properties and safety, and which can be industrially and advantageously synthesized.

Means for Solving the Problems

In order to achieve the above objectives, the present inventors conducted extensive studies, and as a result, discovered that an aryloxyurea compound or a salt thereof having a specific structure demonstrates superior acaricidal activity and/or fungicidal activity, can be used as an active ingredient of an acaricide and/or fungicide, and is superior in properties and safety.

The present invention was achieved on the basis of this perception.

Namely, the present invention is as follows:
(1) An aryloxyurea compound represented by formula (I) or a salt thereof.

[Chemical formula 6]

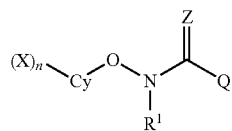

(I)

In formula (I), Cy represents a C6-10 aryl group, or a heteroaryl group.

X represents an unsubstituted or substituted C1-6 alkyl group, unsubstituted or substituted C3-8 cycloalkyl group, unsubstituted or substituted C2-6 alkenyl group, unsubstituted or substituted C2-6 alkynyl group, hydroxy group, unsubstituted or substituted C1-6 alkoxy group, amino group, unsubstituted or substituted C1-6 alkyl amino group, unsubstituted or substituted C1-7 acyl group, unsubstituted or substituted C1-6 alkoxycarbonyl group, unsubstituted or substituted C1-6 alkyl sulfonyl group, unsubstituted or substituted C1-6 alkoxysulfonyl group, unsubstituted or substituted C6-10 aryl group, unsubstituted or substituted heteroaryl group, unsubstituted or substituted hydroxyimino C1-6 alkyl group, nitro group, cyano group, or halogen atom.

n represents the number of X bonded to Cy and represents an integer of 0 to 5. When n is 2 or more, X may be mutually the same or different, and when n is 2 or more, X may bond together to form a ring together with the carbon atoms or nitrogen atoms bonded thereto.

$R^1$ represents an unsubstituted or substituted C1-6 alkyl group, unsubstituted or substituted C2-6 alkenyl group, unsubstituted or substituted C2-6 alkynyl group, unsubstituted or substituted C1-7 acyl group, or unsubstituted or substituted C1-6 alkoxycarbonyl group.

Q represents a group represented by formula (II), formula (III) or formula (IV).

[Chemical formula 7]

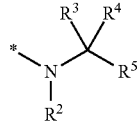

(II)

In formula (II), * represents the bonding position. $R^2$ represents a hydrogen atom, an unsubstituted or substituted C1-6 alkyl group, unsubstituted or substituted C2-6 alkenyl group, unsubstituted or substituted C2-6 alkynyl group, unsubstituted or substituted C1-7 acyl group, or unsubstituted or substituted C1-6 alkoxycarbonyl group. $R^1$ and $R^2$ may bond together to form an unsubstituted or substituted C2-4 alkylene group.

$R^3$ and $R^4$ each independently represents a hydrogen atom, an unsubstituted or substituted C1-6 alkyl group, unsubstituted or substituted C2-6 alkenyl group, unsubstituted or substituted C2-6 alkynyl group, unsubstituted or substituted C6-10 aryl group, unsubstituted or substituted heteroaryl group, or cyano group. Here, $R^3$ and $R^4$ may bond together to form a ring together with the carbon atom bonded thereto.

$R^5$ represents an unsubstituted or substituted C1-6 alkyl group, unsubstituted or substituted C3-8 cycloalkyl group, unsubstituted or substituted C2-6 alkenyl group, unsubstituted or substituted C2-6 alkynyl group, unsubstituted or substituted C1-7 acyl group, carboxyl group, unsubstituted or substituted C1-6 alkoxycarbonyl group, unsubstituted or substituted C2-6 alkenyloxycarbonyl group, unsubstituted or substituted C2-6 alkynyloxycarbonyl group, unsubstituted or substituted aminocarbonyl group, unsubstituted or substituted C6-10 aryl group, unsubstituted or substituted heteroaryl group, unsubstituted or substituted hydroxyimino C1-6 alkyl group, or cyano group.

[Chemical formula 8]

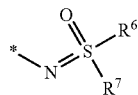

(III)

In formula (III),

* represents the bonding position. $R^6$ and $R^7$ each independently represents an unsubstituted or substituted C1-6 alkyl group, unsubstituted or substituted C3-8 cycloalkyl group, unsubstituted or substituted C2-6 alkenyl group, unsubstituted or substituted C2-6 alkynyl group, unsubstituted or substituted C6-10 aryl group, or unsubstituted or substituted heteroaryl group. Here, $R^6$ and $R^7$ may bond together to form a ring together with the sulfur atom bonded thereto.

[Chemical formula 9]

(IV)

In formula (IV), * represents the bonding position. $R^2$ is as defined above. $R^8$ represents an unsubstituted or substituted C3-8 cycloalkyl group, unsubstituted or substituted C1-6 alkoxycarbonyl group, unsubstituted or substituted C6-10 aryl group, or unsubstituted or substituted heteroaryl group.

Z represents an oxygen atom or sulfur atom.

(2) The aryloxyurea compound represented by formula (I) or a salt thereof, wherein the aryloxyurea compound or a salt thereof is an aryloxyurea compound represented by formula (V) or a salt thereof.

[Chemical formula 10]

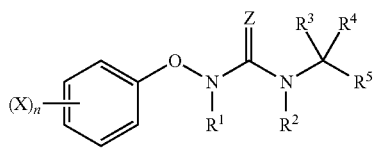

(V)

In formula (V), $R^1$ to $R^5$, X, n, and Z are as defined above.

(3) A pest control agent, comprising at least one of the aryloxyurea compound or a salt thereof according to (1) or (2) as an active ingredient.

(4) An acaricide, comprising at least one of the aryloxyurea compound or a salt thereof according to (1) or (2) as an active ingredient.

(5) A fungicide, comprising at least one of the aryloxyurea compound or a salt thereof according to (1) or (2) as an active ingredient.

Effects of the Invention

The aryloxyurea compound or a salt thereof according to the present invention can protect agricultural crops against infection by harmful organisms. In addition, it also has hygiene applications. Particularly, the compound of the present invention is able to effectively reduce *acarus* and/or plant pathogen infection.

BEST MODE FOR CARRYING OUT THE INVENTION

[Aryloxyurea Compound]

The aryloxyurea compound of the present invention is represented by the following formula (I).

[Chemical formula 11]

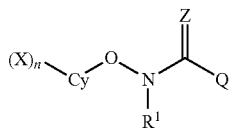

(I)

[Substituents]

The term "unsubstituted" in the present invention refers to a group having only a core group. In the present description, unless specifically indicated otherwise, a group has the meaning of being "unsubstituted" when the group is not described as being "substituted" and is described only using the name of the core group.

On the other hand, the term "substituted" refers to any hydrogen of the core group being substituted with a group having a structure that is the same as or different from the core group. Thus, a "substituent" is another group bonded to the core group. A group may have one substituent or two or more substituents. The two or more substituents may be the same or different.

The term "C1-6", for example, means that the number of carbon atoms of the core group is from 1 to 6. The number of carbon atoms present in a substituent or substituents is not included in the number of carbon atoms. For example, a butyl group having an ethoxy group as a substituent thereof is classified as a C2 alkoxy C4 alkyl group.

There are no particular limitations on "substituents" provided they are chemically acceptable and allow the effects of the present invention to be demonstrated.

Examples of groups able to be "substituents" are as follows:

halogen atoms such as a fluorine atom, chlorine atom, bromine atom or iodine atom;

C1-6 alkyl groups such as a methyl group, ethyl group, n-propyl group, i-propyl group, n-butyl group, s-butyl group, i-butyl group, t-butyl group, n-pentyl group or n-hexyl group;

C3-8 cycloalkyl groups such as a cyclopropyl group, cyclobutyl group, cyclopentyl group, cyclohexyl group or cycloheptyl group;

C2-6 alkenyl groups such as a vinyl group, 1-propenyl group, 2-propenyl group, 1-butenyl group, 2-butenyl group, 3-butenyl group, 1-methyl-2-propenyl group, 2-methyl-2-propenyl group, 1-pentenyl group, 2-pentenyl group, 3-pentenyl group, 4-pentenyl group, 1-methyl-2-butenyl group, 2-methyl-2-butenyl group, 1-hexenyl group, 2-hexenyl group, 3-hexenyl group, 4-hexenyl group or 5-hexenyl group;

C3-8 cycloalkenyl groups such as a 2-cyclopropenyl group, 2-cyclopentenyl group, 3-cyclohexenyl group or 4-cyclooctenyl group;

C2-6 alkynyl groups such as an ethynyl group, 1-propynyl group, 2-propynyl group, 1-butynyl group, 2-butynyl group, 3-butynyl group, 1-methyl-2-propynyl group, 2-methyl-3-butynyl group, 1-pentynyl group, 2-pentynyl group, 3-pentynyl group, 4-pentynyl group, 1-methyl-2-butynyl group, 2-methyl-3-pentynyl group, 1-hexynyl group or 1,1-dimethyl-2-butynyl group;

C1-6 alkoxy groups such as a methoxy group, ethoxy group, n-propoxy group, i-propoxy group, n-butoxy group, s-butoxy group, i-butoxy group or t-butoxy group;

C2-6 alkenyloxy groups such as a vinyloxy group, allyloxy group, propenyloxy group or butenyloxy group;

C2-6 alkynyloxy groups such as an ethynyloxy group or propargyloxy group;

C6-10 aryl groups such as a phenyl group or naphthyl group;

C6-10 aryloxy groups such as a phenoxy group or 1-naphthoxy group;

C7-11 aralkyl groups such as a benzyl group or phenethyl group;

C7-11 aralkyloxy groups such as a benzyloxy group or phenethyloxy group;

C1-7 acyl groups such as a formyl group, acetyl group, propionyl group, benzoyl group or cyclohexylcarbonyl group;

C1-7 acyloxy groups such as a formyloxy group, acetyloxy group, propionyloxy group, benzoyloxy group or cyclohexylcarbonyloxy group;

C1-6 alkoxycarbonyl groups such as a methoxycarbonyl group, ethoxycarbonyl group, n-propoxycarbonyl group, i-propoxycarbonyl group, n-butoxycarbonyl group or t-butoxycarbonyl group;

carboxyl groups;

hydroxyl groups;

C1-6 haloalkyl groups such as a chloromethyl group, chloroethyl group, trifluoromethyl group, 1,2-dichloro-n-propyl group, 1-fluoro-n-butyl group or perfluoro-n-pentyl group;

C2-6 haloalkenyl groups such as a 2-chloro-1-propenyl group or 2-fluoro-1-butenyl group;

C2-6 haloalkynyl groups such as a 4,4-dichloro-1-butynyl group, 4-fluoro-1-pentynyl group or 5-bromo-2-pentynyl group;

C1-6 haloalkoxy groups such as a 2-chloro-n-propoxy group or 2,3-dichlorobutoxy group;

C2-6 haloalkenyloxy groups such as a 2-chloropropenyloxy group or 3-bromobutenyloxy group;

C6-10 haloaryl groups such as a 4-chlorophenyl group, 4-fluorophenyl group or 2,4-dichlorophenyl group;

C6-10 haloaryloxy groups such as a 4-fluorophenyloxy group or 4-chloro-1-naphthoxy group;

halogen-substituted C1-7 acyl groups such as a chloroacetyl group, trifluoroacetyl group, trichloroacetyl group or 4-chlorobenzoyl group;

cyano groups; nitro groups; amino groups;

C1-6 alkylamino groups such as a methylamino group, dimethylamino group or diethylamino group;

C6-10 arylamino groups such as an anilino group or naphthylamino group;

C7-11 aralkylamino groups such as a benzylamino group or phenylethylamino group;

C1-7 acylamino groups such as a formylamino group, acetylamino group, propanoylamino group, butylylamino group, i-propylcarbonylamino group or benzoylamino group;

C1-6 alkoxycarbonylamino groups such as a methoxycarbonylamino group, ethoxycarbonylamino group, n-propoxycarbonylamino group or i-propoxycarbonylamino group;

unsubstituted or substituted aminocarbonyl groups such as an aminocarbonyl group, dimethylaminocarbonyl group, phenylaminocarbonyl group or N-phenyl-N-methylaminocarbonyl group;

imino C1-6 alkyl groups such as an iminomethyl group, (1-imino)ethyl group or (1-imino)-n-propyl group;

hydroxyimino C1-6 alkyl groups such as a hydroxyiminomethyl group, (1-hydroxyimino)ethyl group or (1-hydroxyimino)propyl group;

mercapto groups;

C1-6 alkylthio groups such as a methylthio group, ethylthio group, n-propylthio group, i-propylthio group, n-butylthio group, i-butylthio group, s-butylthio group or t-butylthio group;

C2-6 alkenylthio groups such as a vinylthio group or allylthio group;

C2-6 alkynylthio groups such as an ethynylthio group or propargylthio group;

C6-10 arylthio groups such as a phenylthio group or naphthylthio group;

heteroarylthio groups such as a thiazolylthio group or pyridylthio group;

C7-11 aralkylthio groups such as a benzylthio group or phenethylthio group;

(C1-6 alkythio)carbonyl groups such as a (methylthio)carbonyl group, (ethylthio)carbonyl group, (n-propylthio)carbonyl group, (i-propylthio)carbonyl group, (n-butylthio)carbonyl group, (i-butylthio)carbonyl group, (s-butylthio)carbonyl group or (t-butylthio)carbonyl group;

C1-6 alkylsulfinyl groups such as a methylsulfinyl group, ethylsulfinyl group or t-butylsulfinyl group;

C2-6 alkenylsulfinyl groups such as an allylsulfinyl group;

C2-6 alkynylsulfinyl groups such as a propargylsulfinyl group;

C6-10 arylsulfinyl groups such as a phenylsulfinyl group;

heteroarylsulfinyl groups such as a thiazolylsulfinyl group or pyridylsulfinyl group;

C7-11 aralkylsulfinyl groups such as a benzylsulfinyl group or phenethylsulfinyl group;

C1-6 alkylsulfonyl groups such as a methylsulfonyl group, ethylsulfonyl group or t-butylsulfonyl group;

C2-6 alkenylsulfonyl groups such as an allylsulfonyl group;

C2-6 alkynylsulfonyl groups such as a propargylsulfonyl group;

C6-10 arylsulfonyl groups such as a phenylsulfonyl group;

heteroarylsulfonyl groups such as a thiazolylsulfonyl group or pyridylsulfonyl group;

C7-11 aralkylsulfonyl groups such as a benzylsulfonyl group or phenethylsulfonyl group;

5-membered heteroaryl groups such as a pyrrolyl group, furyl group, thienyl group, imidazolyl group, pyrazolyl group, oxazolyl group, isoxazolyl group, thiazolyl group, isothiazolyl group, triazolyl group, oxadiazolyl group, thiadiazolyl group or tetrazolyl group;

6-membered heteroaryl groups such as a pyridyl group, pyrazinyl group, pyrimidinyl group, pyridazinyl group or triazinyl group;

condensed heteroaryl groups such as an indolyl group, benzofuryl group, benzothienyl group, benzimidazolyl group, benzoxazolyl group, benzothiazolyl group, quinolyl group, isoquinolyl group or quinoxalinyl group;

saturated heterocyclic groups such as an aziridinyl group, oxiranyl group, pyrrolidinyl group, tetrahydrofuranyl group, piperidyl group, piperazinyl group or morpholinyl group;

triC1-6 alkyl-substituted silyl groups such as a trimethylsilyl group, triethylsilyl group or t-butyldimethylsilyl group;

triphenylsilyl groups;

In addition, these "substituents" may further have other "substituents".

[Cy]

In formula (I), Cy represents a C6-10 aryl group or heteroaryl group.

The "C6-10 aryl group" may be a monocyclic aryl group, or a polycyclic aryl group in which multiple rings are bonded. The polycyclic aryl group may be a group in which at least one of the rings is an aromatic ring while the remaining rings are any of saturated aliphatic rings, unsaturated aliphatic rings or aromatic rings. Examples of the C6-10 aryl groups include a phenyl group, naphthyl group, azulenyl group, indenyl group, indanyl group, tetralinyl group and the like.

The "heteroaryl group" is a 5- to 10-membered aryl group including other than carbon atom 1 to 4 heteroatoms selected from the group consisting of nitrogen atom, oxygen atom and sulfur atom as an atom constituting the ring. In this case, the heteroaryl group may be a monocyclic aryl group, or a polycyclic aryl group in which multiple rings are condensed.

Examples of the heteroaryl group are the same as the examples of a 5-membered heteroaryl group, 6-membered heteroaryl group and condensed heteroaryl group listed as the examples of the "substitutents".

Among these examples, Cy is preferably a phenyl group, naphthyl group, pyridyl group, pyrimidinyl group, pyridazinyl group, quinolyl group, isoquinolyl group, quinoxalinyl group, and more preferably a phenyl group.

[X]

In formula (I), X represents an unsubstituted or substituted C1-6 alkyl group, unsubstituted or substituted C3-8 cycloalkyl group, unsubstituted or substituted C2-6 alkenyl group, unsubstituted or substituted C2-6 alkynyl group, hydroxy group, unsubstituted or substituted C1-6 alkoxy group, amino group, unsubstituted or substituted C1-6 alkyl amino group, unsubstituted or substituted C1-7 acyl group, unsubstituted or substituted C1-6 alkoxycarbonyl group, unsubstituted or substituted C1-6 alkyl sulfonyl group, unsubstituted or substituted C1-6 alkoxysulfonyl group, unsubstituted or substituted C6-10 aryl group, unsubstituted or substituted heteroaryl group, unsubstituted or substituted hydroxyimino C1-6 alkyl group, nitro group, cyano group, or halogen atom.

n represents the number of X bonded to Cy and represents an integer of 0 to 5. When n is 2 or more, X may be mutually the same or different, and when n is 2 or more, X may bond together to form a ring together with the carbon atoms or nitrogen atoms bonded thereto.

The "C1-6 alkyl group" of X may be a linear alkyl group or a branched alkyl group. Examples of the alkyl group include a methyl group, ethyl group, n-propyl group, n-butyl group, n-pentyl group, n-hexyl group, i-propyl group, i-butyl group, s-butyl group, t-butyl group, i-pentyl group, neopentyl group, 2-methyl butyl group, 2,2-dimethyl propyl group, i-hexyl group and the like.

Examples of the "substituted alkyl group" include C3-8 cycloalkyl C1-6 alkyl groups such as a cyclopropyl methyl group, 2-cyclopropyl ethyl group, cyclopentyl methyl group, 2-cyclohexyl ethyl group, 2-cyclooctyl ethyl group or the like;

C1-6 haloalkyl groups such as a fluoromethyl group, chloromethyl group, bromomethyl group, difluoromethyl group, dichloromethyl group, dibromomethyl group, trifluoromethyl group, trichloromethyl group, tribromomethyl group, 2,2,2-tolufluoroethyl group, 2,2,2-trichloroethyl group, pentafluoroethyl group, 4-fluorobutyl group, 4-chlorobutyl group, 3,3,3-trifluoropropyl group, 2,2,2-trifluoro-1-trifluoromethyl ethyl group, perfluorohexyl group, perchlorohexyl group, perfluorooctyl group, perchlorooctyl group, 2,4,6-trichlorohexyl group or the like;

hydroxy C1-6 alkyl groups such as a hydroxymethyl group, 2-hydroxyethyl group or the like;

C1-6 alkoxy C1-6 alkyl groups such as a methoxymethyl group, ethoxymethyl group, methoxyethyl group, ethoxyethyl group, methoxy-n-propyl group, ethoxymethyl group, ethoxyethyl group, n-propoxymethyl group, i-propoxyethyl group, s-butoxymethyl group, t-butoxyethyl group or the like;

C2-6 alkenyloxy C1-6 alkyl groups such as a vinyloxymethyl group, allyloxymethyl group, propenyloxymethyl group, butenyloxymethyl group or the like;

heteroaryloxy C1-6 alkyl groups such as a pyridine-2-yloxymethyl group or the like;

C1-7 acyl groups such as a formyl group, acetyl group, propionyl group or the like;

C1-7 acyloxy C1-6 alkyl groups such as a formyloxymethyl group, acetoxymethyl group, 2-acetoxyethyl group, propionyloxymethyl group, propionyloxyethyl group or the like;

carboxyl group C1-6 alkyl groups such as a carboxyl methyl group, carboxyl ethyl group or the like;

C1-6 alkoxycarbonyl C1-6 alkyl groups such as a methoxycarbonyl methyl group, ethoxycarbonyl methyl group, n-propoxycarbonyl methyl group, i-propoxycarbonyl methyl group or the like;

C1-7 acyl amino C1-6 alkyl groups such as a formamide methyl group, acetamide methyl group, 2-acetamide ethyl group, propionyl aminomethyl group, propionyl aminoethyl group or the like;

C1-6 alkyl aminocarbonyl C1-6 alkyl groups such as a methyl aminocarbonyl methyl group, ethyl aminocarbonyl methyl group, i-propyl aminocarbonyl methyl group, t-butyl aminocarbonyl methyl group, s-butyl aminocarbonyl methyl group, n-pentyl aminocarbonyl methyl group or the like;

C1-6 alkoxycarbonyl amino C1-6 alkyl groups such as a methoxycarbonyl aminomethyl group, ethoxycarbonyl aminomethyl group, i-propoxycarbonyl aminomethyl group, t-butoxycarbonyl aminomethyl group, s-butyloxycarbonyl aminomethyl group, n-pentyloxycarbonyl aminomethyl group or the like;

C7-11 aralkyl groups such as a benzyl group, phenethyl group or the like;

C6-10 aryl carbonyl amino C1-6 alkyl groups such as a benzoyl aminomethyl group or the like; and the like.

Examples of the "C3-8 cycloalkyl group" of X include a cyclopropyl group, cyclobutyl group, cyclopentyl group, cyclohexyl group, cycloheptyl group and the like.

Examples of the "C2-6 alkenyl group" of X include a vinyl group, 1-propenyl group, 2-propenyl group, 1-butenyl group, 2-butenyl group, 3-butenyl group, 1-methyl-2-propenyl group, 2-methyl-2-propenyl group, 1-pentenyl group, 2-pentenyl group, 3-pentenyl group, 4-pentenyl group, 1-methyl-2-butenyl group, 2-methyl-2-butenyl group, 1-hexenyl group, 2-hexenyl group, 3-hexenyl group, 4-hexenyl group, 5-hexenyl group and the like.

Examples of the "substituted C2-6 alkenyl group" include C2-6 haloalkenyl groups such as 2-chloro-1-propenyl group, 2-fluoro-1-butenyl group and the like.

Examples of the "C2-6 alkynyl group" of X include an ethynyl group, 1-propynyl group, 2-propynyl group, 1-butynyl group, 2-butynyl group, 3-butynyl group, 1-methyl-2-propynyl group, 2-methyl-3-butynyl group, 1-pentynyl group, 2-pentynyl group, 3-pentynyl group, 4-pentynyl group, 1-methyl-2-butynyl group, 2-methyl-3-pentynyl group, 1-hexynyl group, 1,1-dimethyl-2-butynyl group and the like.

Examples of the "substituted C2-6 alkynyl group" include C2-6 haloalkynyl groups such as a 4,4-dichloro-1-butynyl group, 4-fluoro-1-pentynyl group, 5-bromo-2-pentynyl group and the like.

Examples of the "C1-6 alkoxy group" of X include a methoxy group, ethoxy group, n-propoxy group, n-butoxy group, n-pentyloxy group, n-hexyloxy group, i-propoxy group, i-butoxy group, s-butoxy group, t-butoxy group, i-hexyloxy group and the like.

Examples of the "substituted C1-6 alkoxy group" include C1-6 haloalkoxy groups such as a chloromethoxy group, dichloromethoxy group, difluoromethoxy group, trichloromethoxy group, trifluoromethoxy group, 1-fluoroethoxy group, 1,1-difluoroethoxy group, 2,2,2-trifluoroethoxy group, pentafluoroethoxy group and the like.

Examples of the "C1-6 alkyl amino group" of X include a methyl amino group, dimethyl amino group, diethyl amino group and the like.

Examples of the "C1-7 acyl group" of X include a formyl group, acetyl group, propionyl group, benzoyl group and the like.

Examples of the "substituted C1-7 acyl group" include halogen-substituted C1-7 acyl groups such as a chloroacetyl group, trifluoroacetyl group, trichloroacetyl group, 4-chlorobenzoyl group and the like.

Examples of the "C1-6 alkoxycarbonyl group" of X include a methoxycarbonyl group, ethoxycarbonyl group, n-propoxycarbonyl group, i-propoxycarbonyl group and the like.

Examples of the "substituted C1-6 alkoxycarbonyl group" include C3-8 cycloalkyl C1-6 alkoxycarbonyl groups such as a cyclopropyl methoxycarbonyl group, cyclobutyl methoxycarbonyl group, cyclopentyl methoxycarbonyl group, cyclohexyl methoxycarbonyl group, 2-methyl cyclopropyl methoxycarbonyl group, 2,3-dimethyl cyclopropyl methoxycarbonyl group, 2-chlorocyclopropyl methoxycarbonyl group, 2-cyclopropyl ethoxycarbonyl group;

C1-6 haloalkoxycarbonyl groups such as a fluoromethoxycarbonyl group, chloromethoxycarbonyl group, bromomethoxycarbonyl group, difluoromethoxycarbonyl group, dichloromethoxycarbonyl group, dibromomethoxycarbonyl group, trifluoromethoxycarbonyl group, trichloromethoxycarbonyl group, tribromomethoxycarbonyl group, 2,2,2-trifluoroethoxycarbonyl group, 2,2,2-trichloroethoxycarbonyl group, pentafluoroethoxycarbonyl group, 4-fluorobutoxycarbonyl group, 3,3,3-trifluoropropoxycarbonyl group, 2,2,2-trifluoro-1-trifluoromethyl ethoxycarbonyl group, perfluorohexyloxycarbonyl group;

and the like.

Examples of the "C1-6 alkyl sulfonyl group" of X include a methyl sulfonyl group, ethyl sulfonyl group, t-butyl sulfonyl group and the like.

Examples of the "C1-6 alkoxysulfonyl group" of X include a methoxysulfonyl group, ethoxysulfonyl group, t-butoxysulfonyl group and the like.

Examples of the "C6-10 aryl group" and "heteroaryl group" of X are the same as those listed as the examples of Cy.

Examples of the substituents on the "C6-10 aryl group" and "heteroaryl group" of X include halogen atoms such as a fluorine atom, chlorine atom, bromine atom, iodine atom or the like;

C1-6 alkyl groups such as a methyl group, ethyl group, n-propyl group, i-propyl group, n-butyl group, s-butyl group, i-butyl group, t-butyl group, n-pentyl group, n-hexyl group or the like;

C1-6 haloalkyl groups such as a chloromethyl group, chloroethyl group, trifluoromethyl group, 1,2-dichloro-n-propyl group, 1-fluoro-n-butyl group, perfluoro-n-pentyl group or the like;

cyano groups;

and the like.

Examples of the "hydroxyimino C1-6 alkyl group" of X include a hydroxyiminomethyl group, (1-hydroxyimino)ethyl group, (1-hydroxyimino)propyl group and the like.

Examples of the "substituted hydroxyimino C1-6 alkyl group" include C1-6 alkoxyimino C1-6 alkyl groups such as a methoxyiminomethyl group, (1-methoxyimino)ethyl group, (1-methoxyimino)propyl group, ethoxyiminomethyl group, (1-ethoxyimino)ethyl group, (1-ethoxyimino)propyl group or the like; C3-8 cycloalkyl C1-6 alkoxyimino C1-6 alkyl groups such as a (1-cyclopropyl methoxyimino)ethyl group; C7-11 aralkyloxyimino C1-6 alkyl groups such as a benzyloxyiminomethyl group, (1-benzyloxyimino)ethyl group; and the like.

Examples of the "halogen atom" of X include a fluorine atom, chlorine atom, bromine atom, iodine atom and the like.

Examples of the ring formed by bonding X together with the carbon atoms or nitrogen atoms bonded thereto when n is 2 or more, include a cyclopentene ring, cyclohexene ring, 3,4-dihydro-2H-pyran ring, 3,4-dihydro-2H-thiopyran ring, 3,4-dihydro-2H-thiopyran 1,1-dioxide ring and the like.

[$R^1$]

In formula (I), $R^1$ represents an unsubstituted or substituted C1-6 alkyl group, unsubstituted or substituted C2-6 alkenyl group, unsubstituted or substituted C2-6 alkynyl group, unsubstituted or substituted C1-7 acyl group, or unsubstituted or substituted C1-6 alkoxycarbonyl group.

Examples of the "C1-6 alkyl group", "C2-6 alkenyl group", "C2-6 alkynyl group", "C1-7 acyl group" and "C1-6 alkoxycarbonyl group" of $R^1$ are the same as those listed as the examples of X.

[Q]

In formula (I), Q represents a group represented by formula (II), formula (III) or formula (IV).

[Chemical formula 12]

(II)

In formula (II), * represents the bonding position.

[$R^2$]

In formula (II), $R^2$ represents a hydrogen atom, unsubstituted or substituted C1-6 alkyl group, unsubstituted or substituted C2-6 alkenyl group, unsubstituted or substituted C2-6 alkynyl group, unsubstituted or substituted C1-7 acyl group, or unsubstituted or substituted C1-6 alkoxycarbonyl group. $R^1$ and $R^2$ may bond together to form an unsubstituted or substituted C2-4 alkylene group.

Examples of the "C1-6 alkyl group", "C2-6 alkenyl group", "C2-6 alkynyl group", "C1-7 acyl group" and "C1-6 alkoxycarbonyl group" of $R^2$ are the same as those listed as the examples of X.

Examples of the "unsubstituted or substituted C2-4 alkylene group" formed by boding $R^1$ and $R^2$ include an ethylene group, propylene group (trimethylene group) and the like.

[$R^3$, $R^4$]

In formula (II), $R^3$ and $R^4$ each independently represents a hydrogen atom, unsubstituted or substituted C1-6 alkyl group, unsubstituted or substituted C2-6 alkenyl group, unsubstituted or substituted C2-6 alkynyl group, unsubstituted or substituted C6-10 aryl group, unsubstituted or substituted heteroaryl group or cyano group. Here, $R^3$ and $R^4$ may bond together to form a ring together with the carbon atom bonded thereto.

Examples of the "C1-6 alkyl group", "C2-6 alkenyl group" and "C2-6 alkynyl group" of $R^3$ and $R^4$ are the same as those listed as the examples of X.

Examples of the "C6-10 aryl group" and "heteroaryl group" of $R^3$ and $R^4$ are the same as those listed as the examples of Cy.

Examples of the "ring" formed by bonding $R^3$ and $R^4$ together with the carbon atom bonded thereto include a cyclopropane ring, cyclobutane ring, cyclopentane ring, cyclohexane ring, oxirane ring and the like.

[$R^5$]

In formula (II), $R^5$ represents an unsubstituted or substituted C1-6 alkyl group, unsubstituted or substituted C3-8 cycloalkyl group, unsubstituted or substituted C2-6 alkenyl group, unsubstituted or substituted C2-6 alkynyl group, unsubstituted or substituted C1-7 acyl group, carboxyl group, unsubstituted or substituted C1-6 alkoxycarbonyl group, unsubstituted or substituted C2-6 alkenyloxycarbonyl group, unsubstituted or substituted C2-6 alkynyloxycarbonyl group, unsubstituted or substituted aminocarbonyl group, unsubstituted or substituted C6-10 aryl group, unsubstituted or substituted heteroaryl group, unsubstituted or substituted hydroxyimino C1-6 alkyl group or cyano group.

Examples of the "C1-6 alkyl group", "C3-8 cycloalkyl group", "C2-6 alkenyl group", "C2-6 alkynyl group", "C1-7 acyl group" and "C1-6 alkoxycarbonyl group" of $R^5$ are the same as those listed as the examples of X.

Examples of the "C6-10 aryl group" of $R^5$ include a phenyl group, naphthyl group, azulenyl group, indenyl group, indanyl group, tetralinyl group and the like.

Examples of the "heteroaryl group" of $R^5$ include 5-membered heteroaryl groups such as a pyrrolyl group, furyl group, thienyl group, imidazolyl group, pyrazolyl group, oxazolyl group, isoxazolyl group, thiazolyl group, isothiazolyl group, triazolyl group, oxadiazolyl group, thiadiazolyl group, tetrazolyl group or the like;

6-membered heteroaryl groups such as a pyridyl group, pyrazinyl group, pyrimidinyl group, pyridazinyl group, triazinyl group or the like;

condensed heteroaryl groups such as an indolyl group, benzofuryl group, benzothienyl group, benzimidazolyl group, benzoxazolyl group, benzothiazolyl group, quinolyl group, isoquinolyl group, quinoxalinyl group or the like;

partially unsaturated 5-membered heterocyclic groups such as a pyrrolinyl group, imidazolinyl group, pyrazolinyl group, oxazolinyl group, thiazolinyl group or the like;

and the like.

Among these examples, a phenyl group, pyridyl group and the like are preferable.

Examples of the substituents on the "C6-10 aryl group" and "hetero aryl group" of $R^5$ include halogen atoms such as a fluorine atom, chlorine atom, bromine atom, iodine atom;

C1-6 alkyl groups such as a methyl group, ethyl group, n-propyl group, i-propyl group, n-butyl group, s-butyl group, i-butyl group, t-butyl group, n-pentyl group, n-hexyl group;

C1-6 haloalkyl groups such as a chloromethyl group, chloroethyl group, trifluoromethyl group, 1,2-dichloro-n-propyl group, 1-fluoro-n-butyl group, perfluoro-n-pentyl group;

cyano group;

and the like.

Examples of the "C2-6 alkenyloxycarbonyl group" include an ethenyloxycarbonyl group, 1-methyl-2-propenyloxycarbonyl group, 2-methyl-1-propenyloxycarbonyl group and the like.

Examples of the "C2-6 alkynyloxycarbonyl group" include an ethynyloxycarbonyl group, propargyloxycarbonyl group, 1-methyl propargyloxycarbonyl group, 2-butynyloxycarbonyl group and the like.

Examples of the "substituted aminocarbonyl group" include a C1-6 alkyl aminocarbonyl groups such as a methyl aminocarbonyl group, ethyl aminocarbonyl group, i-propyl aminocarbonyl group, t-butyl aminocarbonyl group, s-butyl aminocarbonyl group, n-pentyl aminocarbonyl group or the like; di C1-6 alkyl aminocarbonyl groups such as a dimethyl aminocarbonyl group, diethyl aminocarbonyl group or the like; C3-8 cycloalkyl aminocarbonyl groups such as a cyclopropyl aminocarbonyl group, cyclopentyl aminocarbonyl group, cyclohexyl aminocarbonyl group or the like; C2-6 alkynyl aminocarbonyl groups such as a 2-propynyl aminocarbonyl group or the like; phenyl aminocarbonyl group, N-phenyl-N-methyl aminocarbonyl group or the like; C1-6 alkoxy C1-6 alkyl aminocarbonyl groups such as a methoxyethyl aminocarbonyl group or the like; C1-6 haloalkyl aminocarbonyl groups such as a 2,2,2-trifluoroethyl aminocarbonyl group or the like; C3-8 cycloalkyl C1-6 alkyl aminocarbonyl groups such as a cyclopropyl methyl aminocarbonyl group or the like; C7-11 aralkyl aminocarbonyl groups such as a benzyl aminocarbonyl group or the like; 1-substituted cyclic amine carbonyl groups such as a piperidine-1-yl carbonyl group or the like;

Examples of the "hydroxyimino C1-6 alkyl group" include a hydroxyiminomethyl group, (1-hydroxyimino)ethyl group, (1-hydroxyimino)propyl group and the like.

Examples of the "substituted hydroxyimino C1-6 alkyl group" include C1-6 alkoxyimino C1-6 alkyl groups such as a methoxyiminomethyl group, 1-methoxyimino)ethyl group, (1-methoxyimino)propyl group, ethoxyiminomethyl group, (1-ethoxyimino)ethyl group, (1-ethoxyimino)propyl group or the like; C3-8 cycloalkyl C1-6 alkoxyimino C1-6 alkyl groups such as a (1-cyclopropyl methoxyimino)ethyl group or the like; C7-11 aralkyloxyimino C1-6 alkyl groups such as a benzyloxyiminomethyl group, (1-benzyloxyimino) ethyl group or the like; and the like.

[Chemical formula 13]

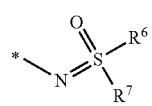

(III)

In formula (III), * represents the bonding position.

[$R^6$, $R^7$]

In formula (III), $R^6$ and $R^7$ each independently represents an unsubstituted or substituted C1-6 alkyl group, unsubstituted or substituted C3-8 cycloalkyl group, unsubstituted or substituted C2-6 alkenyl group, unsubstituted or substituted C2-6 alkynyl group, unsubstituted or substituted C6-10 aryl group, or unsubstituted or substituted heteroaryl group. Here, $R^6$ and $R^7$ may bond together to form a ring together with the sulfur atom bonded thereto.

Examples of the "C1-6 alkyl group", "C3-8 cycloalkyl group", "C2-6 alkenyl group" and "C2-6 alkynyl group" of $R^6$ and $R^7$ are the same as those listed as the examples of X.

Examples of the "C6-10 aryl group" and "heteroaryl group" of $R^6$ and $R^7$ are the same as those listed as the examples of Cy.

Examples of the substituents on the "C6-10 aryl group" and "heteraryl group" of $R^6$ and $R^7$ include halogen atoms such as a fluorine atom, chlorine atom, bromine atom, iodine atom or the like;

C1-6 alkyl groups such as a methyl group, ethyl group, n-propyl group, i-propyl group, n-butyl group, s-butyl group, i-butyl group, t-butyl group, n-pentyl group, n-hexyl group or the like;

C1-6 haloalkyl groups such as a chloromethyl group, chloroethyl group, trifluoromethyl group, 1,2-dichloro-n-propyl group, 1-fluoro-n-butyl group, perfluoro-n-pentyl group or the like;

cyano group;

and the like.

Examples of the "ring" formed by bonding $R^6$ and $R^7$ together with the sulfur atom bonded thereto include a tetrahydrothiophene ring, tetrahydrothiopyran ring, oxathiane ring and the like.

[Chemical formula 14]

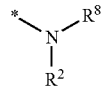

(IV)

In formula (IV), * represents the bonding position. $R^2$ is as defined above. $R^8$ represents an unsubstituted or substituted C3-8 cycloalkyl group, unsubstituted or substituted C1-6 alkoxycarbonyl group, unsubstituted or substituted C6-10 aryl group, or unsubstituted or substituted heteroaryl group.

Examples of the "C3-8 cyclocalkyl group" of $R^8$ are the same as those listed as the examples of X.

Examples of the "substituted C3-8 cycloalkyl group" include C6-10 aryl C3-8 cycloalkyl groups such as a 2-phenylcyclopropyl group or the like; and the like.

Examples of the "C1-6 alkoxycarbonyl group" of $R^8$ are the same as those listed as the examples of X.

Examples of the "C6-10 aryl group" of $R^8$ include a phenyl group, naphthyl group, azulenyl group, indenyl group, indanyl group, tetralinyl group and the like.

Examples of the "heteroaryl group" of $R^8$ include 5-membered heteroaryl groups such as a pyrrolyl group, furyl group, thienyl group, imidazolyl group, pyrazolyl group, oxazolyl group, isoxazolyl group, thiazolyl group, isothiazolyl group, triazolyl group, oxadiazolyl group, thiadiazolyl group, tetrazolyl group or the like;

6-membered heteroaryl groups such as a pyridyl group, pyrazinyl group, pyrimidinyl group, pyridazinyl group, triazinyl group or the like;

condensed heteroaryl groups such as an indolyl group, benzofuryl group, benzothienyl group, benzimidazolyl group, benzoxazolyl group, benzothiazolyl group, quinolyl group or the like;

partially saturated heterocyclic groups such as a tetrahydroquinolyl group or the like;

and the like.

Examples of the substituents on the "C6-10 aryl group" and "heteroaryl group" of $R^8$ include halogen atoms such as a fluorine atom, chlorine atom, bromine atom, iodine atom or the like;

C1-6 alkyl groups such as a methyl group, ethyl group, n-propyl group, i-propyl group, n-butyl group, s-butyl group, i-butyl group, t-butyl group, n-pentyl group, n-hexyl group or the like;

C1-6 haloalkyl groups such as a chloromethyl group, chloroethyl group, trifluoromethyl group, 1,2-dichloro-n-propyl group, 1-fluoro-n-butyl group, perfluoro-n-pentyl group or the like;

cyano groups;

and the like.

[Z]

In formula (I), Z represents an oxygen atom or sulfur atom, and preferably represents an oxygen atom.

[Aryloxyurea Compound Represented by Formula (V)]

Among the aryloxyurea compounds of the present invention, a compound represented by formula (I), wherein Cy represents a phenyl group, Q represents a group represented by formula (II) is preferable. In other words, an aryloxyurea compound represented by formula (V) is preferable.

[Chemical formula 15]

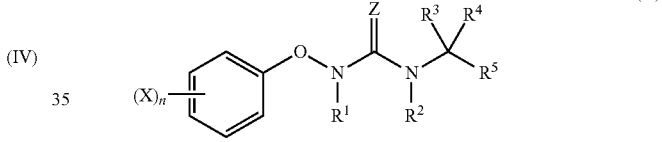

(V)

In formula (V), $R^1$ to $R^5$, X, n, and Z are as defined above.

[Salt of Aryloxyurea Compound]

There are no particular limitations on the salts of the aryloxyurea compound of the present invention provided it is an agriculturally and horticulturally allowable salt. Examples of the salt include salts of inorganic acids such as hydrochloric acid or sulfuric acid; salts of organic acids such as acetic acid or lactic acid; salts of alkaline metals such as lithium, sodium or potassium; salts of alkaline earth metals such as calcium or magnesium; salts of transition metals such as iron or copper; and salts of organic bases such as ammonia, triethylamine, tributylamine, pyridine or hydrazine. The salts of aryloxyurea compound of the present invention may be produced by well-known methods.

[Production Method]

The following provides an explanation of a production method of the aryloxyurea compound of the present invention.

1) The production method shown in the following scheme can be an example of the first production method.

[Chemical formula 16]

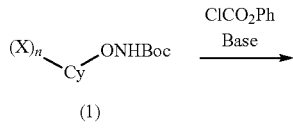

(1)

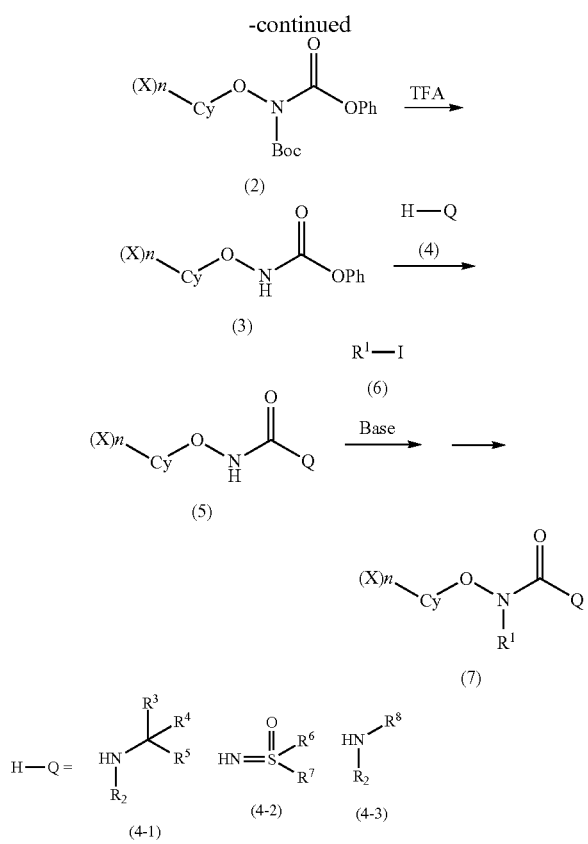

a) A diester compound represented by formula (2) (hereinafter, may be referred to as "compound (2)") is obtained by reacting an aryloxyamine compound represented by formula (1) (hereinafter, may be referred to as "compound (1)") with chloroformic acid phenyl ester in the presence of a base. Next, an N-aryloxycarbamic acid phenyl ester represented by formula (3) (hereinafter, may be referred to as "compound (3)") is produced by performing de-Boc reaction in the presence of trifluoroacetic acid. In formulas (1) to (3), X, n, and Cy are as defined as above.

The amount of chloroformic acid phenyl is generally 1 to 2 mol, and preferably 1.0 to 1.2 mol with respect to 1 mol of compound (1).

Although the reaction may be performed in the absence of a base, it is preferable to perform the reaction in the presence of a base. Examples of the base include pyridine, triethylamine, potassium hydroxide and the like. The amount of the base is generally 1 to 2 mol with respect to 1 mol of compound (1).

The reaction may be performed in a solvent. There are no particular limitations on the solvent provided it is inactive against the reaction. Examples of the solvent include ether type solvents such as dioxane, 1,2-dimethoxyethane, tetrahydrofuran; aromatic hydrocarbon type solvents such as toluene, benzene, xylene; aliphatic hydrocarbon type solvents such as n-pentane, n-hexane, n-heptane; halogenated hydrocarbon type solvents such as dichloromethane, chloroform, carbon tetrachloride, 1,2-dichloroethane; amide type solvents such as N,N-dimethyl formamide, N,N-dimethyl acetamide, N-methyl pyrrolidone; nitrile type solvents such as acetonitrile, benzonitrile; and mixed solvents including two or more of these solvents; and the like. Although there are no particular limitations on the amount of the solvent, it is generally 1 to 100 ml with respect to 1 g of compound (1).

The reaction temperature ranges from −20° C. to the boiling point of the solvent. Although the reaction time varies according to the reaction scale, it is generally from minutes to hours.

Next, the de-Boc reaction is performed in the presence of an acid catalyst. Examples of the acid include inorganic acids such as hydrochloric acid, sulfuric acid, nitric acid; acetic acids, trifluoroacetic acids, methane sulfonic acids, p-toluene sulfonic acids and the like. Among these examples, trifluoroacetic acid is preferable. The amount of the acid is generally 1 to 20 mol with respect to 1 mol of compound (2).

The reaction may be performed in a solvent. There are no particular limitations on the solvent provided it is inactive against the reaction. Examples of the solvent are the same as the examples of the solvent used for producing compound (2). Although there are no particular limitations on the amount of the solvent, it is generally 1 to 100 ml with respect to 1 g of compound (2).

The reaction temperature ranges from room temperature to the boiling point of the solvent. Although the reaction time varies according to the reaction scale, it is generally from minutes to hours.

b) an aryloxyurea compound represented by formula (5) (hereinafter, may be referred to as "compound (5)") is produced by reacting compound (3) with a compound represented by formula (4) (hereinafter, may be referred to as "compound (4)"). Here, compound (4) may be an amine compound represented by formula (4-1) (hereinafter, may be referred to as "compound (4-1)"), a sulfoximine compound represented by formula (4-2) (hereinafter, may be referred to as "compound (4-2)") or an amine compound represented by formula (4-3) (herein after, may be referred to as "compound (4-3)"). In formula (4) and formula (5), X, n, Q and Cy are as defined above. In formula (4-1), formula (4-2) and formula (4-3), $R^2$ to $R^8$ are as defined above.

The amount of compound (4) is generally 1 to 2 mol, and preferably 1.0 to 1.2 mol with respect to 1 mol of compound (3).

The reaction may be performed in a solvent. There are no particular limitations on the solvent provided it is inactive against the reaction. Examples of the solvent are the same as the examples of the solvent used for producing compound (2). Although there are no particular limitations on the amount of the solvent, it is generally 1 to 100 ml with respect to 1 g of compound (3).

In addition, when performing a reaction with compound (4-2), it is preferable to perform in the presence of a base. Examples of the base include pyridine, triethylamine, potassium hydroxide and the like. The amount of the base is generally 1 to 2 mol with respect to 1 mol of compound (3).

The reaction temperature ranges from room temperature to the boiling point of the solvent. Although the reaction time varies according to the reaction scale, it is generally from minutes to hours.

b) an aryloxyurea compound represented by formula (7) (hereinafter, may be referred to as "compound (7)"), which is a target compound, is produced by reacting compound (5) with an iodinated compound represented by formula (6) (hereinafter, may be referred to as "compound (6)") in the presence of a base. In formula (6) and formula (7), X, n, Q, $R^1$ and Cy are as defined above.

The amount of compound (6) is generally 1 to 2 mol, and preferably 1.0 to 1.2 mol with respect to 1 mol of compound (5).

Examples of the base include pyridine, triethylamine, potassium hydroxide, calcium carbonate and the like. The amount of the base is generally 1 to 2 mol with respect to 1 mol of compound (5).

The reaction may be performed in a solvent. There are no particular limitations on the solvent provided it is inactive against the reaction. Examples of the solvent are the same as the examples of the solvent used for producing compound (2). Although there are no particular limitations on the amount of the solvent, it is generally 1 to 100 ml with respect to 1 g of compound (5).

The reaction temperature ranges from −20° C. to the boiling point of the solvent. Although the reaction time varies according to the reaction scale, it is generally from minutes to hours.

2) The production method shown in the following scheme can be an example of the second production method.

[Chemical formula 17]

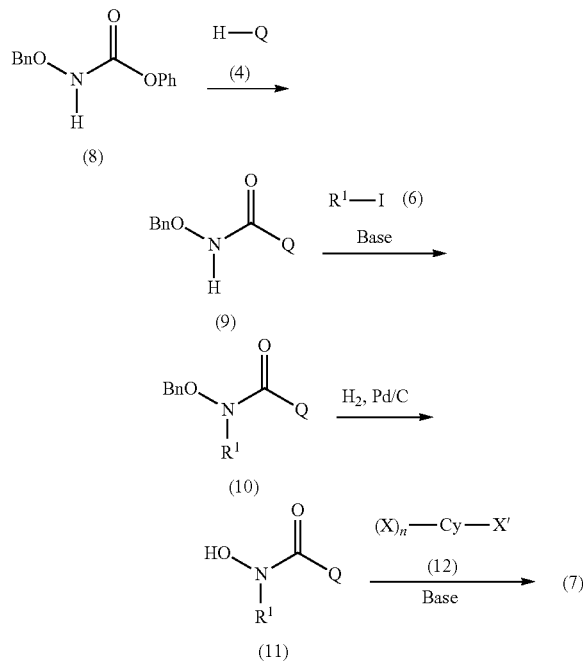

a) A benzyloxyurea compound represented by formula (9) (hereinafter, may be referred to as "compound (9)") is produced by reacting an N-benzyloxycarbamic acid phenyl ester (hereinafter, may be referred to as "compound (8)") able to be produced by well-known methods with compound (4). In formula (9), Q is as defined above.

The amount of compound (4) is generally 1 to 2 mol, and preferably 1.0 to 1.2 mol with respect to 1 mol of compound (8).

The reaction may be performed in a solvent. There are no particular limitations on the solvent provided it is inactive against the reaction. Examples of the solvent are the same as the examples of the solvent used for producing compound (2). Although there are no particular limitations on the amount of the solvent, it is generally 1 to 100 ml with respect to 1 g of compound (8).

In addition, when performing a reaction with compound (4-2), it is preferable to perform in the presence of a base. Examples of the base include pyridine, triethylamine, potassium hydroxide and the like. The amount of the base is generally 1 to 2 mol with respect to 1 mol of compound (8).

The reaction temperature ranges from room temperature to the boiling point of the solvent. Although the reaction time varies according to the reaction scale, it is generally from minutes to hours.

b) A benzyloxyurea compound represented by formula (10) (hereinafter, may be referred to as "compound (10)") is produced by reacting compound (9) with compound (6), followed by debenzylating by catalytic reduction to produce an oxyurea compound represent by formula (11) (hereinafter, may be referred to as "compound (11)"). In formula (10) and (11), Q and $R^1$ are as defined above.

The amount of compound (6) is generally 1 to 2 mol, and preferably 1.0 to 1.2 mol with respect to 1 mol of compound (9).

The reaction may be performed in a solvent. There are no particular limitations on the solvent provided it is inactive against the reaction. Examples of the solvent are the same as the examples of the solvent used for producing compound (2). Although there are no particular limitations on the amount of the solvent, it is generally 1 to 100 ml with respect to 1 g of compound (9).

The reaction temperature ranges from −20° C. to the boiling point of the solvent. Although the reaction time varies according to the reaction scale, it is generally from minutes to hours.

Next, the debenzylating reaction is performed by catalytic reduction using a palladium catalyst or the like. Examples of the palladium catalyst include palladium black, palladium carbon and the like. The amount of palladium catalyst is generally 0.01 to 0.1 mol with respect to 1 mol of compound (10).

The reaction is performed in a solvent. There are no particular limitations on the solvent. Examples of the solvent are the same as the examples of the solvent used for producing compound (2). The examples of the solvent also include alcohol type solvents such as methanol, ethanol, n-propanol, and the like. Although there are no particular limitations on the amount of the solvent, it is generally 1 to 100 ml with respect to 1 g of compound (10).

The reaction temperature ranges from room temperature to the boiling point of the solvent. Although the reaction time varies according to the reaction scale, it is generally from minutes to hours.

c) A target compound (7) is produced by reacting compound (11) with an aryl compound represented by formula (12) (hereinafter, may be referred to as "compound (12)") in the presence of a base. In formula (12), X, n, and Cy are as defined above.

The amount of compound (12) is generally 1 to 2 mol, and preferably 1.0 to 1.2 with respect to 1 mol of compound (11).

Examples of the base include metal hydroxide such as lithium hydroxide, sodium hydroxide, potassium hydroxide, magnesium hydroxide, calcium hydroxide; metal alkoxide such as sodium methoxide, sodium ethoxide, potassium methoxide, potassium ethoxide, potassium t-butoxide; metal hydride such as sodium hydride, potassium hydride, calcium hydride; organic base such as triethylamine, diisopropyl ethylamine, pyridine, 1,8-diazabicyclo[5.4.0]undecene-7-ene (DBU), 1,4-diazabicyclo[2.2.2]octane. The amount of the base is generally 1 to 2 mol with respect to 1 mol of compound (11).

The reaction is performed in a solvent. There are no particular limitations on the solvent provided it is inactive against the reaction. Examples of the solvent are the same as the examples of the solvent used for producing compound (2). Although there are no particular limitations on the amount of the solvent, it is generally 1 to 100 ml with respect to 1 g of compound (11).

The reaction temperature ranges from −20° C. to the boiling point of the solvent. Although the reaction time varies according to the reaction scale, it is generally from minutes to hours.

After the reactions are completed, an ordinary post-treatment procedure, and if needed, known methods such as distillation, recrystallization or column chromatography, can be carried out to purify and isolate the target compound.

The structure of the target compound can be identified and confirmed by a known analysis such as IR spectroscopy, NMR spectroscopy, mass spectroscopy or elementary analysis.

[Pest Control Agent]

The aryloxyurea compound of the present invention or a salt thereof is effective to prevent various pests (including acari) or harmful organisms such as plant pathogens or the like.

[Acaricide]

The following provides an explanation of acaricide including the compound of the present invention as an active ingredient. Since the compound of the present invention has insecticidal action on adult insects, immature insects, larvae, insect eggs and the like, it can be used to prevent harmful organisms such as acari present on agricultural crops. In particular, the acaricide has a superior prevention effect against *acarus* present on agricultural crops, fruit trees, flowers and ornamental plants, and trees.

Examples of the acari targeted to prevent are shown below.

(1) Acaridida of Astigmata order:

(a) Acari belonging to Acaridae family, for example, *Rhizoglyphus echinopus* and *Rhizoglyphus robini* of *Rhizoglyphus* spp.; *Tyrophagus putrescentiae*, *Tyrophagus neiswanderi*, *Tyrophagus perniciosus* and *Tyrophagus similis* of *Tyrophagus* spp.; and others such as *Acarus siro*, *Aleuroglyphus ovatus*, *Mycetoglyphus fungivorus*;

(2) Actinedida of Prostigmata order (a) Acari belonging to Tetranychidae family, for example, *Bryobia praetiosa* and *Bryobia rubrioculus* of *Bryobia* spp.; for example, *Eotetranychus boreus*, *otetranychus geniculatus*, *Eotetranychus pruni*, *Eotetranychus uncatus*, *Eotetranychus shii*, *Eotetranychus suginamensis*, *Eotetranychus celtis*, *Eotetranychus smithi*, *Eotetranychus asiaticus* and *Eotetranychus kankitus* of *Eotetranychus* spp.; for example, *Oligonychus mangiferus*, *Oligonychus perseae*, *Oligonychus pustulosus*, *Oligonychus karamatus*, *Oligonychus hondoensis*, *Oligonychus ilicis*, *Oligonychus ununguis*, *Oligonychus shinkajii* and *Oligonychus orthius* of *Oligonychus* spp.; for example, *Panonychus citri*, *Panonychus mori* and *Panonychus ulmi* of *Panonychus* spp.; for example, *Tetranychus viennensis*, *Tetranychus quercivorus*, *Tetranychus ludeni*, *Tetranychus phaselus*, *Tetranychus cinnabarinus*, *Tetranychus kanzawai* and *Tetranychus urticae* of *Tetranychus* spp.; *Aponychus corpuzae* and *Aponychus firmianae* of *Aponychus* spp.; *Sasanychus akitanus* and *Sasanychus pusillus* of *Sasanychus* spp.; *Shizotetranychus celarius*, *Shizotetranychus miscanthi*, *Shizotetranychus longus*, *Shizotetranychus schizopus* and *Shizotetranychus recki* of *Shizotetranychus* spp.; and others such as *Tuckerella pavoniformis*, *Tetranychina harti*, *Yezonychus sapporensis*;

(b) Acari belonging to Tenuipalpidae family, for example, *Brevipalpus lewisi*, *Brevipalpus russulus*, *Brevipalpus obovatus* and *Brevipalpus phoenicis* of *Brevipalpus* spp.; for example, *Tenuipalpus pacificus* and *Tenuipalpus zhizhilashviliae* of *Tenuipalpus* spp.; and others such as *Dolichotetranychus floridanus*;

(c) Acari belonging to Eriophyidae family, for example, *Aceria diospyri*, *Aceria ficus*, *Aceria japonica*, *Aceria kuko*, *Aceria paradianthi*, *Aceria tiyingi*, *Aceria tulipae* and *Aceria zoysiea* of *Aceria* spp.; for example, *Eriophyes chibaensis* and *Eriophyes emarginatae* of *Eriophyes* spp.; for example, *Aculops lycopersici* and *Aculops pelekassi* of *Aculops* spp.; for example, *Aculus fockeui*, *Aculus schlechtendali*, which belong *Aculus* spp.; and others such as *Colomerus vitis*, *Calepitrimerus vitis*, *Phyllocoptruta citri*, *Paracalacarus podocarpi*, *Calacarus carinatus*, *Acaphylla theavagrans*, *Paraphytoptus kikus*, *Epitrimerus pyri*;

(d) Acari belonging to Transonemidae family, for example, *Tarsonemus bilobatus* and *Tarsonemus waitei* of *Tarsonemus* spp.; others such as *Phytonemus pallidus*, *Polyphagotarsonemus latus*;

(e) Acari belonging to Penthaleidae family, for example, *Penthaleus erythrocephalus* and *Penthaleus major* of *Penthaleus* spp.;

In addition, the acaricide of the present invention has a superior prevention effect against *acarus* parasitic in animals. Examples of the *acarus* parasitic in animals include those *acarus*, which are parasitic in the back, armpit, underbelly, and inner thigh of the animals being hosts (host animal) to obtain nutritional sources such as blood, dandruff from the animals to live. Examples of the host animals include dogs, cats, mice, rats, hamsters, guinea pigs, squirrels, rabbits, ferrets; pet birds (for example, pigeon, parrot, magpie, java sparrow, parakeet, bengalee, canary); cows, horses, pigs, sheep, goats; poultry (for example, ducks, chickens, quails, gooses); bees (for example, *apis mellifera*, Japanese honey bee); and the like.

Examples of the acari targeted to prevent are shown below.

(1) Mite of Mesostigmata order (a) Acari belonging to Dermanyssidae family, for example, *Dermanyssus gallinae*;

(b) Acari belonging to Macronyssidae family, for example, *Ornithonyssus sylviarum*, *Ornithonyssus bursa* and *Ornithonyssus bacoti* of *Ornithonyssus* spp.;

(c) Acari belonging to Laelapidae family, for example, *Laelaps echidninus* and *Laelaps jettmari* of *Laelaps* spp.; *Tropilaelaps clarae*;

(d) Acari belonging to Varroidae family, for example, *Varroa destructor*, *Varroa jacobsoni* and *Varroa underwoodi* of *Varroa* spp.;

(2) Tick of Metastigmata order (a) Acari belonging to Argasidae family, for example, *Argas persicus* and *Argas reflexus* of *Argas* spp.; for example, *Ornithodoros moubata*, which belongs to *Ornithodoros* spp.;

(b) Acari belonging to Ixodidae family, for example, *Haemaphysalis concinna*, *Haemaphysalis punctata*, *Haemaphysalis cinnabarina*, *Haemaphysalis otophila*, *Haemaphysalis leachi*, *Haemaphysalis longicornis*, *Haemaphysalis mageshimaensis*, *Haemaphysalis yeni*, *Haemaphysalis campanulata*, *Haemaphysalis pentalagi*, *Haemaphysalis flava*, *Haemaphysalis megaspinosa*, *Haemaphysalis japonica* and *Haemaphysalis douglasi* of *Haemaphysalis* spp.; for example, *Amblyomma americanum*, *Amblyomma variegatum*, *Amblyomma maculatum*, *Amblyomma hebraeum*, *Amblyomma cajennense* and *Amblyomma testudinarium* of *Amblyomma* spp.; for example, *Ixodes ricinus*, *Ixodes hexagonus*, *Ixodes canisuga*, *Ixodes pilosus*, *Ixodes rubicundus*, *Ixodes scapularis*, *Ixodes holocyclus*, *Ixodes ovatus*,

*Ixodes persulcatus* and *Ixodes nipponensis* of *Ixodes* spp.; for example, *Rhipicephalus (Boophilus) microplus), Rhipicephalus (Boophilus) decoloratus), Rhipicephalus (Boophilus) annulatus), Rhipicephalus (Boophilus) calceratus)*, which are belong to *Boophilus* spp.; for example, *Rhipicephalus evertsi, Rhipicephalus sanguineus, Rhipicephalus bursa, Rhipicephalus appendiculatus, Rhipicephalus capensis, Rhipicephalus turanicus* and *Rhipicephalus zambeziensis* of *Rhipicephalus* spp.; for example, *Dermacentor marginatus, Dermacentor reticulatus, Dermacentor pictus, Dermacentor albipictus, Dermacentor andersoni* and *Dermacentor variabilis* of *Dermacentor* spp.;

(3) Acaridida of Astigmata order (a) Acari belonging to Psoroptidae family, for example, *Psoroptes ovis, Psoroptes cuniculi, Psoroptes equi*, which are *Psoroptes* spp.; for example, *Chorioptes bovis*, which belongs to *Chorioptes* spp.; *Otodectes cynotis*, which belongs to *Otodectes* spp.;

(b) Acari belonging to Sarcoptidae family, for example, *Sarcoptes scabiei, Sarcoptes canis, Sarcoptes bovis, Sarcoptes ovis, Sarcoptes rupicaprae, Sarcoptes equi* and *Sarcoptes suis* of *Sarcoptes* spp.; for example, *Notoedres cati*, which belongs to *Notoedres* spp.;

(c) Acari belonging to Knemidokoptidae family, for example, *Knemidokoptes mutans*, which belongs to *Knemidokoptes* spp.;

(4) Actinedida of Prostigmata order (a) Acari belonging to Demodixidae family, for example, *Demodex canis, Demodex bovis, Demodex ovis, Demodex caprae, Demodex equi, Demodex caballi, Demodex suis* and *Demodex cati* of *Demodex* spp.;

(b) Acari belonging to Trombiculidae family, for example, *Trombicula alfreddugesi* and *Trombicula akamushi* of *Trombicula* spp.;

(c) Acari belonging to *Tarsonemidae* family, for example, *Acarapis woodi*, which belongs to *Acarapis* spp.;

(Pest Control Agent)

Furthermore, the compound of the present invention may be used to prevent harmful organisms such as pests other than acari present on agricultural crops, sanitary pests, stored grain pests, clothes pests and household pests.

Examples of the pests targeted to prevent are shown below.

(1) Lepidopteran pests, for example, *Spodoptera litura, Mamestra brassicae, Agrotis ipsilon, Autographa nigrisigna, Plutella xylostella, Adoxophyes honmai, Homona magnanima, Carposina sasakii, Grapholitha molesta, Phyllocnistis citrella, Caloptilia theivora, Phyllonorycter ringoniella, Lymantria dispar, Euproctis pseudoconspersa, Chilo suppressalis, Cnaphalocrocis medinalis, Ostrinia nubilalis, Hyphantria cunea, Cadra cautella, Heliothis* spp., *Helioverpa, Agrotis* spp., *Tinea translucens, Cydia pomonella, Pectinophora gossypiella*, or the like;

(2) Hemipteran pests, for example, *Myzus persicae, Aphis gossypii, Lipaphis erysimi, Rhopalosiphum padi, Riptortus clavatus, Acrosternum hilare, Unaspis yanonensis, Pseudococcus comstocki, Trialeurodes vaporariorum, Bemisia tabaci, Bemisia argentifolii, Psylla pyricola, Stephanitis nashi, Nilaparvata lugens, Laodelphax stratella, Sogatella furcifera, Nephotettix cincticeps*, or the like;

(3) Coleopteran pests, for example, *Phyllotreta striolata, Aulacophora indica, Leptinotarsa decemlineata, Lissorhoptrus oryzophilus, Sitophilus oryzae, Callosobruchus chinensis, Popillia japonica, Anomala rufocuprea, Diabrotica* spp., *Lasioderma serricorne, Lyctus brunneus, Monochamus alternatus, Anoplophora malasiaca, Agriotes* spp., *Epilachna vigintioctomaculata, Tenebroides mauritanicus, Anthonomus grandis*, or the like;

(4) Dipteran pests, for example, *Bactrocera cucurbitae, Bactrocera dorsalis, Delia platura, Hydrellia griseola, Drosophila melanogaster*, or the like;

(5) Thysanopteran pests, for example, *Thrips palmi, Scirtothrips dorsalis*, or the like;

(6) Hymenopteran pests, for example, *Monomorium pharaonis, Vespa simillima, Athalia rosae*, or the like;

(7) Orthopteran pests, for example, *Locusta migratoria*, or the like;

(8) Blattodea pests, for example, *Blattella germanica, Periplaneta fuligginosa, Periplaneta japonica, Periplaneta americana, Periplaneta australasiae*, or the like;

(9) Isopteran pests, for example, *Coptotermes formosanus, Reticulitermes speratus*, or the like;

(10) Plant parasitic nematodes, for example, *Meloidogyne incognita, Pratylenchus* spp., *Heterodera glycines, Aphelenchoides besseyi, Bursaphelenchus xylophilus*, or the like.

[Ectoparasiticide]

Furthermore, the compound of the present invention is superior in preventing ectoparasites other than *acarus* parasitic in animals.

Examples of the Phthiraptera targeted to prevent are shown below.

(1) Louse of Anoplura order (a) Louse belonging to Haematopinidae family, for example, *Haematopinus asini, Haematopinus eurysternus* and *Haematopinus suis* of *Haematopinus* spp.;

(b) Louse belonging to Linognathidae family, for example, *Linognathus setosus, Linognathus vituli, Linognathus ovillus, Linognathus oviformis, Linognathus pedalis* and *Linognathus stenopsis* of *Linognathus* spp.; for example, *Solenopotes capillatus* of *Solenopotes* spp.;

(2) Biting louse of Amblycera order (a) Biting louse belonging to Menoponidae family, for example, *Menacanthus stramineus, Menacanthus cornutus* and *Menacanthus pallidulus* of *Menacanthus* spp.; for example, *Menopon gallinae* belonging *Menopon* spp.;

(3) Biting louse of Ischnocera order (a) Biting louse belonging to Philopteridae family, for example, *Columbicola columbae* of *Columbicola* spp.; for example, *Cuclotogaster heterographus* of *Cuclotogaster* spp.; for example, *Goniodes dissimilis, Goniodes gigas, Goniodes gallinae* of *Goniodes* spp.; for example, *Lipeurus caponis* of *Lipeurus* spp.;

(b) Biting louse of Trichodectidae family, for example, *Bovicola bovis, Bovicola ovis, Bovicola limbata, Bovicola caprae* and *Bovicola equi* of *Bovicola* spp.; for example, *Trichodectes canis* of *Trichodectes* spp.; for example, *Felicola subrostrata* of *Felicola* spp.;

Examples of Siphonaptera are shown below.

(a) Flea belonging to Tungidae family, for example, *Tunga penetrans* of *Tunga* spp.;

(b) Flea belonging to Pulicidae family, for example, *Ctenocephalides canis* and *Ctenocephalides felis* of *Ctenocephalides* spp.; for example, *Archaeopsylla erinacei* of *Archaeopsylla* spp.; for example, *Xenopsylla cheopis* of *Xenopsylla* spp.; for example, *Pulex irritans* of *Pulex* spp.; for example, *Echidnophaga gallinacea* of *Echidnophaga* spp.;

(c) Flea belonging to Ceratophyllidae family, for example, *Ceratophyllus gallinae* and *Ceratophyllus anisus* of *Ceratophyllus* spp.; for example, *Nosopsyllus fasciatus* of *Nosopsyllus* spp.;

(d) Flea of Leptopsyllidae family, for example, *Leptopsylla segnis* of *Leptopsylla* spp.;

Examples of the exoparasite targeted to prevent also include Hemiptera.

Examples of the Hemiptera are shown below.

(a) Insect belonging to Cimicidae family, for example, *Cimex lectularius* of *Cimex* spp.;

(b) Insect belonging to Reduviidae family, and Triatominae, for example, *Panstrongylus* spp.; for example, *Rhodnius prolixus* of *Rhodnius* spp.; for example, *Triatoma infestans* of *Triatoma* spp.;

The ectoparasiticide of the present invention is also effective for preventing Diptera pest of biting insects (chewing fly, blood-sucking adult fly, larva of mobile diptera, gusano of parasitic fly).

Examples of the Diptera are shown below.

(1) Nematocera order (a) Mosquito belonging to Culicidae family, for example, *Culex quinquefasciatus, Culex pipiens pallens, Culex tarsalis, Culex pipiens molestus, Culex pipiens fatigans, Culex tritaeniorhynchus summorosus* of *Culex* spp.; *Armigeres subalbatus* of *Armigeres* spp.; for example, *Anopheles gambiae, Anopheles maculipennis, Anopheles sinensis, Anopheles lesteri* of *Anopheles* spp.; for example, *Aedes aegypti, Aedes albopictus, Aedes taeniorhynchus, Aedes togoi, Aedes vexans nipponii* of *Aedes* spp.;

(b) Black fly belonging to Simuliidae family, for example, *Simulium reptans, Simulium ornatum, Simulium venustum, Simulium salopiense* of *Simulium* spp.; for example, *Prosimulium yezoense* of *Prosimulium* spp.;

(c) Punkie belonging to Ceratopogonidae family, for example, *Culicoides arakawae, Culicoides pictimargo, Culicoides kibunensis, Culicoides homotomus, Culicoides oxystoma, Culicoides nipponensis, Culicoides punctatus, Culicoides maculatus, Culicoides matsuzawai* of *Culiodes* spp.;

(2) Brachycera order (a) Fly belonging to Tabanidae family, for example, *Tabanus bromius, Tabanus spodopterus, Tabanus atratus, Tabanus sudeticus, Tabanus trigonus, Tabanus chrysurus, Tabanus trigeminus, Tabanus fulvimedioides* and *Tabanus iyoensis* of *Tabanus* spp.; for example, *Chrysops caecutiens, Chrysops relictus, Chrysops suavis, Chrysops japonicus* of *Chrysops* spp.;

(b) Fly belonging to Muscidae family, for example, *Musca domestica, Musca bezzii, Musca hervei, Musca conducens* and *Musca stabulans* of *Muscina* spp.; for example, *Stomoxys calcitrans* of *Stomoxys* spp.; for example, *Haematobia irritans, Haematobia irritans exigua* and *Haematobia stimulans* of *Haematobia* spp.; *Fannia canisularis* of *Fannia* spp.;

(c) *Glossina* spp. belonging to Glossinidae family;

(d) Fly belonging to Hippoboscidae family, for example, *Melophagus ovinus* of *Melophagus* spp.;

(e) Fly belonging to Calliphoridae family, for example, *Calliphora lata* of *Calliphora* spp.; for example, *Lucilia (Phaenicia) cuprina, Lucilia (Phaenicia) sericata* and *Lucilia illustris* of *Lucilia* spp.; for example, *Chrysomya hominivorax, Chrysomya chloropyga* and *Chrysomya bezziana* of *Chrysomyia*. spp.;

(f) Fly belonging to Oestridae family, for example, *Cuterebra* spp. of Cuterebrinae family; for example, *Hypoderma bovis* and *Hypoderma lineatum* of *Hypoderma* spp. of Hypodermatinae family; for example, *Gasterophilus intestinalis, Gasterophilus haemorroidalis, Gasterophilus inermis, Gasterophilus nasalis, Gasterophilus nigricornis* and *Gasterophilus pecorum* of *Gasterophilus* spp. of Gasterophilinae family; for example, *Oestrus ovis* of *Oestrus* spp. of Oestrinae family;

[Fungicide]

The following provides an explanation of fungicide including the compound of the present invention as an active ingredient. The compound of the present invention may be used to prevent plant diseases derived from a wide range of types of fungi, such as fungi belonging to Oomycetes, Ascomycetes, Deuteromycetes or Basidiomycetes, because it has a superior fungicidal action.

The plant diseases targeted to prevent are shown below.
Sugar Beets:
Cercospora leaf spot (*Cercospora beticola*)
Aphanomyces root rot (*Aphanomyces cochlloides*)
Root rot (*Thanatephorus cucumeris*)
Leaf blight (*Thanatephorus cucumeris*) or the like
Peanuts:
Brown leaf spot (*Mycosphaerella arachidis*)
Black leaf blight (*Mycosphaerella berkeleyi*) or the like
Cucumbers:
Powdery mildew (*Sphaerotheca fuliginea*)
Downy mildew (*Pseudoperonospora cubensis*)
Gummy stem blight (*Mycosphaerella melonis*)
*Fusarium* wilt (*Fusarium oxysporum*)
*Sclerotinia* rot (*Sclerotinia sclerotiorum*)
Gray mold (*Botrytis cinerea*)
Anthracnose (*Colletotrichum obriculare*)
Scab (*Cladosporium cucumerinum*)
*Corynespora* leaf spot (*Corynespora cassicola*)
Damping-off (*Pythium debaryanum, Rhizoctonia solani* Kuhn)
Bacterial spot (*Pseudomonas syringae* pv. *Lecrymans*) or the like
Tomatoes:
Gray mold (*Botrytis cinerea*)
Leaf mold (*Cladosporium fulvum*)
Late blight (*Phytophthora infestans*) or the like
Eggplants:
Gray mold (*Botrytis cinerea*)
Black rot (*Corynespora melongenae*)
Powdery mildew (*Erysiphe cichoracearum*)
Leaf mold (*Mycovellosiella nattrassii*) or the like
Strawberries:
Gray mold (*Botrytis cinerea*)
Powdery mildew (*Sphaerotheca humuli*)
Anthracnose (*Colletotrichum acutatum, Colletotrichum fragariae*)
*Phytophthora* rot (*Phytophthora cactorum*) or the like
Onions:
Neck rot (*Botrytis allii*)
Gray mold (*Botrytis cinerea*)
Leaf blight (*Botrytis squamosa*)
Downy mildew (*Peronospora destructor*)
Cabbage:
Clubroot (*Plasmodiophora brassicae*)
Bacterial soft rot (*Erwinia carotovora*)
Downy mildew (*Peronospora parasitica*) or the like
Kidney beans:
Stem rot (*Sclerotinia sclerotiorum*)
Gray mold (*Botrytis cinerea*) or the like
Apples:
Powdery mildew (*Podosphaera leucotricha*)
Scab (*Venturia inaequalis*)
Blossom blight (*Monilinia mali*)
Fruit spot (*Mycosphaerella pomi*)
Valsa canker (*Valsa mali*)

Alternaria blotch (*Alternaria mali*)
Rust (*Gymnosporangium yamadae*)
Ring rot (*Botryosphaeria berengeriana*)
Anthracnose (*Glomerella cingulata, Colletotrichum acutatum*)
Blotch (*Diplocarpon mali*)
Fly speck (*Zygophiala jamaicensis*)
Sooty blotch (*Gloeodes pomigena*) or the like
Persimmons:
Powdery mildew (*Phyllactinia kakicola*)
Anthracnose (*Gloeosporium kaki*)
Angular leaf spot (*Cercospora kaki*) or the like
Peaches:
Brown rot (*Monilinia fructicola*)
Scab (*Cladosporium carpophilum*)
*Phomopsis* rot (*Phomopsis* sp.) or the like
Cherries:
Brown rot (*Monolinia fructicola*) or the like
Grapes:
Gray mold (*Botrytis cinerea*)
Powdery mildew (*Uncinula necator*)
Ripe rot (*Glomerella cingulata, Colletotrichum acutatum*)
Downy mildew (*Plasmopara viticola*)
Anthracnose (*Elsinoe ampelina*)
Leaf blight (*Pseudocercospora vitis*)
Black rot (*Guignardia bidwellii*) or the like
Pears:
Scab (*Venturia nashicola*)
Rust (*Gymnosporangium asiaticum*)
Black spot (*Alternaria kikuchiana*)
Ring rot (*Botryosphaeria berengeriana*)
Powdery mildew (*Phyllactinia mali*) or the like
Tea:
Gray blight (*Pestalotia theae*)
Anthracnose (*Collectotrichum theae-sinensis*) or the like
Citrus:
Scab (*Elsinoe fawcetti*)
Blue mold (*Penicillium italicum*)
Common green mold (*Penicillium digitatum*)
Gray mold (*Botrytis cinerea*)
Melanose (*Diaporthe citri*)
Canker (*Xanthomonas campestris* pv. *Citri*) or the like
Wheat:
Powdery mildew (*Erysiphe graminis* f. sp. *tritici*)
*Fusarium* blight (*Gibberella zeae*)
Leaf rust (*Puccinia recondita*)
Browning root rot (*Pythium iwayamai*)
Snow mold (*Monographella nivalis*)
Eye spot (*Pseudocercosporella herpotrichoides*)
Speckled leaf blotch (*Septoria tritici*)
Glume blotch (*Leptosphaeria nodorum*)
*Typhula* snow blight (*Typhula incarnata*)
*Sclerotinia* snow blight (*Myriosclerotinia borealis*)
Take-all (*Gaeumanomyces graminis*) or the like
Barley:
Stripe (*Pyrenophora graminea*)
Leaf blotch (*Rhynchosporium secalis*)
Loose smut (*Ustilago tritici, U. nuda*) or the like
Rice:
Blast (*Pyricularia oryzae*)
Sheath blight (*Rhizoctonia solani*)
Bakanae disease (*Gibberella fujikuroi*)
Brown spot (*Cochliobolus niyabeanus*)
Seedling blight (*Pythium graminicolum*)
Bacterial leaf blight (*Xanthomonas oryzae*)
Bacterial seedling blight (*Burkholderia plantarii*)
Bacterial brown stripe (*Acidovorax avanae*)
Bacterial grain rot (*Burkholderia glumae*) or the like
Tobacco:
*Sclerotinia* stem-rot (*Sclerotinia sclerotiorum*)
Powdery mildew (*Erysiphe cichoracearum*) or the like
Tulips:
Gray mold (*Botrytis cinerea*) or the like
Bent grass:
*Sclerotinia* snow blight (*Sclerotinia borealis*)
Bacterial shoot blight (*Pythium aphanidermatum*) or the like
Orchard grass:
Powdery mildew (*Erysiphe graminis*) or the like
Soybeans:
Purple stain (*Cercospora kikuchii*)
Downy mildew (*Peronospora Manshurica*)
*Phytophthora* root and stem rot (*Phytophthora sojae*) or the like
Potatoes, tomatoes:
Late blight (*Phytophthora infestans*) or the like The compound of the present invention causes little chemical damage, demonstrates low levels of toxicity in fish and warm-blooded animals, and is a compound having a particularly high degree of safety.

The pest control agent of the present invention contains as an active ingredient at least one type of compound selected from the compounds of the present invention.

In addition, although the pest control agent of the present invention may only contain the compound of the present invention, it may also contain carriers such as a solid carrier, liquid carrier or gaseous carrier. In addition, the pest control agent of the present invention may have the compound of the present invention impregnated in a base material such as a porous ceramic plate or non-woven fabric. Moreover, a surfactant or other adjunct may be added as necessary.

The pest control agent according to the present invention can be formulated into a form able to be typically adopted by agricultural chemicals, namely in the form of a water-dispersible powder, granules, powder, emulsion, water-soluble powder, suspension, granular water-dispersible powder, flowable preparation, microcapsules, aerosol, fog, heat transpiration agent, fumigant or poison bait.

Examples of the additives and carriers used when formulating a solid preparation include vegetable powders such as soybean powder or flour, mineral fine powders such as diatomaceous earth, apatite, plaster, talc, bentonite, pyrophyllite or clay; and organic and inorganic compounds such as sodium benzoate, urea or sodium sulfate.

Examples of the solvents used when formulating liquid preparations include kerosene, xylene, and petroleum-based aromatic hydrocarbon, cyclohexane, cyclohexanone, dimethylformamide, dimethylsulfoxide, alcohols, acetone, trichloroethylene, methyl isobutyl ketone, mineral oils, vegetable oils and water.

Examples of the gaseous carriers used when formulating propellants include butane gas, LPG, dimethyl ether and carbon dioxide gas.

Examples of the base materials of poison bait include bait components such as grain powder, vegetable oil, sugar or crystalline cellulose, antioxidants such as dimethylhydroxytoluene or nordihydroguaiaretic acid, preservatives such as dehydroacetic acid, accidental swallowing preventives for small children and pets such as cayenne pepper powder, insect-attracting fragrances such as cheese fragrance or onion fragrance.

A surfactant can be added according to need in order to obtain a uniform and stable form during formulation. There are no limitations on the surfactants to be added. Examples of surfactants include nonionic surfactants such as polyoxyethylene alkyl phenyl ethers, polyoxyethylene alkyl ethers, polyoxyethylene higher fatty acid esters, polyoxyethylene sorbitan higher fatty acid esters or polyoxyethylene tristyryl phenyl ethers; sulfate esters of polyoxyethylene alkyl phenyl ethers, alkyl benzene sulfonate, higher fatty alcohol sulfate, alkylnaphthalene sulfonates, polycarboxylates, lignin sulfonates, formaldehyde condensates of alkylnaphthalene sulfonates and isobutylene-maleic anhydride copolymers.

The amount of the compound of the present invention contained in the preparation is preferably 0.01 to 90% by weight, and more preferably 0.05 to 85% weight.

The water-dispersible powder, emulsion, flowable preparation, water-soluble powder, granular water-dispersible powder, which are obtained in this manner can be prepared in the form of solution, suspension or emulsion and diluted with water to a prescribed concentration to spray onto plants or soil, or in the case of using it in the form of powder or granules, it can be sprayed directly onto plants or soil.

In addition, in the case of using it as an acaricide for epidemic prevention, a preparation that is supplied in the form of oil solution, aerosol, fog, poison bait or miticidal sheet can be directly used.

In addition, in tyre case of using the pest control agent of the present invention to prevent animal parasitic acari of livestock such as cows or pigs and pets such as dogs or cats, the compound of the present invention can be used at a ratio of 0.01 mg to 1000 mg per 1 kg of host animal.

An acaricide for preventing acari can be applied using a known veterinary method. Examples of such methods include methods in which the acaricide is administered to an animal by tablet, capsule, immersion liquid, food additive, suppository or injection (intramuscular, subcutaneous, intravenous or intraabdominai injection) when administered for the purpose of systemic control, methods in which an oily or aqueous liquid preparation is administered by spraying, pouring on or spotting on when administered for the purpose of non-systemic control, and methods in which the acaricide is mixed with a resin and the kneaded product is molded into a suitable shape such as that of a collar or ear tag which is then attached to the animal.

The pest control agent of the present invention can be mixed or combined with fungicides, other insecticides or acaricides, nematocides, soil pesticides, plant regulators, synergists, fertilizers, soil improvers or animal feeds and the like.

The following lists typical examples of fungicides, other insecticides or acaricides, nematocides, soil pesticides and plant regulators able to be used by mixing with the pest control agent of the present invention.

Examples of insecticides, acaricides, nematocides and soil pesticides include:

(1) organic (thio)phosphate-based: such as acephate, azamethiphos, azinphos-methyl, azinphos-ethyl, bromophos-ethyl, bromfenvinphos, BRP, chlorpyriphos, chlorpyriphos-methyl, chlorpyrifos-ethyl, chlorfenvinphos, cadusafos, carbophenothion, chlorethoxyfos, chlormephos, coumaphos, cyanofenphos, cyanophos, CYAP, diazinon, dichlorvos, dicrotophos, dimethoate, disulfoton, demeton-S-methyl, dimethylvinfos, demeton-S-methyl sulphone, dialifos, diazinon, dichlofenthion, dioxabenzofos, disulfoton, ethion, ethoprophos, etrimfos, EPN, fenamiphos, fenitrothion, fenthion, fensulfothion, flupyrazofos, fonofos, formothion, fosmethilan, heptenophos, isazophos, iodofenphos, isofenphos, isoxathion, iprobenfos, malathion, mevinphos, methamidophos, methidathion, monocrotophos, mecarbam, methacrifos, naled, omethoate, oxydemeton-metyl, paraoxon, parathion, parathion-methyl, phenthoate, phosalone, phosmet, phosphamidon, phorate, phoxim, pirimiphos-methyl, pirimiphos-ethyl, profenofos, prothiofos, fosthiazete, phosphocarb, propaphos, propetamphos, prothoate, pyridafenthion, pyraclofos, quinalphos, salithion, sulprofos, sulfotep, tetrachlorvinphos, terbufos, triazophos, trichlorfon, tebupirimfos, temephos, thiomethon, vamidothion, pyraclofos;

(2) carbamate-based: alanycarb, aldicarb, bendiocarb, benfuracarb, carbaryl, carbofuran, carbosulfan, fenoxycarb, fenothiocarb, methiocarb, methomyl, oxamyl, pirimicarb, propoxur, thiodicarb, triazamate, ethiofencarb, fenobucarb, MIPC, MPMC, MTMC, pyridafenthion, furathiocarb, XMC, aldoxycarb, allyxycarb, aminocarb, bendiocarb, bufencarb, butacarb, butocarboxim, butoxycarboxim, cloethocarb, dimetilan, formetanate, isoprocarb, metam-sodium, metolcarb, thiofanox, trimethacarb, xylycarb;

(3) pyrethroid-based: allethrin, bifenthrin, cyfluthrin, β-cyfluthrin, cyhalothrin, lambdacyhalothrin, cyphenothrin, cypermethrin, alphacypermethrin, betacypermethrin, zeta-cypermethrin, deltamethrin, esfenvalerate, etofenprox, fenpropathrin, fenvalerate, imiprothrin, permethrin, prallethrin, pyrethrin, pyrethrin I, pyrethrin II, resmethrin, silafluofen, fluvalinate, tefluthrin, tetramethrin, tralomethrin, transfluthrin, profluthrin, dimefluthrin, acrinathrin, cycloprothrin, halfenprox, flucythrinate, bioallethrin, bioethanomethrin, biopermethrin, bioresmethrin, transpermethirn, empenthrin, fenfluthrin, fenpirithrin, flubrocythrinate, lufenoprox, flumethrin, metofluthrin, phenothrin, protrifenbute, pyresmethrin, terallethrin;

(4) growth regulators:

(a) chitin synthesis inhibitors: chlorfluazuron, diflubenzuron, flucycloxuron, flufenoxuron, hexaflumuron, lufenuron, novaluron, teflubenzuron, triflumuron, bistrifluron, nobifumuron, buprofezin, hexythiazox, etoxazole, clofentezine, fluazuron, penfluron;

(b) ecdysone antagonists: halofenozide, methoxyfenozide, tebufenozide, chromafenozide, azadirachtin;

(c) juvenile hormone-like substances: pyriproxyfen, methoprene, diofenolan, epofeneonane, hydroprene, kinoprene, triprene;

(d) lipid biosynthesis inhibitors: spirodiclofen, spiromesifen, spirotetramat, flonicamid;

(5) nicotine receptor agonist/antagonist compounds: acetamiprid, clothianidin, dinotefuran, imidacloprid, nitenpyram, thiacloprid, thiamethoxam, nithiazine, nicotine, bensultap, cartap;

(6) GABA antagonist compounds:

(a) acetochlor, ethiprole, fipronil, vaniliprole, pyrafluprole, pyriprole;

(b) organochlorine compound: camphechlore, chlordane, endosulfan, HCH, γ-HCH, heptachlor, methoxychlor;

(7) macrocyclic lactone insecticides: abamectin, emamectin, milbemectin, lepimectin, spinosad, ivermectin, seramectin, doramectin, epinomectin, moxidectin;

(8) METI I compounds: fenazaquin, pyridaben, tebufenpyrad, tolfenpyrad, flufenirim, hydramethylnon, fenpyroxymate, pyrimidifen, dicofol;

9) METI II and III compounds: acequinocyl, fluacrypyrim, rotenone;

(10) uncoupling agent compounds: chlorfenapyr, dinobuton, dinocap, DNOC;

11) oxidative phosphorylation inhibitor compounds: cyhexitin, diafenthiuron, fenbutatin oxide, propargite, azocyclotin;

(12) molting disruption compounds: cyromazine;

(13) mixed function oxidase inhibitor compounds: piperonyl butoxide;

(14) sodium channel blocker compounds: indoxacarb, metaflumizone;

(15) microbial pesticides: BT agents, insect pathogen viral agents, insect pathogen fungal agents, nematode pathogen fungal agents, bacillus, beauveria bassiana, metarhizium anisopliae, paecilomyces, thuringiensin, verticillium;

(16) latrophilin receptor agonist: depsipeptide, cyclodepsipeptide, 24-membered cyclodepsipeptide, emodepside;

(17) octopamine agonist: amitraz;

(18) ryanodine derivative agonist: flubendiamide, chlorantraniliprole, cyantraniliprole;

(19) magnesium-stimulated ATPase inhibitor: thiocyclarm, thiosultap, nereistoxin;

(20) antifeedant: pymetrozine;

(21) acari growth inhibitor: clofentezine, etoxazole;

(22) other compounds: benclothiaz, bifenazate, pyradalyl, sulfur, cyenopyrafen, cyflumetofen, amidoflumet, tetradifon, chlordimeform, 1,3-dichloropropene, DCIP, phenisobromolate, benzomate, methaldehyde, spinetoram, pyrifluquinzaon, benzomate, bromopropylate, quinomethionate, chlorobenzilate, chloropicrin, chlothiazoben, dicyclanil, fenoxacrim, fentrifanil, flubenzimine, fluphenazine, gossyplure, japonilure, metoxadiazone, oil, potassium oleate, sulfluramid, tetrasul, triarathene;

Fungicides:

(1) benzimidazole-based: benomyl, carbendazim, fuberidazole, thiabendazole, methyl thiophanate or the like;

(2) dicarboxyimide-based fungicides: chlozolinate, iprodione, procymidone, vinclozolin or the like;

(3) DMI fungicides: imdazalil, oxpoconazole, pefurazoate, prochloraz, triflumizole, triforine, pyrifenox, fenarimol, nuarimol, azaconazole, bitertanol, bromconazole, cyproconazole, difenoconazole, diniconazole, epoxyconazole, fenbuconazole, fluquinconazole, flusilazole, flutriafol, hexaconazole, imibenconazole, ipuconazole, metconazole, myclobutanil, penconazole, propiconazole, prothioconazole, simeconazole, tebuconazole, tetraconazole, triadimefon, triadimenol, triticonazole, etaconazole, furconazole-cis or the like;

(4) phenylamide-based: benalaxyl, furalaxyl, metalaxyl, metalaxyl-M, oxadixyl, ofurace or the like;

(5) amine-based: aldimorph, dodemorph, fenpropimorph, tridemorph, fenpropidine, piperalin, spiroxamine or the like;

(6) phosphothiolate-based: EDDP, iprobenfos, pyrazophos or the like;

(7) dithiolane-based: isoprothiolane or the like;

(8) carboxamide-based: benodanil, boscalid, carboxin, fenfuran, flutolanil, furametpyr, mepronil, oxycarboxin, penthiopyrad, thifluzamide or the like;

(9) hydroxy(2-amino)pyrimidine-based: bupirimate, dimethirimol, ethirimol or the like;

(10) AP fungicides (anilinopyrimidines-based): cyprodinil, mepanipyrim, pyrimethanil or the like;

(11) N-phenylcarbamate-based: diethofencarb or the like;

(12) QoI fungicides (Qo inhibitor-based): azoxystrobin, picoxystrobin, pyraclostrobin, kresoxim-methyl, trifloxystrobin, dimoxystrobin, metominostrobin, orysastrobin, famoxadone, fluoxastrobin, fenamidone, metominofen or the like;

(13) PP fungicides (phenylpyrrole-based): fenpiconil, fludioxonil or the like;

(14) quinoline-based: quinoxyfen or the like;

(15) AH fungicides (aromatic hydrocarbon-based): biphenyl, chloroneb, dichloran, quintozene, tecnazene, tolclofos-methyl or the like;

(16) MBI-R-based: fthalide, pyroquilon, tricyclazole or the like;

(17) MBI-D-based: carpropamid, diclocymet, fenoxanil or the like;

(18) SBI agents: fenhexamid, pyributicarb, terbinafine or the like;

(19) phenylureas: pencycuron or the like;

(20) Qil fungicides (Qi inhibitors): cyazofamid or the like;

(21) benzamide-based: zoxamide or the like;

(22) enopyranurone-based: blasticidin, mildiomycin or the like;

(23) hexopyranosyl-based: kasugamycin or the like;

(24) glucopyranosyl-based: streptomycin, validamycin or the like;

(25) cyanoacetoamide-based: cymoxanil or the like;

(26) carbamate-based: idocarb, propamocarb, prothiocarb, polycarbamate or the like;

(27) uncoupling agents: binapacryl, dinocap, ferimzone, fluazinam or the like;

(28) organic tin compounds: triphenyltin acetate, triphenyltin chloride, triphenyltin hydroxide or the like;

(29) phosphate esters: phosphonic acid, tolclofos-methyl, fosetyl or the like;

(30) phthalamide-based: tecloftalam or the like;

(31) benzotriazine-based: triazoxide or the like;

(32) benzene sulfonamide-based: flusulfamide or the like;

(33) pyridazinones: diclomezine or the like;

(34) CAA fungicide (carboxylic amide)-based: dimethomorph, flumorph, benthiavalicarb, iprovalicarb, mandipropamide or the like;

(35) tetracyclines: oxytetracycline or the like;

(36) thiocarbamate-based: methasulfocarb or the like; and,

(37) other compounds: etridiazole, polyoxins, oxolinic acid, hydroxyisoxazole, octinoline, silthiofam, diflumetorim, acibenzolar-s-methyl, probenazole, tiadinil, ethaboxam, cyflufenamid, proquinazid, metrafenone, fluopicolide, cupric hydroxide, organic copper, sulfur, ferbam, manzeb, maneb, metiram, propineb, thiuram, zineb, ziram, captan, captafol, folpet, chlorothalonil, dichlofluanid, tolylfluanid, dodine, guazatine, iminoctadine acetate, iminoctadine dodecylbenzene sulfonate, anilazine, dithianon, chloropicrin, dazomet, metam sodium salt, chinomethionat, cyprofuram, silthiofam, agrobacterium, fluoroimide.

Examples of the plant growth regulators include:

abscisic acid, indole butyric acid, uniconazole, ethychlozate, ethephon, cloxyfonac, chlormequat, chlorella extract, calcium peroxide, cyanamide, dichlorprop, gibberellin, daminozide, decyl alcohol, trinexapac-ethyl, mepiquat-chloride, paclobutrazol, paraffin wax, piperonyl butoxide, pyraflufen ethyl, flurprimidol, prohydrojasmon, prohexadione-calcium, benzylaminopurine, pendimethalin, forchlorfenuron, potassium hydrazide maleate, 1-naphthylacetoamide, 4-CPA, MCPB, choline, oxyquinoline sulfate, ethychlozate, butralin, 1-methylcyclopropene, aviglycine hydrochloride.

EXAMPLES

The following provides Examples to explain the present invention more specifically. However, the present invention is not limited to the following examples.

Example 1

(i) Production of 1-(3-bromo-5-chlorophenoxy)-3-(2-phenylpropan-2-yl)urea

[Chemical formula 18]

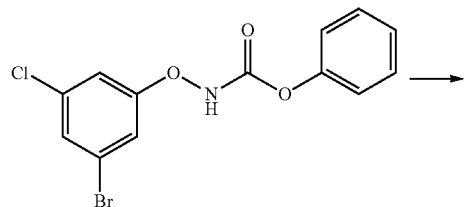

3.00 g of phenyl 3-bromo-5-chlorophenoxycarbamate was dissolved in 50 ml of tetrahydrofuran. The resulting solution was added to a mixture of 1.54 g of cumylamine and 1.15 g of triethylamine, followed by stirring for 5 hours, while being heated to reflux. The reaction solvent was then distilled off under reduced pressure. The resulting residue was partially purified by silica gel column chromatography (eluent: hexane:ethyl acetate=3:1). The resulting crude crystal was washed with hexane to obtain 1-(3-Bromo-5-chlorophenoxy)-3-(2-phenylpropan-2-yl)urea (2.89 g, yield: 86%).

The physical properties of 1-(3-bromo-5-chlorophenoxy)-3-(2-phenylpropan-2-yl)urea are shown below.

$^1$H-NMR (CDCl$_3$/TMS, δ(ppm)) 7.39-7.17 (m, 9H), 5.79 (s, 1H), 1.73 (s, 6H)

(ii) Production of 1-(3-bromo-5-chlorophenoxy)-1-ethyl-3-(2-phenylpropan-2-yl)urea (compound no. 1-24)

[Chemical formula 19]

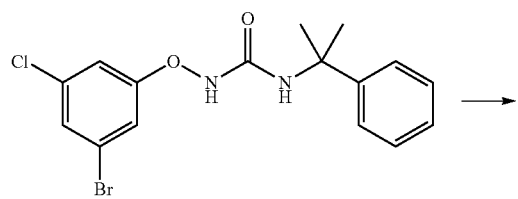

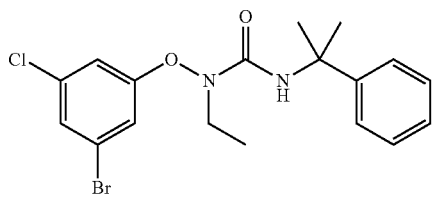

2.89 g of 1-(3-bromo-5-chlorophenoxy)-3-(2-phenylpropan-2-yl)urea was dissolved in 30 ml of N,N-dimethyl formamide. The resulting solution was added to a mixture of 5.18 g of potassium carbonate and 1.17 g of iodoethane, followed by stirring for one night at room temperature. Ethyl actate was then added to the susulting solution. The resulting mixture was washed with ammonium chloride, and the organic layer was dried with magnesium sulfate. After filtration, the solvent was distilled off. The resulting residues was purified by silica gel column chromatography (eluent: hexane:ethyl acetate=5:1) to obtain the target compound of 1-(3-bromo-5-chlorophenoxy)-1-ethyl-3-(2-phenylpropan-2-yl)urea (2.86 g, yield: 92%).

The physical properties of 1-(3-bromo-5-chlorophenoxy)-1-ethyl-3-(2-phenylpropan-2-yl)urea are shown below.

$^1$H-NMR (CDCl$_3$/TMS, δ(ppm)) 7.34-7.32 (m, 4H), 7.28-7.22 (m, 3H), 7.15 (t, 1H), 5.91 (s, 1H), 3.60 (q, 2H), 1.68 (s, 6H), 1.12 (t, 3H)

Examples of the compounds able to be obtained by the production method described above are shown in TABLES 1 to 4. TABLE 1 shows the substituents of the compounds represented by formula (a). TABLE 2 shows the substituents of the compounds represented by formula (b). TABLE 3 shows the substitutents of the compounds represented by formula (c). TABLE 4 shows the substituents of the compounds represented by formula (d). In addition, TABLES 1 to 4 show only a part of aryloxyurea compounds of the present invention. An ordinary skilled person can easily understand that other compounds which are not shown in this description, namely, the compounds which are substituted by various substituents complying with the purpose and scope of the present invention can also be obtained by the above-described method and can be used. In addition, the abbreviations described in the tables have the meanings as defined below:

[Chemical formula 20]

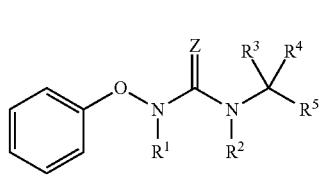

(a)

TABLE 1

$$\text{(X)}_n\text{-C}_6\text{H}_{4-n}\text{-O-N(R}^1\text{)-C(=Z)-N(R}^2\text{)-C(R}^3\text{)(R}^4\text{)(R}^5\text{)}$$

| No. | R¹ | R² | R³ | R⁴ | R⁵ | (X)n | Z | Melting Point (° C.) |
|---|---|---|---|---|---|---|---|---|
| 1-1 | Et | H | Me | Me | Me | 3-Br-6-Cl | O | 80-81 |
| 1-2 | Et | H | Me | Me | Me | 3-CF₃ | O | viscous oil |
| 1-3 | Et | H | Me | Me | Me | 3-Br-5-Cl | O | viscous oil |
| 1-4 | Et | H | Me | Me | Me | 2-Cl-5-(3-CF₃—Ph) | O | viscous oil |
| 1-5 | Et | H | Me | Me | Me | 3,5-Cl₂ | O | viscous oil |
| 1-6 | Et | H | Me | Me | Me | 3-OH-4-NO₂ | O | 82-83 |
| 1-7 | Et | H | Me | Me | Me | 4-Ac | O | 63-65 |
| 1-8 | Et | H | Me | Me | Me | 3-Cl-5-CN | O | viscous oil |
| 1-9 | Et | H | Me | Me | Me | 3-Cl-5-OMe | O | viscous oil |
| 1-10 | Et | H | Me | Me | Me | 3-Br-4,5-Cl₂ | O | 59-63 |
| 1-11 | Et | H | Me | Me | Me | 3-Cl-5-(4-Cl—Ph) | O | 95-97 |
| 1-12 | Et | H | Me | Me | Me | 3-Cl-5-(4-OMe—Ph) | O | viscous oil |
| 1-13 | Et | H | Me | Me | Me | 4-NO₂ | O | 92-94 |
| 1-14 | Et | H | Me | Me | Me | 3-Br-5-OMe | O | viscous oil |
| 1-15 | Et | H | Me | Me | Me | 3-Br-5-Me | O | viscous oil |
| 1-16 | Et | H | Me | Me | Me | 2,4-Cl₂ | O | viscous oil |
| 1-17 | Et | H | Me | Me | Me | 2,5-Me₂-4-NO₂ | O | 123-125 |
| 1-18 | Et | H | Me | Me | Me | 3-Br-5-CO₂Me | O | 124-126 |
| 1-19 | Et | H | Me | Me | Me | 2,3,5-Br₃ | O | viscous oil |
| 1-20 | Et | H | Me | Me | Me | 3,5-Br₂-4-Cl | O | 91-93 |
| 1-21 | Et | H | Me | Me | Me | 3,4,5-Br₃ | O | 86-88 |
| 1-22 | Et | H | Me | Me | Me | 3-Br-2-Cl | O | viscous oil |
| 1-23 | Et | H | Me | Me | Me | 3,5-Br₂-4-OMe | O | 87-89 |
| 1-24 | Et | H | Me | Me | Ph | 3-Br-5-Cl | O | 92-93 |
| 1-25 | Et | H | Me | Me | Ph | 3,4-Cl₂ | O | 74-76 |
| 1-26 | Et | H | Me | Me | Ph | 3-Br-5-CF₃ | O | 112-114 |
| 1-27 | Et | H | Me | Me | Ph | 3,5-Br₂ | O | 103-105 |
| 1-28 | Et | H | Me | Me | Ph | 3-Br-4,5-Cl₂ | O | 100-102 |
| 1-29 | Et | H | Me | Me | Ph | 3,5-Cl₂ | O | 91-93 |
| 1-30 | Et | H | Me | Me | Ph | 3-Br-5-F | O | 67-69 |
| 1-31 | Et | H | Me | Me | Ph | 3,5-F₂ | O | 94-96 |
| 1-32 | Et | H | Me | Me | Ph | 3-Br-5-CN | O | 108-110 |
| 1-33 | Et | H | Me | Me | Ph | 3-Br-5-NO₂ | O | 111-113 |
| 1-34 | Et | H | Me | Me | Ph | 3-Br-5-SO₂Me | O | 127-129 |
| 1-35 | Et | H | Me | Me | Ph | 3-Br-5-OMe | O | viscous oil |
| 1-36 | Et | H | Me | Me | Ph | 4-CF₃ | O | 112-114 |
| 1-37 | Et | H | Me | Me | Ph | 2,5-Me₂-4-NO₂ | O | 87-89 |
| 1-38 | Et | H | Me | Me | Ph | 2,3,5-Br₃ | O | 124-126 |
| 1-39 | Et | H | Me | Me | Ph | 3,4-Br₂ | O | 81-83 |
| 1-40 | Et | H | Me | Me | Ph | 3-Br-4-Cl | O | 89-91 |
| 1-41 | Et | H | Me | Me | Ph | 3,5-Br₂-4-Cl | O | 114-116 |
| 1-42 | Et | H | Me | Me | Ph | 3,4,5-Br₃ | O | 97-99 |
| 1-43 | Et | H | Me | Me | Ph | 3-Br-2-Cl | O | 67-69 |
| 1-44 | Et | H | Me | Me | Ph | 5-Br-2-Cl | O | 67-69 |
| 1-45 | Et | H | Me | Me | Ph | 3-Br-5-CO₂Me | O | 87-89 |
| 1-46 | Et | H | Me | Me | Ph | — | O | viscous oil |
| 1-47 | Et | H | Me | Me | Ph | 3-Cl | O | 69-71 |
| 1-48 | Et | H | Me | Me | Ph | 2-Cl | O | 50-52 |
| 1-49 | Et | H | Me | Me | Ph | 2,6-Cl₂ | O | 153-155 |
| 1-50 | Et | H | Me | Me | CH=N—OMe | 3-Br-5-Cl | O | viscous oil |
| 1-51 | Et | H | Me | Me | Py-2-yl | 3-Br-5-Cl | O | 130-131 |
| 1-52 | Et | H | Me | Me | Bn | 3-Br-5-Cl | O | viscous oil |
| 1-53 | Et | H | Me | Me | 3-Me—Ph | 3-Br-5-Cl | O | 76-77 |
| 1-54 | Et | H | Me | Me | 3-CF₃—Ph | 3-Br-5-Cl | O | 100-102 |
| 1-55 | Et | H | Me | Me | 6-Me—Py-2-yl | 3-Br-5-Cl | O | viscous oil |
| 1-56 | Et | H | Me | Me | Py-2-yl | 3,5-Br₂-4-Cl | O | viscous oil |
| 1-57 | Et | H | Me | Me | CO₂Et | 3-Br-5-Cl | O | 67-69 |
| 1-58 | Et | H | Me | Me | CO₂H | 3-Br-5-Cl | O | 138-140 |
| 1-59 | Et | H | Me | Me | CN | 3-Br-5-Cl | O | 193-195 |
| 1-60 | Et | H | Me | Me | 3-Me—Py-2-yl | 3-Br-5-Cl | O | 84-86 |
| 1-61 | Et | H | Me | Me | Py-2-yl | 3,5-Cl₂ | O | 119-121 |
| 1-62 | Et | H | Me | Me | 5-Me—Py-2-yl | 3-Br-5-Cl | O | 101-103 |
| 1-63 | Et | H | Me | Me | 4-Me—Py-2-yl | 3-Br-5-Cl | O | 68-70 |
| 1-64 | Et | H | Me | Me | Py-2-yl | 3,5-Br₂-4-OMe | O | viscous oil |
| 1-65 | Et | H | Me | Me | Py-2-yl | 3,5-Br₂ | O | 115-117 |
| 1-66 | Et | H | Me | Me | Py-2-yl | 3,5-Br₂-4-OCHF₂ | O | viscous oil |
| 1-67 | Et | H | Me | Me | CONHEt | 3-Br-5-Cl | O | 158-160 |
| 1-68 | Et | H | Me | Me | Py-2-yl | 4-Br-3,5-Cl₂ | O | 117-119 |

TABLE 1-continued

| No. | R¹ | R² | R³ | R⁴ | R⁵ | (X)n | Z | Melting Point (° C.) |
|---|---|---|---|---|---|---|---|---|
| 1-69 | Et | H | Me | Me | Py-4-yl | 3-Br-5-Cl | O | 120-121 |
| 1-70 | Et | H | Me | Me | 2-Me—Ph | 3-Br-5-Cl | O | 107-109 |
| 1-71 | Et | H | Me | Me | CONEt$_2$ | 3-Br-5-Cl | O | 111-113 |
| 1-72 | Et | H | Me | Me | 4-Me—Ph | 3-Br-5-Cl | O | 96-98 |
| 1-73 | Et | H | Me | Me | 2-CF$_3$—Ph | 3-Br-5-Cl | O | 109-111 |
| 1-74 | Me | H | Me | Me | Ph | 3-Br-5-Cl | O | 98-100 |
| 1-75 | Et | Et | Me | Me | Ph | 3-Br-5-Cl | O | viscous oil |
| 1-76 | $^n$Pr | H | Me | Me | Ph | 3-Br-5-Cl | O | 93-95 |
| 1-77 | —C$_2$H$_4$— | | Me | Me | Ph | 3-Br-5-Cl | O | viscous oil |
| 1-78 | Bn | H | Me | Me | Ph | 3-Br-5-Cl | O | 128-130 |
| 1-79 | allyl | H | Me | Me | Ph | 3-Br-5-Cl | O | 103-105 |
| 1-80 | CH$_2$$^c$Pr | H | Me | Me | Ph | 3-Br-5-Cl | O | 113-115 |
| 1-81 | $^i$Pr | H | Me | Me | Ph | 3-Br-5-Cl | O | 134-136 |
| 1-82 | $^n$Bu | H | Me | Me | Ph | 3-Br-5-Cl | O | 97-99 |
| 1-83 | CH$_2$OMe | H | Me | Me | Ph | 3-Br-5-Cl | O | 120-122 |
| 1-84 | CH$_2$C≡CH | H | Me | Me | Ph | 3-Br-5-Cl | O | 119-121 |
| 1-85 | CH$_2$CF$_3$ | H | Me | Me | Ph | 3-Br-5-Cl | O | 98-100 |
| 1-92 | $^i$Pr | H | Me | Me | 3-Me—Ph | 3-Br-5-Cl | O | 119-120 |
| 1-86 | —C$_3$H$_6$— | | Me | Me | Ph | 3-Br-5-Cl | O | 123-125 |
| 1-87 | Ac | H | Me | Me | Ph | 3-Br-5-Cl | O | 132-134 |
| 1-88 | $^i$Bu | H | Me | Me | Ph | 3-Br-5-Cl | O | 118-120 |
| 1-89 | CO$_2$Me | H | Me | Me | Ph | 3-Br-5-Cl | O | 180-182 |
| 1-90 | Et | H | H | H | Ph | 3-Br-5-Cl | O | 140-141 |
| 1-91 | Et | H | Me | H | Ph | 3-Br-5-Cl | O | 130-131 |
| 1-93 | Et | H | H | H | Py-2-yl | 3-Br-5-Cl | O | viscous oil |
| 1-94 | Me | H | Me | Me | Py-2-yl | 3-Br-5-Cl | O | 128-130 |
| 1-95 | Et | Me | Me | Me | Py-2-yl | 3-Br-5-Cl | O | amorphous |
| 1-96 | $^n$Pr | H | Me | Me | Py-2-yl | 3-Br-5-Cl | O | viscous oil |
| 1-97 | CH$_2$$^c$Pr | H | Me | Me | Py-2-yl | 3-Br-5-Cl | O | 131-133 |
| 1-98 | CH$_2$C≡CH | H | Me | Me | Py-2-yl | 3-Br-5-Cl | O | viscous oil |
| 1-99 | Et | H | Me | Me | Py-2-yl | 3,5-Br$_2$-4-F | O | viscous oil |
| 1-100 | Et | H | Me | Me | 4-CF$_3$—Ph | 3-Br-5-Cl | O | 121-123 |
| 1-101 | Et | H | Me | Me | Py-2-yl | 3,5-Cl$_2$-4-Me | O | viscous oil |
| 1-102 | Et | H | Me | Me | 2-MeO—Ph | 3-Br-5-Cl | O | 76-78 |
| 1-103 | Et | H | Me | Me | Py-3-yl | 3-Br-5-Cl | O | 104-106 |
| 1-104 | Et | H | Me | Me | CH$_2$OCH$_2$CH=CH$_2$ | 3-Br-5-Cl | O | 22.3-1.5279 |
| 1-105 | Et | H | Me | Me | CH$_2$OEt | 3-Br-5-Cl | O | 22.1-1.5214 |
| 1-106 | Et | H | Me | Me | CH$_2$CO$_2$Et | 3-Br-5-Cl | O | 20.8-1.5130 |
| 1-107 | Et | H | Me | Me | CH$_2$CO$_2$H | 3-Br-5-Cl | O | 121-123 |
| 1-108 | Et | H | Me | Me | C≡CH | 3-Br-5-Cl | O | 81-83 |
| 1-109 | Et | H | Me | Me | CH$_2$CONHEt | 3-Br-5-Cl | O | 86-89 |
| 1-110 | Et | H | Me | Me | CON(Me)$_2$ | 3-Br-5-Cl | O | 138-140 |
| 1-111 | Et | H | Me | Me | CONHCH$_2$CH$_2$OMe | 3-Br-5-Cl | O | 105-107 |
| 1-112 | Et | H | Me | Me | Me | 3-CH$_2$CH$_2$SO$_2$-4 | O | viscous oil |
| 1-113 | Et | H | Me | Me | Me | 4-MeSO$_2$ | O | 117-118 |
| 1-114 | Et | H | Me | Me | CONHMe | 3-Br-5-Cl | O | 146-148 |
| 1-115 | Et | H | Me | Me | CH$_2$O(Py-2-yl) | 3-Br-5-Cl | O | 22.4-1.5534 |
| 1-116 | Et | H | Me | Me | CONH$^i$Pr | 3-Br-5-Cl | O | amo |
| 1-117 | Et | H | Me | Me | CO(Piperidin-1-yl) | 3-Br-5-Cl | O | 150-152 |
| 1-118 | Et | H | Me | Me | CONHPh | 3-Br-5-Cl | O | 78-80 |
| 1-119 | Et | H | Me | Me | CONH$^n$Bu | 3-Br-5-Cl | O | viscous oil |
| 1-120 | Et | H | Me | Me | CONHCH$_2$CF$_3$ | 3-Br-5-Cl | O | 129-131 |
| 1-121 | Et | H | Me | Me | CONHCH$_2$$^c$Pr | 3-Br-5-Cl | O | amo |
| 1-122 | Et | H | Me | Me | CONHBn | 3-Br-5-Cl | O | amo |
| 1-123 | Et | H | Me | Me | CH$_2$NHCO$_2$Et | 3-Br-5-Cl | O | 71-72 |
| 1-124 | Et | H | Me | Me | CONHCH$_2$C≡CH | 3-Br-5-Cl | O | viscous oil |
| 1-125 | Et | H | Me | Me | CH=N—OBn | 3-Br-5-Cl | O | viscous oil |
| 1-126 | Et | H | Bn | H | CO$_2$Me | 3-Br-5-Cl | O | 115-117 |
| 1-127 | Et | H | Me | Me | CH$_2$NHAc | 3-Br-5-Cl | O | 99-100 |
| 1-128 | Et | H | Me | Me | CH$_2$NHCOPh | 3-Br-5-Cl | O | 154-155 |
| 1-129 | Et | H | Me | Me | CONH$^c$Pr | 3-Br-5-Cl | O | 155-157 |
| 1-130 | Et | H | Me | Me | CONH$^c$Pen | 3-Br-5-Cl | O | 133-135 |
| 1-131 | Et | H | Me | H | CO$_2$Me | 3-Br-5-Cl | O | 81-83 |
| 1-132 | Et | H | Me | Me | CO$_2$Et | 4-Br-3,5-Cl$_2$ | O | viscous oil |
| 1-133 | Et | H | Me | Me | CO$_2$H | 4-Br-3,5-Cl$_2$ | O | 150-152 |
| 1-134 | Et | H | Me | Me | CONH$^s$Bu | 3-Br-5-Cl | O | amo |
| 1-135 | Et | H | Me | Me | CONHCH$_2$CF$_3$ | 4-Br-3,5-Cl$_2$ | O | viscous oil |
| 1-136 | Et | H | Me | Me | CONH$^i$Pr | 4-Br-3,5-Cl$_2$ | O | amo |

TABLE 1-continued

| No. | R¹ | R² | R³ | R⁴ | R⁵ | (X)n | Z | Melting Point (° C.) |
|---|---|---|---|---|---|---|---|---|
| 1-137 | Et | H | Me | Me | CONH$^c$Hex | 3-Br-5-Cl | O | amo |
| 1-138 | Et | H | Me | Me | CONH$^t$Bu | 3-Br-5-Cl | O | 143-145 |
| 1-139 | Et | H | Me | H | CO$_2$H | 3-Br-5-Cl | O | 127-129 |
| 1-140 | Et | H | Me | Me | C(Me)=N—OMe | 3-Br-5-Cl | O | 57-58 |
| 1-141 | Et | H | Me | Me | CONH$^i$Pr | 3-Br-5-Cl | O | 161-163 |
| 1-142 | Et | H | Me | H | CONHCH$_2$CF$_3$ | 3-Br-5-Cl | O | 154-156 |
| 1-143 | Et | H | Me | Me | $^c$Hex | 3-Br-5-Cl | O | 85-86 |
| 1-144 | Et | H | Me | Me | Et | 3-Br-5-Cl | O | 20.6-1.5166 |
| 1-145 | Et | H | Me | Me | C(Me)=N—OCH$_2$$^c$Pr | 3-Br-5-Cl | O | 116-117 |
| 1-146 | Et | H | Me | Me | C(Me)=N—OBn | 3-Br-5-Cl | O | 76-77 |
| 1-147 | Et | H | Me | Me | $^n$Hex | 3-Br-5-Cl | O | 21.0-1.4998 |
| 1-148 | Et | H | Me | Me | $^t$Bu | 3-Br-5-Cl | O | 20.6-1.5216 |
| 1-149 | Et | H | Me | Me | CONHCH$_2$CF$_3$ | 3,4-Cl$_2$ | O | 99-101 |
| 1-150 | Et | H | Me | Me | CO$_2$Et | 3,4-Cl$_2$ | O | 56-58 |
| 1-151 | Et | H | Me | Me | CO$_2$H | 3.4-Cl$_2$ | O | 123-125 |
| 1-152 | Et | H | Me | Me | CONH$^i$Pr | 3.4-Cl$_2$ | O | amo |
| 1-153 | Et | H | —CH$_2$CH$_2$— | | Ph | 3-Br-5-Cl | O | 150-152 |
| 1-154 | Et | H | —(CH$_2$)$_4$— | | Ph | 3-Br-5-Cl | O | 103-105 |
| 1-155 | Et | H | —(CH$_2$)$_5$— | | Ph | 3-Br-5-Cl | O | 85-87 |
| 1-156 | Et | H | $^i$Pr | H | Ph | 3-Br-5-Cl | O | 149-151 |
| 1-157 | Et | H | Ph | H | Ph | 3-Br-5-Cl | O | 156-158 |
| 1-158 | Et | H | Ph | H | Ph | 3-Br-5-Cl | O | 33-55 |
| 1-159 | Et | H | Et | Et | Ph | 3-Br-5-Cl | O | 110-112 |
| 1-160 | Me | H | Me | Me | 2-F—Ph | 3-Br-5-Cl | O | 98-100 |
| 1-161 | Et | H | Me | Me | Py-2-yl | 3.4-Cl$_2$ | O | 202-15458 |
| 1-162 | Et | H | Me | Me | Py-2-yl | 3,5-Br$_2$-4-CF$_3$CH$_2$O | O | viscous oil |
| 1-163 | Et | H | Me | Me | Py-2-yl | 3,5-Br$_2$-4-$^n$HexO | O | 85-87 |
| 1-164 | Et | H | Me | Me | Py-2-yl | 3,5-Cl$_2$-4-Ph | O | amo |
| 1-165 | Et | CH$_2$OMe | Me | Me | Py-2-yl | 3-Br-5-Cl | O | viscous oil |
| 1-166 | Et | | Me | Me | Py-2-yl | 3-Br-5-Cl | O | viscous oil |
| 1-167 | Et | H | Me | CN | Py-2-yl | 3-Br-5-Cl | O | 164-165 |
| 1-168 | Et | Ac | Me | Me | Py-2-yl | 3-Br-5-Cl | O | 117-119 |
| 1-169 | Et | H | —CH$_2$CH$_2$— | | Py-2-yl | 3-Br-5-Cl | O | 138-140 |
| 1-170 | Et | CO(SMe) | Me | Me | Py-2-yl | 3-Br-5-Cl | O | amo |
| 1-171 | Et | H | Me | Me | Py-2-yl | 3-Cl-4-CN | O | 64-66 |
| 1-172 | Et | H | Me | Me | Py-2-yl | 4-MeSO$_2$ | O | viscous oil |
| 1-173 | Et | H | Me | Me | Py-2-yl | 3-Cl-4-Ac | O | viscous oil |
| 1-174 | Et | H | Me | Me | Py-2-yl | 3-Cl-4-CHO | O | 94-96 |
| 1-175 | Et | H | Me | Me | Py-2-yl | 3-Cl-4-CO$_2$Me | O | viscous oil |
| 1-176 | Et | H | Me | Me | Py-2-yl | 3-Cl-4-CO$_2$H | O | 149-151 |
| 1-177 | Et | H | Me | Me | Py-2-yl | 3-Cl-4-CHF$_2$ | O | 66-68 |
| 1-178 | Et | H | Me | Me | Py-2-yl | 3,4,5-Cl$_2$ | O | 92-94 |
| 1-179 | Et | H | Me | Me | Py-2-yl | 3-Cl-4-Br | O | 61-63 |
| 1-180 | Et | H | Me | Me | 4-MeO—Py-2-yl | 3-Br-5-Cl | O | viscous oil |
| 1-181 | Et | H | Me | Me | Py-2-yl | 3-Cl-4-NO$_2$ | O | viscous oil |
| 1-182 | Et | H | Me | Me | Py-2-yl | 3-Br-5-I | O | 130-132 |
| 1-183 | Et | H | Me | Me | Py-2-yl | 3-Br-5-F | O | 79-81 |
| 1-184 | Et | H | Me | Me | Py-2-yl | 3-Me-4-NO$_2$ | O | viscous oil |
| 1-185 | Et | H | Me | Me | 4-CF$_3$—Py-2-yl | 3-Br-5-Cl | O | 74-76 |
| 1-186 | Et | H | Me | Me | Py-2-yl | 3-Br-4,5-Cl$_2$ | O | viscous oil |
| 1-187 | Et | H | Me | Me | Py-2-yl | 3-Cl-5-CN | O | 130-132 |
| 1-188 | Et | H | Me | Me | 1-Oxy-Py-2-yl | 3,4-Cl$_2$ | O | 106-107 |
| 1-189 | Et | H | Me | Me | Py-2-yl | 3,4-Br$_2$-5-Cl | O | 104-106 |
| 1-190 | Et | H | Me | Me | Py-2-yl | 3,5-Cl$_2$-4-CN | O | 94-96 |
| 1-191 | Et | H | Me | Me | Py-2-yl | 3-Cl-5-CF$_3$ | O | 54-96 |
| 1-192 | Et | H | Me | Me | Py-2-yl | 3-Br-5-MeO | O | 66-68 |
| 1-193 | Et | H | Me | Me | Py-2-yl | 3,4-Br$_2$ | O | 206-1.5483 |
| 1-194 | Et | H | Me | Me | Py-2-yl | 3,4-Br$_2$-6-F | O | viscous oil |
| 1-195 | Et | H | Me | Me | Py-2-yl | — | O | 72-74 |
| 1-196 | Et | H | Me | Me | Py-2-yl | 2-Cl-4-CF$_3$ | O | 23.3-1.5070 |
| 1-197 | Et | H | Me | Me | Py-2-yl | 3-Cl-4-Me | O | 55-57 |
| 1-198 | Et | H | Me | Me | Py-2-yl | 3-CF$_3$-4-Cl | O | 23.2-1.4955 |
| 1-199 | Et | H | Me | Me | Py-2-yl | 3-F-4-Cl | O | 47-49 |
| 1-200 | Et | H | Me | Me | Py-2-yl | 3-Br-6-Cl | O | viscous oil |
| 1-201 | Et | H | Me | Me | 4-Ph-Py-2-yl | 3-Br-5-Cl | O | 140-142 |
| 1-202 | Et | H | Me | Me | Py-2-yl | 3-Me-4-Cl | O | 54-56 |

TABLE 1-continued

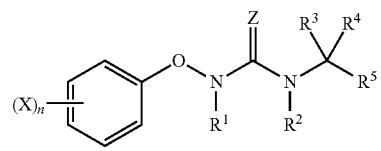

| No. | $R^1$ | $R^2$ | $R^3$ | $R^4$ | $R^5$ | $(X)n$ | Z | Melting Point (° C.) |
|---|---|---|---|---|---|---|---|---|
| 1-203 | Et | H | Me | Me | Py-2-yl | 3,5-$(CF_3)_2$ | O | 23.0-1.4604 |
| 1-204 | Et | H | Me | Me | 6-F-Py-2-yl | 3-Br-5-Cl | O | 67-69 |
| 1-205 | Et | H | Me | Me | 6-Cl-Py-2-yl | 3-Br-5-Cl | O | 22.9-1.5661 |
| 1-206 | Et | H | Me | Me | 3-F-Py-2-yl | 3-Br-5-Cl | O | 110-112 |
| 1-207 | Et | H | Me | Me | 6-Cl-Py-2-yl | 4-Br-3,5-$Cl_2$ | O | amo |
| 1-208 | Et | H | Me | Me | 5-F-Py-2-yl | 3-Br-5-Cl | O | 98-100 |
| 1-209 | Et | H | Me | Me | Thiophen-2-yl | 3-Br-5-Cl | O | 85-86 |
| 1-210 | Et | H | Me | Me | Furan-2-yl | 3-Br-5-Cl | O | 83-84 |
| 1-211 | Et | H | Me | Me | Thiazol-2-yl | 3-Br-5-Cl | O | 71-72 |
| 1-212 | Et | H | Me | Me | Pyrazin-2-yl | 3-Br-5-Cl | O | 20.5-1.5400 |
| 1-213 | Et | H | Me | Me | Pyrimidin-2-yl | 3-Br-5-Cl | O | 137-138 |
| 1-214 | Et | H | Me | Me | [1,2,4]Oxadiazol-3-yl | 3-Br-5-Cl | O | viscous oil |
| 1-215 | Et | H | Me | Me | 4-Me-thiazol-2-yl | 3-Br-5-Cl | O | 94-96 |
| 1-216 | Et | H | Me | Me | Pyrimidin-4-yl | 3-Br-5-Cl | O | viscous oil |
| 1-217 | Et | H | Me | Me | 1H-Pyrazol-3-yl | 3-Br-5-Cl | O | 149-150 |
| 1-218 | Et | H | Me | Me | 1-Me-1H-pyrazol-3-yl | 3-Br-5-Cl | O | 20.5-1.5310 |
| 1-219 | Et | H | Me | Me | 1-Me-1H-pyrazol-5-yl | 3-Br-5-Cl | O | 138-140 |
| 1-220 | Et | H | Me | Me | Isoxazol-5-yl | 3-Br-5-Cl | O | viscous oil |
| 1-221 | Et | H | Me | Me | 4-Et-thiazol-2-yl | 3-Br-5-Cl | O | 107-108 |
| 1-222 | Et | H | Me | Me | 4,5-$Me_2$-thiazole-2-yl | 3-Br-5-Cl | O | 73-76 |
| 1-223 | Et | H | Me | Me | 1-$^t$Bu-1H-pyrazol-3-yl | 3-Br-5-Cl | O | 94-95 |
| 1-224 | $CH_2CH_2F$ | H | Me | Me | Pyrimidin-2-yl | 3-Br-5-Cl | O | 154-156 |
| 1-225 | Et | H | Me | Me | 1-$CF_3CH_2$-1H-pyrazol-5-yl | 3-Br-5-Cl | O | 112-114 |
| 1-226 | Et | H | Me | Me | [1,2,4]Triazin-3-yl | 3-Br-5-Cl | O | 100-101 |
| 1-227 | Et | H | Me | Me | 1-Et-1H-[1,2,4]triazol-3-yl | 3-Br-5-Cl | O | 116-118 |
| 1-228 | Et | H | Me | Me | Pyridazin-3-yl | 3-Br-5-Cl | O | amo |
| 1-229 | Et | H | Me | Me | 2-Me-2H-tetrazol-5-yl | 3-Br-5-Cl | O | viscous oil |
| 1-230 | Et | H | Me | Me | Pyrimidin-2-yl | 4-Br-3,-Cl | O | 127-128 |
| 1-231 | Et | H | Me | Me | 4,5-Dihydro-oxazol-2-yl | 3-Br-5-Cl | O | 134-135 |
| 1-232 | Et | H | Me | Me | 5-Me-Pyrimidin-2-yl | 3-Br-5-Cl | O | 106-107 |
| 1-233 | Et | H | Me | Me | Pyrimidin-2-yl | 3,4-$Cl_2$ | O | viscous oil |
| 1-234 | Et | H | Me | Me | 4,5-$Me_2$-thiazol-2-yl | 4-Br-3,5-$Cl_2$ | O | 119-120 |
| 1-235 | Et | H | Me | Me | 4,5-$Me_2$-thiazol-2-yl | 3,4-$Cl_2$ | O | 20.4-1.5520 |
| 1-236 | Et | H | Me | Me | 4-Me-Pyrimidin-2-yl | 3-Br-5-Cl | O | viscous oil |
| 1-237 | Et | H | Me | Me | 4-Me-Pyrimidin-2-yl | 4-Br-3,5-$Cl_2$ | O | viscous oil |
| 1-238 | Et | H | Me | Me | Py-2-yl | 3-Cl-4-(Py-2-yl) | O | 95-97 |
| 1-239 | Et | H | Me | Me | Quinolin-2-yl | 3-Br-5-Cl | O | amo |
| 1-240 | Et | H | Me | Me | Py-2-yl | 3-Cl-4-C(Me)=N—OMe | O | viscous oil |

[Chemical formula 21]

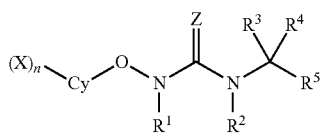

(b)

TABLE 2

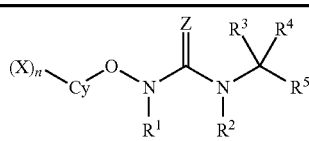

| No. | $R^1$ | $R^2$ | $R^3$ | $R^4$ | $R^5$ | Cy | $(X)n$ | Z | Melting Point (° C) |
|---|---|---|---|---|---|---|---|---|---|
| 2-1 | Et | H | Me | Me | Me | Quinolin-6-yl | 3-Br | O | 85-89 |
| 2-2 | Et | H | Me | Me | Me | Quinolin-6-yl | — | O | 109-112 |
| 2-3 | Et | H | Me | Me | Me | Quinolin-7-yl | 6-OMe | O | 90-92 |
| 2-4 | Et | H | Me | Me | Me | Quinolin-6-yl | 3-Br-7-F | O | 116-118 |

TABLE 2-continued

| No. | R¹ | R² | R³ | R⁴ | R⁵ | Cy | (X)n | Z | Melting Point (° C.) |
|---|---|---|---|---|---|---|---|---|---|
| 2-5 | Et | Et | Me | Me | Me | Quinolin-6-yl | 3-Br | O | 114-116 |
| 2-6 | $CH_2C{\equiv}CH$ | H | Me | Me | Me | Quinolin-6-yl | 3-Br | O | 105-107 |
| 2-7 | Et | H | Me | Me | $CH_2OCH_2CH{=}CH_2$ | Quinolin-6-yl | 3-Br | O | 67-68 |
| 2-8 | Et | H | Me | Me | $C{\equiv}CMe$ | Quinolin-6-yl | 3-Br | O | 86-88 |
| 2-9 | Et | H | Me | Me | Me | Quinolin-2-yl | — | O | 101-102 |
| 2-10 | Et | H | Me | Me | Ph | Quinolin-6-yl | 3-Br | O | 115-116 |
| 2-11 | Et | H | Me | Me | CH=N—OMe | Quinolin-6-yl | 3-Br | O | viscous oil |
| 2-12 | Et | H | Me | Me | Me | Quinolin-4-yl | 7-Cl | O | 114-116 |
| 2-13 | Et | H | Me | Me | Py-2-yl | Quinolin-6-yl | 3-Br | O | 110-111 |
| 2-14 | Et | H | Me | Me | Bn | Quinolin-6-yl | 3-Br | O | 124-125 |
| 2-15 | Et | H | Me | Me | Me | Pyrimidin-2-yl | $4-CF_3$ | O | viscous oil |
| 2-16 | Et | H | Me | Me | Me | Pyrimidin-4-yl | $6-CF_3$ | O | viscous oil |
| 2-17 | Et | H | Me | Me | Me | Pyrimidin-4-yl | $2-CF_3$ | O | 75-77 |
| 2-18 | Et | H | Me | Me | Ph | Pyrimidin-2-yl | $4,6-Me_2$ | O | 61-63 |
| 2-19 | Et | H | Me | Me | Me | Py-2-yl | $6-CF_3$ | O | 72-75 |
| 2-20 | Et | H | Me | Me | Me | Py-2-yl | 6-Cl-5-CN-4-Me | O | 75-78 |
| 2-21 | Et | H | Me | Me | Me | Py-2-yl | 6-Cl-3-CN-4-Me | O | 113-115 |
| 2-22 | Et | H | Me | Me | Me | Py-4-yl | $2,6-Cl_2$ | O | 115-117 |
| 2-23 | Et | H | Me | Me | Ph | Py-2-yl | $4-CF_3$ | O | viscous oil |
| 2-24 | Et | H | Me | Me | Ph | Py-2-yl | $6-Cl-4-CF_3$ | O | 97-99 |
| 2-25 | Et | H | Me | Me | Ph | Py-2-yl | 6-Br | O | 82-85 |
| 2-26 | Et | H | Me | Me | Py-2-yl | Py-2-yl | $6-Cl-4-CF_3$ | O | 90-92 |
| 2-27 | Et | H | Me | Me | Me | Pyridazin-3-yl | $6-CF_3$ | O | 119-121 |
| 2-28 | Et | H | Me | Me | Ph | Pyridazin-3-yl | $6-CF_3$ | O | 124-126 |
| 2-29 | Et | H | Me | Me | Ph | Pyridazin-3-yl | 6-Cl | O | 114-116 |
| 2-30 | Et | H | Me | Me | Ph | Naphthalen-2-yl | — | O | 52-54 |
| 2-31 | Et | Ac | Me | Me | Me | Ouinolin-6-yl | 3-Br | O | |
| 2-32 | Et | H | Me | Me | Me | Quinolin-3-yl | — | O | 82-84 |
| 2-33 | Et | H | Me | Me | Py-2-yl | Quinolin-3-yl | — | O | vis |
| 2-34 | Et | H | Me | Me | Me | Quinolin-4-yl | — | O | vis |
| 2-35 | Et | H | Me | Me | Py-2-yl | Quinolin-4-yl | — | O | vis |
| 2-36 | Et | H | Me | Me | Py-2-yl | Quinoxalin-2-yl | — | O | vis |
| 2-37 | Et | H | Me | Me | Py-2-yl | Quinolin-6-yl | — | O | amo |
| 2-38 | Et | H | Me | Me | Py-2-yl | Quinolin-2-yl | — | O | vis |
| 2-39 | Et | H | Me | Me | Py-2-yl | Quinoxalin-6-yl | — | O | 112-114 |
| 2-40 | $CH_2CF_3$ | H | Me | Me | Py-2-yl | Quinolin-6-yl | 3-Br | O | 101-103 |
| 2-41 | Et | H | Me | Me | Me | Isoquinolin-6-yl | — | O | 113-115 |
| 2-42 | Et | H | Me | Me | Py-2-yl | Isoquinolin-6-yl | — | O | amo |
| 2-43 | Et | H | Me | Me | Py-2-yl | Quinolin-6-yl | 2-Me | O | vis |
| 2-44 | Et | H | Me | Me | Py-2-yl | Ouinolin-6-yl | 3-Me | O | amo |
| 2-45 | Et | H | Me | Me | Py-2-yl | Isoquinolin-1-yl | 3-Cl | O | 109-111 |
| 2-46 | Et | H | Me | Me | Py-2-yl | Py-3-yl | 5-Br | O | 112-114 |
| 2-47 | Et | H | Me | Me | Py-2-yl | Py-2-yl | $5-CF_3-6-Cl$ | O | vie |
| 2-48 | Et | H | Me | Me | Py-2-yl | Py-2-yl | $3-Cl-5-CF_3$ | O | vis |
| 2-49 | Et | H | Me | Me | Py-2-yl | Py-2-yl | $4-CO_2Me-6-Cl$ | O | vis |
| 2-50 | Et | H | Me | Me | Py-2-yl | Py-4-yl | $2,6-Cl_2$ | O | 87-89 |
| 2-51 | Et | H | Me | Me | Py-2-yl | Py-2-yl | 4-Me-6-Cl | O | 119-121 |
| 2-52 | Et | H | Me | Me | Py-2-yl | Py-2-yl | 4-MeO-6-Cl | O | 73-75 |
| 2-53 | Et | H | Me | Me | Py-2-yl | Py-2-yl | 4-CN-6-Cl | O | vis |
| 2-54 | Et | H | Me | Me | Py-2-yl | Py-2-yl | 6-Cl | O | vis |
| 2-55 | Et | H | Me | Me | Pyrimidin-2-yl | Py-2-yl | $4-CF_3-6-Cl$ | O | 20.8-1.5101 |
| 2-56 | Et | H | Me | Me | $4,5-Me_2$-thiazol-2-yl | Py-2-yl | $4-CF_3-6-Cl$ | O | 97-98 |
| 2-57 | Et | H | Me | Me | Py-2-yl | Py-4-yl | 2-Br-6-Me | O | vis |
| 2-58 | Et | H | Me | Me | Py-2-yl | Py-4-yl | $4-CF_3$ | O | 23.0-1.4915 |
| 2-59 | Et | H | Me | Me | Py-2-yl | Py-4-yl | $2,6-Br_2$ | O | 136-138 |
| 2-60 | Et | H | Me | Me | Pyrimidin-2-yl | Py-2-yl | $4,6-Cl_2$ | O | 23.2-1.5290 |
| 2-61 | Et | H | Me | Me | Pyrimidin-2-yl | Py-4-yl | $2,6-Cl_2$ | O | 140-141 |
| 2-62 | Et | H | Me | Me | Py-2-yl | Py-2-yl | $4,6-Cl_2$ | O | 98-99 |
| 2-63 | Et | H | Me | Me | Py-2-yl | Py-4-yl | 2-Br-6-Cl | O | 125-127 |
| 2-64 | Et | H | Me | Me | Py-2-yl | Py-4-yl | 2-Cl | O | 23.8-1.5248 |
| 2-65 | Me | H | Me | Me | Py-2-yl | Py-4-yl | $2,6-Cl_2$ | O | 111-112 |
| 2-66 | Et | H | Me | Me | Py-2-yl | Py-4-yl | $2-Cl-6-N(Me)_2$ | O | 84-86 |
| 2-67 | ⁿPr | H | Me | Me | Py-2-yl | Py-4-yl | $2,6-Cl_2$ | O | amo |
| 2-68 | Et | H | Me | Me | 6-Cl—Py-2-yl | Py-4-yl | $2,6-Cl_2$ | O | 150-151 |
| 2-69 | Et | H | Me | Me | Py-2-yl | Py-2-yl | $4-CF_3-6$-ⁱPr | O | 22.8-1.4891 |
| 2-70 | Et | H | Me | Me | Py-2-yl | Py-4-yl | 2-CN-6-Me | O | vis |
| 2-71 | Et | H | Me | Me | Py-2-yl | Pyrimidin-4-yl | 2-Me-6-Cl | O | vis |
| 2-72 | Et | H | Me | Me | Py-2-yl | Pyrimidin-4-yl | $2,6-Cl_2$ | O | vis |

TABLE 2-continued

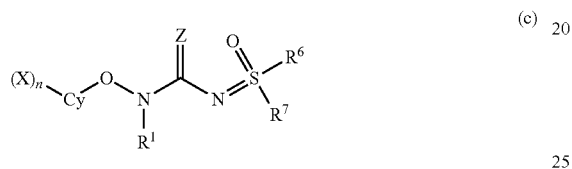

| No. | R¹ | R² | R³ | R⁴ | R⁵ | Cy | (X)n | Z | Melting Point (° C) |
|---|---|---|---|---|---|---|---|---|---|
| 2-73 | Et | H | Me | Me | Py-2-yl | Py-3-yl | 5,6-Cl$_2$ | O | 90-92 |
| 2-74 | Et | H | Me | Me | Py-2-yl | Py-4-yl | 2-Br-6-CF$_3$ | O | vis |
| 2-75 | Et | H | Me | Me | Py-2-yl | Py-2-yl | 4-Br-6-CF$_3$ | O | vis |
| 2-76 | Et | H | Me | Me | Py-2-yl | Py-2-yl | 4-N(Me)2-6-Cl | O | 91-93 |
| 2-77 | Et | H | Me | Me | Py-2-yl | Py-3-yl | 6-Cl | O | 62-64 |
| 2-78 | Et | H | Me | Me | Pyrimidin-2-yl | Py-3-yl | 6-Cl | O | amo |

[Chemical 22]

(c)

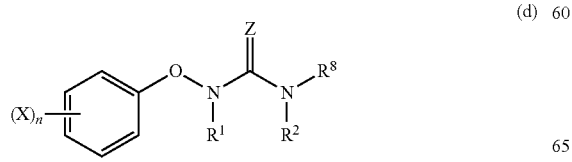

TABLE 3

| No. | R¹ | R⁶ | R⁷ | Cy | (X)n | Z | Melting Point (°C) |
|---|---|---|---|---|---|---|---|
| 3-1 | Et | Me | Me | Ph | 3-Br-5-Cl | O | |
| 3-2 | Et | —C$_4$H$_8$— | | Ph | 3-Br-5-Cl | O | amorphous |
| 3-3 | Et | Me | Ph | Ph | 3-Br-5-Cl | O | amorphous |
| 3-4 | Et | Me | Py-2-yl | Ph | 3-Br-5-Cl | O | amorphous |
| 3-5 | Et | Me | Me | Ph | 3,5-Cl$_2$ | O | |
| 3-6 | Et | —C$_4$H$_8$— | | Ph | 3,5-Cl$_2$ | O | |
| 3-7 | Et | Me | Ph | Ph | 3,5-Cl$_2$ | O | |
| 3-8 | Et | Me | Py-2-yl | Ph | 3,5-Cl$_2$ | O | |
| 3-9 | Et | Me | Me | Ph | 3,5-Br$_2$ | O | |
| 3-10 | Et | —C$_4$H$_8$— | | Ph | 3,5-Br$_2$ | O | |
| 3-11 | Et | Me | Ph | Ph | 3,5-Br$_2$ | O | |
| 3-12 | Et | Me | Py-2-yl | Ph | 3,5-Br$_2$ | O | |
| 3-13 | Et | Me | Me | Quinolin-6-yl | — | O | |
| 3-14 | Et | —C$_4$H$_8$— | | Quinolin-6-yl | — | O | |
| 3-15 | Et | Me | Ph | Quinolin-6-yl | — | O | |
| 3-16 | Et | Me | Py-2-yl | Quinolin-6-yl | — | O | |
| 3-17 | Et | Me | Me | Quinolin-6-yl | 3-Br | O | |
| 3-18 | Et | —C$_4$H$_8$— | | Quinolin-6-yl | 3-Br | O | |
| 3-19 | Et | Me | Ph | Quinolin-6-yl | 3-Br | O | |
| 3-20 | Et | Me | Py-2-yl | Quinolin-6-yl | 3-Br | O | |
| 3-21 | Et | Me | ⁿBu | Ph | 3-Br-5-Cl | O | 89-91 |
| 3-22 | Et | Me | Ph | Ph | 4-Br-3,5-Cl$_2$ | O | 117-120 |

[Chemical formula 23]

(d)

TABLE 4

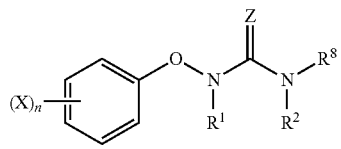

| No. | R¹ | R² | R⁸ | (X)n | Z | Melting Point (° C) |
|---|---|---|---|---|---|---|
| 4-1 | Et | Me | Ph | 3-Br-5-Cl | O | |
| 4-2 | Et | H | Ph | 3-Br-5-Cl | O | 107-109 |
| 4-3 | Et | H | Indan-1-yl | 3-Br-5-Cl | O | 95-96 |
| 4-4 | Et | H | 1,2,3,4-Tetrahydro-naphthalen-1-yl | 3-Br-5-Cl | O | 106-108 |
| 4-5 | Et | H | 5,6,7,8-Tetrahydro-quinolin-8-yl | 3-Br-5-Cl | O | 80-83 |
| 4-6 | Et | H | 2-Ph-ᶜPr | 3-Br-5-Cl | O | 129-131 |
| 4-7 | Et | H | Quinolin-8-yl | 3-Br-5-Cl | O | 110-111 |
| 4-8 | Et | H | CO₂Et | 3-Br-5-Cl | O | 95-97 |
| 4-9 | Et | H | CO₂Me | 3-Br-5-Cl | O | |
| 4-10 | Et | H | ᶜHex | 3-Br-5-Cl | O | |
| 4-11 | Et | H | 2-F—Ph | 3-Br-5-Cl | O | |
| 4-12 | Et | H | 3-Me—Ph | 3-Br-5-Cl | O | |
| 4-13 | Et | H | 3-CF₃—Ph | 3-Br-5-Cl | O | |
| 4-14 | Et | H | Py-2-yl | 3-Br-5-Cl | O | |
| 4-15 | Et | H | 6-Me—Py-2-yl | 3-Br-5-Cl | O | |
| 4-16 | Et | H | 4-MeO—Py-2-yl | 3-Br-5-Cl | O | |
| 4-17 | Et | H | 4-CF₃—Py-2-yl | 3-Br-5-Cl | O | |
| 4-18 | Et | H | 6-F—Py-2-yl | 3-Br-5-Cl | O | |
| 4-19 | Et | H | Thiophen-2-yl | 3-Br-5-Cl | O | |
| 4-20 | Et | H | Thiazol-2-yl | 3-Br-5-Cl | O | |
| 4-21 | Et | H | Pyrazin-2-yl | 3-Br-5-Cl | O | |
| 4-22 | Et | H | Pyrimidin-2-yl | 3-Br-5-Cl | O | |
| 4-23 | Et | Et | Ph | 3-Br-5-Cl | O | |
| 4-24 | allyl | H | Ph | 3-Br-5-Cl | O | |
| 4-25 | CH₂OMe | H | Ph | 3-Br-5-Cl | O | |
| 4-26 | CH₂C≡CH | H | Ph | 3-Br-5-Cl | O | |
| 4-27 | Et | CH₂OMe | Py-2-yl | 3-Br-5-Cl | O | |
| 4-28 | Et | CO₂Me | Py-2-yl | 3-Br-5-Cl | O | |
| 4-29 | Et | Ac | Py-2-yl | 3-Br-5-Cl | O | |

| No. | ¹H-NMR(CDCl₃, δ ppm) |
|---|---|
| 1-2 | 7.48~7.30(m, 4H), 5.51(s, 1H), 3.64(q, 2H), 1.34(s, 9H), 1.15(t, 3H) |
| 1-3 | 7.22~7.21(m, 2H), 7.11(t, 1H), 5.44(s, 1H), 3.62(q, 2H), 1.35(s, 9H), 1.13(t, 3H) |
| 1-4 | 7.77(s, 1H), 7.72(d, 1H), 7.65~7.54(m, 3H), 7.46(d, 1H), 7.25~7.22(m, 1H), 5.87(s, 1H), 3.72(q, 2H), 1.37(s, 9H), 1.23(t, 3H) |
| 1-5 | 7.06(s, 3H), 5.43(s, 1H), 3.62(q, 2H), 1.35(s, 9H), 1.13(t, 3H) |
| 1-8 | 7.42(dd, 1H), 7.35~7.33(m, 2H), 5.41(s, 1H), 3.63(q, 2H), 1.35(s, 9H), 1.14(t, 3H) |
| 1-9 | 6.75(t, 1H), 6.62~6.59(m, 2H), 5.47(s, 1H), 3.79(s, 3H), 3.62(q, 2H), 1.34(s, 9H), 1.14(t, 3H) |
| 1-12 | 7.52~7.47(m, 2H), 7.24(t, 1H), 7.20(dd, 1H), 7.00~6.95(m, 2H), 5.54(s, 1H), 3.86(s, 3H), 3.65(q, 2H), 1.35(s, 9H), 1.17(t, 3H) |
| 1-14 | 6.90(t, 1H), 6.76(t, 1H), 6.63(t, 1H), 5.47(br, 1H), 3.78(s, 3H), 3.61(q, 2H), 1.34(s, 9H), 1.14(t, 3H) |
| 1-15 | 7.11(s, 1H), 7.03(s, 1H), 6.87(s, 1H), 5.49(br, 1H), 3.61(q, 2H), 2.32(s, 3H), 1.34(s, 9H), 1.13(t, 3H) |
| 1-16 | 7.38(d, 1H), 7.30~7.19(m, 2H), 5.75(br, 1H), 3.66(q, 2H), 1.28(s, 9H), 1.19(t, 3H) |
| 1-19 | 7.52(d, 1H), 7.44(d, 1H), 5.73(br, 1H), 3.67(q, 2H) 1.34(s, 9H), 1.19(t, 3H) |
| 1-22 | 736~7.30(m, 2H), 7.12(t, 1H), 5.76(br, 1H), 3.67(q, 2H), 1.35(s, 9H), 1.19(t, 3H) |
| 1-35 | 7.39~7.19(m, 5H), 6.96(t, 1H), 6.79(t, 1H), 6.67(t, 1H), 5.95(br, 1H), 3.80(s, 3H), 3.59(q, 2H), 1.67(s, 6H), 1.13(t, 3H) |
| 1-46 | 7.39~7.09(m, 9H), 7.07(t, 1H), 6.06(br, 1H), 3.62(q, 2H), 1.67(s, 6H), 1.14(t, 3H) |
| 1-50 | 7.33(s, 1H), 7.24~7.21(m, 2H), 7.12(t, 1H), 6.53(s, 1H), 3.77(s, 3H), 3.65(q, 2H), 1.50(s, 6H), 1.17(t, 3H) |
| 1-52 | 7.24~7.01(m, 8H), 5.32(s, 1H), 3.64(q, 2H), 2.98(s, 2H), 1.35(s, 9H), 1.15(t, 3H) |
| 1-55 | 8.71(s, 1H), 7.57(t, 1H), 7.34(t, 1H), 7.23(t, 1H), 7.18(t, 1H), 7.15(d, 1H), 6.99(d, 1H), 3.71(q, 2H), 2.40(s, 3H), 1.73(s, 6H), 1.20(t, 3H) |
| 1-56 | 8.44(ddd, 1H), 8.16(br, 1H), 7.70(dt, 1H), 7.55(s, 2H), 7.37(dd, 1H), 7.17(ddd, 1H), 3.68(q, 2H), 1.74(s, 6H), 1.19(t, 3H) |
| 1-64 | 8.46(d, 1H), 8.05(br, 1H), 7.69(dt, 1H), 7.43(s, 2H), 7.37(d, 1H), 7.17(dd, 1H), 3.85(s, 3H), 3.67(q, 2H), 1.74(s, 6H), 1.18(t, 3H) |
| 1-66 | 8.44(ddd, 1H), 8.16(br, 1H), 7.70(dt, 1H), 7.51(s, 2H), 7.38(d, 1H), 7.18(ddd, 1H), 6.56(t, 1H), 3.68(q, 2H), 1.74(s, 6H), 1.19(t, 3H) |
| 1-75 | 7.50~7.45(m, 3H), 7.36~7.29(m, 3H) 7.24~7.18(m, 2H), 3.28(q, 2H), 3.12(q, 2H), 1.55(s, 6H), 0.95(t, 3H), 0.89(t, 3H) |
| 1-77 | 7.42~7.25(m, 5H), 7.21(t, 1H), 7.14(t, 1H), 7.10(t, 1H), 3.51(t, 2H), 3.25(t, 2H), 1.83(s, 6H) |
| 1-93 | 8.50(d, 1H), 7.65(dt, 1H), 7.28~7.15(m, 5H), 6.74(t, 1H), 4.55(d, 2H), 3.70(q, 2H), 1.18(t, 3H) |
| 1-95 | 8.55(ddd, 1H), 7.64(dt, 1H), 7.49~7.31(m, 4H), 7.11(ddd, 1H), 3.25(q, 2H), 2.91(s, 3H), 1.56(s, 6H), 0.91(t, 3H) |
| 1-96 | 8.43(ddd, 1H), 8.05(br, 1H), 7.69(dt, 1H), 7.39~7.32(m, 2H), 7.22~7.14(m, 3H), 3.59(t, 2H), 1.73(s, 6H), 1.72~1.57(m, 2H), 0.92(t, 3H) |

| No. | ¹H-NMR(CDCl₃, δ ppm) |
|---|---|
| 1-98 | 8.45~8.41(m, 2H), 7.70(ddd, 1H), 7.40~7.15(m, 5H), 4.38(s, 2H), 2.24(t, 1H), 1.75(s, 6H) |
| 1-99 | 8.44(ddd, 1H), 8.13(br, 1H), 7.70(dt, 1H), 7.44(d, 2H), 7.38(d, 1H), 7.17(ddd, 1H), 3.68(q, 2H), 1.74(s, 6H), 1.19(t, 3H) |
| 1-101 | 8.45(ddd, 1H), 8.02(br, 1H), 7.69(dt, 1H), 7.37(d, 1H), 7.23(s, 2H), 7.16(ddd, 1H), 3.67(q, 2H), 2.39(s, 3H), 1.74(s, 6H), 1.18(t, 3H) |
| 1-112 | 7.90(d, 1H), 7.14(dd, 1H), 7.02(d, 1H), 5.42(s, 1H), 3.63(q, 1H), 3.37~3.33(m, 2H), 3.01(dd, 2H), 2.55~2.47(m, 2H), 1.33(s, 9H), 1.13(t, 3H) |
| 1-116 | 7.24~7.22(m, 2H), 7.12(t, 1H), 6.42(br, 1H), 5.98(br, 1H), 4.08~3.96(m, 1H), 3.63(q, 2H), 1.56(s, 6H), 1.18~1.13(m, 9H) |
| 1-119 | 7.23~7.22(m, 2H), 7.11(t, 1H), 6.40(br, 1H), 6.26(br, 1H), 3.64(q, 2H), 3.26(q, 2H), 1.57(s, 6H), 1.55~1.24(m, 4H) 1.15(t, 3H), 0.93(t, 3H) |
| 1-121 | 7.27~7.23(m, 2H), 7.12(t, 1H), 6.41(br, 1H), 6.29(br, 1H), 3.64(q, 2H), 3.13(q, 2H), 1.58(s, 6H), 1.16(t, 3H), 1.03~0.86(m, 1H), 0.55~0.48(m, 2H), 0.18~0.23(m, 2H) |
| 1-122 | 7.36~7.09(m, 8H), 6.59(br, 1H), 6.29(br, 1H), 4.46(d, 2H), 3.62(q, 2H), 1.56(s, 6H), 1.11(t, 3H) |
| 1-124 | 7.24~7.21(m, 2H), 7.11(t, 1H), 6.64(br, 1H), 6.17(br, 1H), 4.07~4.04(m, 2H), 3.64(q, 2H), 2.25~2.23(m, 1H), 1.57(s, 6H), 1.16(t, 3H) |
| 1-125 | 7.40(s, 1H), 7.36~7.21(m, 7H), 7.12(t, 1H), 6.56(br, 1H), 4.97(s, 2H), 3.64(q, 2H), 1.51(s, 6H) 1.15(t, 3H) |
| 1-132 | 7.24(s, 2H), 6.20(br, 1H), 4.19(q, 2H), 3.62(q, 2H), 1.55(s, 6H), 1.27(t, 3H), 1.14(t, 3H) |
| 1-134 | 7.22~7.21(m, 2H), 7.10(t, 1H), 6.42(br, 1H), 5.95(br, 1H), 3.88~3.84(m, 1H), 3.62(q, 2H), 1.55(s, 6H), 1.50~1.42(m, 2H), 1.13~1.10(m, 6H), 0.89(t, 3H) |
| 1-135 | 7.21(s, 2H), 7.08(br, 1H), 5.95(br, 1H), 3.97~3.90(m, 1H), 3.64(q, 2H), 1.55(s, 6H), 1.14(t, 3H) |

| No. | ¹H-NMR(CDCl₃, δ ppm) |
|---|---|
| 1-136 | 7.22(s, 2H), 6.52(br, 1H), 5.86(br, 1H), 4.05~4.00(m, 1H), 3.62(q, 2H), 1.55(s, 6H), 1.15~1.12(m, 9H) |
| 1-137 | 7.21~7.20(m, 2H), 7.10(t, 1H), 6.43(br, 1H), 6.02(br, 1H), 3.72~3.70(m, 1H), 3.62(q, 2H), 1.89~1.85(m, 2H), 1.70~1.60(m, 2H), 1.59~1.50(m, 2H), 1.54(s, 6H), 1.36~1.30(m, 2H), 1.22~1.06(m, 2H), 1.13(t, 3H) |
| 1-152 | 7.37(d, 1H), 7.28(d, 1H), 7.01~6.99(m, 1H), 6.41(br, 1H), 5.95(br, 1H), 4.12~4.01(m, 1H), 3.62(q, 2H), 1.53(s, 6H), 1.16~1.12(m, 9H) |
| 1-162 | 8.44(dd, 1H), 8.14(br, 1H), 7.70(dt, 1H), 7.47(s, 2H), 7.38(d, 1H), 7.17(ddd, 1H), 4.36(q, 2H), 3.67(q, 2H), 1.74(s, 6H), 1.37(t, 3H), 1.19(t, 3H) |
| 1-164 | 8.48(dd, 1H), 8.12(br, 1H), 7.71(dt, 1H), 7.48~7.37(m, 5H), 7.26~7.33(m, 3H), 7.18(ddd, 1H), 3.72(q, 2H), 1.77(s, 6H), 1.23(t, 3H) |
| 1-165 | 8.55(dd, 1H), 7.64(dt, 1H), 7.50~7.38(m, 4H), 7.12(ddd, 1H), 4.26(s, 2H), 3.33(s, 3H), 3.24(q, 2H), 1.58(s, 6H), 0.87(t, 3H) |
| 1-166 | 8.56(dd, 1H), 7.65(dt, 1H), 7.55~7.44(m, 4H), 7.13(dd, 1H), 3.68(s, 3H), 3.31(q, 2H), 1.57(s, 6H), 0.91(t, 3H) |
| 1-170 | 8.55(dd, 1H), 7.66(dt, 1H), 7.54~7.43(m, 4H), 7.13(dd, 1H), 3.31(q, 2H), 2.21(s, 3H), 1.57(s, 6H), 0.92(t, 3H) |
| 1-172 | 8.36(d, 1H), 8.17(s, 1H), 7.93(dd, 2H), 7.69(ddd, 1H), 7.42~7.35(m, 3H), 7.14(dd, 1H), 3.72(q, 2H), 3.28(s, 3H), 1.74(s, 6H), 1.20(t, 3H) |
| 1-173 | 8.40(dd, 1H), 8.12(br, 1H), 7.72~7.66(m, 2H), 7.38~7.29(m, 2H), 7.20~7.13(m, 2H), 3.70(q, 2H), 2.65(s, 3H), 1.74(s, 6H), 1.20(t, 3H) |
| 1-175 | 8.39(d, 1H), 8.13(br, 1H), 7.89(d, 1H), 7.68(dt, 1H), 7.38~7.35(m, 2H), 7.19~7.12(m, 2H), 3.90(s, 3H), 3.70(q, 2H), 1.73(s, 6H), 1.19(t, 3H) |
| 1-180 | 8.27(d, 1H), 8.07(br, 1H), 7.33(dd, 1H), 7.22~7.18(m, 2H), 6.84(d, 1H), 6.69(dd, 1H), 3.84(s, 3H), 3.67(q, 2H), 1.72(s, 6H), 1.21(t, 3H) |

| No. | ¹H-NMR(CDCl₃, δ ppm) |
|---|---|
| 1-181 | 8.38(dd, 1H), 8.29(br, 1H), 8.01(d, 1H), 7.70(dt, 1H), 7.46(d, 1H), 7.37(d, 1H), 7.28~7.15(m, 2H), 3.72(q, 2H), 1.74(s, 6H), 1.21(t, 3H) |

| No. | ¹H-NMR(CDCl₃, δ ppm) |
|---|---|
| 1-184 | 8.37(dd, 1H), 8.16(br, 1H), 8.09(d, 1H), 7.69(dt, 1H), 7.37(d, 1H), 7.20~7.13(m, 3H), 3.69(q, 2H), 2.65(s, 3H), 1.74(s, 6H), 1.20(t, 3H) |
| 1-186 | 8.43(dd, 1H), 8.17(br, 1H), 7.70(dt, 1H), 7.51(d, 1H), 7.39~7.36(m, 2H), 7.17(dd, 1H), 3.68(q, 2H), 1.74(s, 6H), 1.19(t, 3H) |
| 1-194 | 8.42(ddd, 1H), 8.26(br, 1H), 7.73(d, 1H), 7.68(dt, 1H), 7.42~7.35(m, 2H), 7.15(ddd, 1H), 3.70(q, 2H), 1.74(s, 6H), 1.21(t, 3H) |
| 1-200 | 8.44(d, 1H), 8.23(s, 1H), 7.68(ddd, 1H), 7.61(d, 1H), 7.37(d, 1H), 7.25(d, 1H), 7.15(ddd, 1H), 7.12(dd, 1H), 3.72(q, 2H), 1.75(s, 6H), 1.23(t, 3H) |
| 1-207 | 7.78(s, 1H), 7.66(dd, 1H), 7.36(d, 2H), 7.28(d, 1H), 7.20(d, 1H), 3.69(q, 2H), 1.72(s, 6H), 1.20(t, 3H) |
| 1-214 | 8.64(s, 1H), 7.27(dd, 1H), 7.24(dd, 1H), 7.17(dd, 1H), 6.15(s, 1H), 3.61(q, 2H), 1.76(s, 6H), 1.15(t, 3H) |
| 1-216 | 9.12(s, 1H), 8.71(d, 1H), 7.39(d, 1H), 7.34~7.32(m, 1H), 7.26~7.21(m, 2H), 7.13(br, 1H), 3.64(q, 2H) 1.71(s, 6H), 1.17(t, 3H) |
| 1-220 | 8.16(dd, 1H), 7.25~7.24(m, 2H), 7.13(t, 1H), 6.13(s, 1H), 5.93(br, 1H), 3.59(q, 2H), 1.72(s, 6H), 1.12(t, 3H) |
| 1-228 | 9.10(dd, 1H), 7.57(dd, 1H), 7.49~7.46(m, 1H), 7.30(t, 1H), 7.27~7.18(m, 3H), 3.62(q, 2H), 1.81(s, 6H) 1.15(t, 3H) |
| 1-229 | 8.94(br, 1H), 8.15(d, 1H), 7.80~7.70(m, 3H), 7.51~7.44(m, 3H), 7.34(t, 1H), 7.20(t, 1H), 3.74(q, 2H), 1.82(s, 6H), 1.23(t, 3H) |
| 1-230 | 8.43~8.42(m, 1H), 7.98(s, 1H), 7.68(ddd, 1H), 7.37(dd, 1H), 7.32(d, 1H), 7.29(d, 1H), 7.16~7.12(m, 3H), 3.97(s, 3H), 3.68(q, 2H), 2.20(s, 3H), 1.73(s, 6H), 1.18(t, 3H) |
| 1-233 | 8.68(d, 2H), 7.71(s, 1H), 7.41(d, 1H), 7.39(d, 1H), 7.16(dd, 1H), 7.10(dd, 1H), 3.68(q, 2H), 1.79(s, 6H), 1.19(t, 3H) |

| No. | ¹H-NMR(CDCl₃, δ ppm) |
|---|---|
| 1-236 | 8.54(d, 1H), 8.10(s, 1H), 7.34(dd, 2H), 7.23(dd, 1H), 7.20(dd, 1H), 3.70(q, 2H), 2.45(s, 3H), 1.78(s, 6H), 1.20(t, 3H) |
| 1-237 | 8.54(d, 1H), 8.10(s, 1H), 7.35(s, 2H), 7.01(d, 1H), 3.70(q, 2H), 2.45(s, 3H), 1.77(s, 6H), 1.20(t, 3H) |
| 2-11 | 8.83(s, 1H), 8.24(d, 1H), 8.07(d, 1H), 7.54(d, 1H), 7.36~7.19(m, 2H), 6.05(s, 1H), 3.69(q, 2H), 1.68(s, 6H), 1.18(t, 3H) |
| 2-15 | 8.89(d, 1H), 7.46(d, 1H), 5.56(s, 1H), 3.82(q, 2H), 1.35(s, 9H), 1.20(t, 3H) |
| 2-16 | 9.02(s, 1H), 7.57(s, 1H), 5.53(s, 1H), 3.73(brs, 2H), 1.35(s, 9H), 1.19(t, 3H) |
| 2-23 | 8.48(d, 1H), 7.49(s, 1H), 7.38~7.19(m, 6H), 6.15(br, 1H), 3.70(q, 2H), 1.67(s, 6H), 1.18(t, 3H) |
| 2-33 | 8.92(d, 1H), 8.38(d, 1H), 8.34(br, 1H), 8.09(d, 1H), 7.94(d, 1H), 7.77(d, 1H), 7.69~7.51(m, 3H), 7.36(d, 1H), 7.12(dd, 1H), 3.79(q, 2H), 1.75(s, 6H), 1.26(t, 3H) |
| 2-34 | 8.82(d, 1H), 8.18~8.12(m, 2H), 7.77(dt, 1H), 7.58(dt, 1H), 7.28(d, 1H), 5.50(br, 1H), 3.75(q, 2H), 1.33(s, 9H), 1.22(t, 3H) |
| 2-35 | 8.79(d, 1H), 8.65(br, 1H), 8.42(dd, 1H), 8.11(d, 1H), 7.94(dd, 1H), 7.79(dt, 1H), 7.66~7.60(m, 2H), 7.34~7.29(m, 2H), 7.03(ddd, 1H), 3.85(q, 2H), 1.74(s, 6H), 1.26(t, 3H) |
| 2-36 | 8.91(s, 1H), 8.34(ddd, 1H), 8.19(br, 1H), 8.10(d, 1H), 7.98(d, 1H), 7.78~7.63(m, 3H), 7.36(dd, 1H), 7.12(dd, 1H), 3.89(q, 2H), 1.75(s, 6H), 1.26(t, 3H) |
| 2-37 | 8.81(dd, 1H), 8.36(dd, 1H), 8.11~8.07(m, 3H), 7.68~7.59(m, 3H), 7.40~7.35(m, 2H), 7.11(dd, 1H), 3.77(q, 2H), 1.75(s, 6H), 1.24(t, 3H) |
| 2-38 | 8.34(dd, 1H), 8.19(d, 1H), 7.96(d, 1H), 7.79(br, 1H), 7.78(d, 1H), 7.69(t, 1H), 7.61(t, 1H), 7.51~7.41(m, 2H), 7.34(d, 1H), 7.06(dd, 1H), 3.80(q, 2H), 1.71(s, 6H), 1.23(t, 3H) |

| No. | ¹H-NMR(CDCl₃, δ ppm) |
|---|---|
| 2-42 | 9.15(s, 1H), 8.46(d, 1H), 8.33(d, 1H), 8.13(br, 1H), 7.95(d, 1H), 7.64(dt, 1H), 7.60(d, 1H), 7.56(d, 1H), 7.48(dd, 1H), 7.35(d, 1H), 7.10(dd, 1H), 3.76(q, 2H), 1.73(s, 6H), 1.23(t, 3H) |
| 2-43 | 8.37(d, 1H), 8.05(s, 1H), 8.00(dd, 1H), 7.97(d, 1H), 7.65(ddd, 1H), 7.57~7.55(m, 2H), 7.36(d, 1H), 7.27(d, 1H), 7.11(ddd, 1H), 3.76(q, 2H), 2.72(s, 3H), 1.74(s, 6H), 1.24(t, 3H) |

| No. | $^1$H-NMR(CDCl$_3$, δ ppm) |
|---|---|
| 2-44 | 8.66(d, 1H), 8.38~8.36(m, 1H), 8.07~8.03(m, 2H), 7.83(s, 1H), 7.65(ddd, 1H), 7.54~7.51(m, 2H), 7.36(dd, 1H), 7.11(ddd, 1H), 3.76(q, 2H), 2.50(s, 3H), 1.74(s, 6H), 1.24(t, 3H) |
| 2-47 | 8.42(dd, 1H), 8.14(br, 1H), 8.03(d, 1H), 7.68(dt, 1H), 7.36(d, 1H), 7.29(d, 1H), 7.15(ddd, 1H), 3.74(br, 2H), 1.73(s, 6H), 1.26(t, 3H) |
| 2-48 | 8.43~8.38(m, 2H), 8.27(br, 1H), 7.96(d, 1H), 7.68(dt, 1H), 7.37(d, 1H), 7.16~7.13(m, 1H), 3.87(q, 2H), 1.74(s, 6H), 1.22(t, 3H) |
| 2-49 | 8.42(d, 1H), 8.02(br, 1H), 7.73(s, 1H), 7.66~7.63(m, 2H), 7.34(d, 1H), 7.13(dd, 1H), 3.94(s, 3H), 3.69(br, 2H), 1.71(s, 6H), 1.21(t, 3H) |
| 2-53 | 8.42~8.40(m, 1H), 8.16(br, 1H), 7.68(dt, 1H), 7.44(s, 1H), 7.35(d, 1H), 7.30(s, 1H), 7.15(dd, 1H), 3.73(br, 2H), 1.72(s, 6H), 1.21(t, 3H) |
| 2-54 | 8.42(d, 1H), 7.88(br, 1H), 7.69~7.64(m, 2H), 7.34(d, 1H), 7.17~7.06(m, 3H), 3.71(q, 2H), 1.70(s, 6H), 1.20(t, 3H) |
| 2-57 | 8.39(dd, 1H), 8.14(br, 1H), 7.68(dt, 1H), 7.36(d, 1H), 7.21(s, 1H), 7.17~7.15(m, 1H), 6.98(s, 1H), 3.70(br, 2H), 2.51(s, 3H), 1.72(s, 6H), 1.17(t, 3H) |
| 2-67 | 8.40~8.39(m, 1H), 8.29(s, 1H), 7.71(ddd, 1H), 7.38(d, 1H), 7.20~7.17(m, 3H), 3.61(br, 2H), 1.73(s, 6H), 1.70~1.62(m, 2H), 0.94(t, 3H) |
| 2-70 | 8.38~8.37(m, 1H), 8.28(s, 1H), 7.71(ddd, 1H), 7.41(d, 1H), 7.38(d, 1H), 7.26(d, 1H), 7.18(ddd, 1H), 3.72(br, 2H), 2.59(s, 3H), 1.74(s, 6H), 1.20(t, 3H) |
| 2-71 | 8.39~8.38(m, 1H), 8.06(br, 1H), 7.66(dt, 1H), 7.34(d, 1H), 7.15~7.12(m, 2H), 3.90~3.50(br, 2H), 2.68(s, 3H), 1.71(s, 6H), 1.20(t, 3H) |

| No. | $^1$H-NMR(CDCl$_3$, δ ppm) |
|---|---|
| 2-72 | 8.43(d, 1H), 8.27(s, 1H), 7.70(ddd, 1H), 7.37(d, 1H), 7.28(s, 1H), 7.18(dd, 1H), 3.75(br, 2H), 1.74(s, 6H), 1.23(t, 3H) |
| 2-74 | 8.41(s, 1H), 8.37~8.35(m, 1H), 7.72(ddd, 1H), 7.60(d, 1H), 7.52(d, 1H), 7.39~7.36(m, 1H), 7.18(ddd, 1H), 3.74(br, 2H), 1.74(s, 6H), 1.22(t, 3H) |
| 2-75 | 8.39(d, 1H), 8.23(s, 1H), 7.71(s, 1H), 7.68(dd, 1H), 7.58(s, 1H), 7.35(d, 1H), 7.14(dd, 1H), 3.76(br, 2H), 1.73(s, 6H), 1.24(t, 3H) |
| 2-78 | 8.65(d, 2H), 8.36(d, 1H), 7.84(br, 1H), 7.57(dd, 1H), 7.28(d, 1H), 7.15(t, 1H), 3.69(q, 2H), 1.77(s, 6H), 1.25(t, 3H) |
| 3-2 | 7.15(d, 2H), 7.03(t, 1H), 3.75(q, 2H), 3.65~3.55(m, 2H), 3.30~3.21(m, 2H), 2.39~2.18(m, 4H), 1.22(t, 3H) |
| 3-3 | 7.87(d, 2H), 7.70~7.55(m, 3H), 7.19~7.16(m, 2H), 7.07(t, 1H), 3.76(q, 2H), 3.34(s, 3H), 1.23(t, 3H) |
| 3-4 | 8.74(d, 1H), 8.19(d, 1H), 7.97(dt, 1H), 7.56(dd, 1H), 7.13(d, 2H), 7.02(t, 1H), 3.72(q, 2H), 3.41(s, 3H), 1.19(t, 3H) |

In addition, examples of production intermediates of the aryoxyurea compound of the present invention are shown in TABLES 5 to 9. TABLE 5 shows examples of a production intermediate represented by formula (e). TABLE 6 shows examples of a production intermediate represented by formula (f). TABLE 7 shows examples of a production intermediate represented by formula (g). TABLE 8 shows examples of a production intermediate represented by formula (h).

[Chemical formula 24]

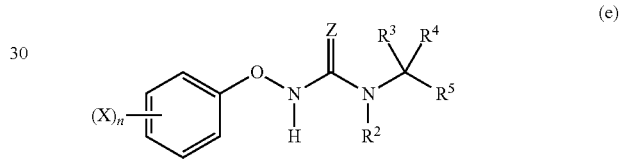

(e)

TABLE 5

| No. | R$^2$ | R$^3$ | R$^4$ | R$^5$ | (X)n | Z | Melting Point (° C) |
|---|---|---|---|---|---|---|---|
| 5-1 | H | Me | Me | Me | 3-Br-6-Cl | O | |
| 5-2 | H | Me | Me | Me | 3-CF$_3$ | O | |
| 5-3 | H | Me | Me | Me | 3-Br-5-Cl | O | |
| 5-4 | H | Me | Me | Me | 2-Cl-5-(3-CF$_3$—Ph) | O | |
| 5-5 | H | Me | Me | Me | 3,5-Cl2 | O | |
| 5-6 | H | Me | Me | Me | 3-OH-4-NO$_2$ | O | |
| 5-7 | H | Me | Me | Me | 4-Ac | O | |
| 5-8 | H | Me | Me | Me | 3-Cl-5-CN | O | |
| 5-9 | H | Me | Me | Me | 3-Cl-5-OMe | O | |
| 5-10 | H | Me | Me | Me | 3-Br-4,5-Cl$_2$ | O | |
| 5-11 | H | Me | Me | Me | 3-Cl-5-(4-Cl—Ph) | O | |
| 5-12 | H | Me | Me | Me | 3-Cl-5-(4-OMe—Ph) | O | |
| 5-13 | H | Me | Me | Me | 4-NO$_2$ | O | |
| 5-14 | H | Me | Me | Me | 3-Br-5-OMe | O | |
| 5-15 | H | Me | Me | Me | 3-Br-5-Me | O | |
| 5-16 | H | Me | Me | Me | 2,4-Cl$_2$ | O | |
| 5-17 | H | Me | Me | Me | 2,5-Me$_2$-4-NO$_2$ | O | |
| 5-18 | H | Me | Me | Me | 3-Br-5-CO$_2$Me | O | |
| 5-19 | H | Me | Me | Me | 2,3,5-Br$_3$ | O | |
| 5-20 | H | Me | Me | Me | 3,5-Br$_2$-4-Cl | O | |
| 5-21 | H | Me | Me | Me | 3,4,5-Br$_3$ | O | |
| 5-22 | H | Me | Me | Me | 3-Br-2-Cl | O | |
| 5-23 | H | Me | Me | Me | 3,5-Br$_2$-4-OMe | O | |
| 5-24 | H | Me | Me | Ph | 3-Br-5-Cl | O | 130-131 |

TABLE 5-continued

| No. | R² | R³ | R⁴ | R⁵ | (X)n | Z | Melting Point (° C) |
|---|---|---|---|---|---|---|---|
| 5-25 | H | Me | Me | Ph | 3,4-Cl₂ | O | |
| 5-26 | H | Me | Me | Ph | 3-Br-5-CF₃ | O | |
| 5-27 | H | Me | Me | Ph | 3,5-Br₂ | O | |
| 5-28 | H | Me | Me | Ph | 3-Br-4,5-Cl₂ | O | |
| 5-29 | H | Me | Me | Ph | 3,5-Cl₂ | O | |
| 5-30 | H | Me | Me | Ph | 3-Br-5-F | O | |
| 5-31 | H | Me | Me | Ph | 3,5-F₂ | O | |
| 5-32 | H | Me | Me | Ph | 3-Br-5-CN | O | |
| 5-33 | H | Me | Me | Ph | 3-Br-5-NO₂ | O | |
| 5-34 | H | Me | Me | Ph | 3-Br-5-SO₂Me | O | |
| 5-35 | H | Me | Me | Ph | 3-Br-5-OMe | O | |
| 5-36 | H | Me | Me | Ph | 4-CF₃ | O | |
| 5-37 | H | Me | Me | Ph | 2,5-Me₂-4-NO₂ | O | |
| 5-38 | H | Me | Me | Ph | 2,3,5-Br₃ | O | |
| 5-39 | H | Me | Me | Ph | 3,4-Br₂ | O | |
| 5-40 | H | Me | Me | Ph | 3-Br-4-Cl | O | |
| 5-41 | H | Me | Me | Ph | 3,5-Br₂-4-Cl | O | |
| 5-42 | H | Me | Me | Ph | 3,4,5-Br₃ | O | |
| 5-43 | H | Me | Me | Ph | 3-Br-2-Cl | O | |
| 5-44 | H | Me | Me | Ph | 5-Br-2-Cl | O | |
| 5-45 | H | Me | Me | Ph | 3-Br-5-CO₂Me | O | |
| 5-46 | H | Me | Me | Ph | — | O | |
| 5-47 | H | Me | Me | Ph | 3-Cl | O | 140-142 |
| 5-48 | H | Me | Me | Ph | 2-Cl | O | 125-127 |
| 5-49 | H | Me | Me | Ph | 2,6-Cl₂ | O | 185-187 |
| 5-50 | H | Me | Me | =N—O | 3-Br-5-Cl | O | 99-101 |
| 5-51 | H | Me | Me | Py-2-yl | 3-Br-5-Cl | O | 163-165 |
| 5-52 | H | Me | Me | Bn | 3-Br-5-Cl | O | |
| 5-53 | H | Me | Me | 3-Me-Ph | 3-Br-5-Cl | O | 153-154 |
| 5-54 | H | Me | Me | 3-CF₃-Ph | 3-Br-5-Cl | O | 138-139 |
| 5-55 | H | Me | Me | 6-Me—Py-2-yl | 3-Br-5-Cl | O | 152-153 |
| 5-56 | H | Me | Me | Py-2-yl | 3,5-Br₂-4-Cl | O | |
| 5-57 | H | Me | Me | CO₂Et | 3-Br-5-Cl | O | 111-113 |
| 5-58 | H | Me | Me | CO₂H | 3-Br-5-Cl | O | |
| 5-59 | H | Me | Me | CN | 3-Br-5-Cl | O | 186-188 |
| 5-60 | H | Me | Me | 3-Me—Py-2-yl | 3-Br-5-Cl | O | 162-164 |
| 5-61 | H | Me | Me | Py-2-yl | 3,5-Cl₂ | O | |
| 5-62 | H | Me | Me | 5-Me—Py-2-yl | 3-Br-5-Cl | O | 147-149 |
| 5-63 | H | Me | Me | 4-Me—Py-2-yl | 3-Br-5-Cl | O | 174-176 |
| 5-64 | H | Me | Me | Py-2-yl | 3,5-Br₂-4-OMe | O | |
| 5-65 | H | Me | Me | Py-2-yl | 3,5-Br₂ | O | |
| 5-66 | H | Me | Me | Py-2-yl | 3,5-Br₂-4-OCHF₂ | O | |
| 5-67 | H | Me | Me | CONHEt | 3-Br-5-Cl | O | |
| 5-68 | H | Me | Me | Py-2-yl | 4-Br-3,5-Cl₂ | O | |
| 5-69 | H | Me | Me | Py-4-yl | 3-Br-5-Cl | O | 199-202 |
| 5-70 | H | Me | Me | 2-Me—Ph | 3-Br-5-Cl | O | 177-179 |
| 5-71 | H | Me | Me | CONEt₂ | 3-Br-5-Cl | O | |
| 5-72 | H | Me | Me | 4-Me—Ph | 3-Br-5-Cl | O | 139-141 |
| 5-73 | H | Me | Me | 2-CF₃—Ph | 3-Br-5-Cl | O | 173-175 |
| 5-74 | H | H | H | Ph | 3-Br-5-Cl | O | 176-177 |
| 5-75 | H | Me | H | Ph | 3-Br-5-Cl | O | 131-132 |
| 5-76 | H | H | H | Py-2-yl | 3-Br-5-Cl | O | 152-153 |
| 5-77 | H | Me | Me | Py-2-yl | 3,5-Br₂-4-F | O | |
| 5-78 | H | Me | Me | 4-CF₃—Ph | 3-Br-5-Cl | O | 182-184 |
| 5-79 | H | Me | Me | Py-2-yl | 3,5-Cl₂-4-Me | O | |
| 5-80 | H | Me | Me | 2-MeO—Ph | 3-Br-5-Cl | O | 162-164 |
| 5-81 | H | Me | Me | Py-3-yl | 3-Br-5-Cl | O | |
| 5-82 | H | Me | Me | CH₂OCH₂CH=CH₂ | 3-Br-5-Cl | O | |
| 5-83 | H | Me | Me | CH₂OEt | 3-Br-5-Cl | O | 88-90 |
| 5-84 | H | Me | Me | CH₂CO₂Et | 3-Br-5-Cl | O | 89-91 |
| 5-85 | H | Me | Me | CH₂CO₂H | 3-Br-5-Cl | O | |
| 5-86 | H | Me | Me | C≡CH | 3-Br-5-Cl | O | 144-146 |
| 5-87 | H | Me | Me | CH₂CONHEt | 3-Br-5-Cl | O | |
| 5-88 | H | Me | Me | CON(Me)₂ | 3-Br-5-Cl | O | |
| 5-89 | H | Me | Me | CONHCH₂CH₂OMe | 3-CH₂CH₂SO₂-4 | O | |
| 5-90 | H | Me | Me | Me | 4-MeSO₂ | O | |
| 5-91 | H | Me | Me | Me | 3-Br-5-Cl | O | |
| 5-92 | H | Me | Me | CONHMe | 3-Br-5-Cl | O | |
| 5-93 | H | Me | Me | CH₂O(Py-2-yl) | 3-Br-5-Cl | O | 124-126 |

TABLE 5-continued

[Structure: (X)n-phenyl-O-N(H)-C(=Z)-N(R²)-C(R³)(R⁴)(R⁵)]

| No. | R² | R³ | R⁴ | R⁵ | (X)n | Z | Melting Point (°C) |
|---|---|---|---|---|---|---|---|
| 5-94 | H | Me | Me | CONH$^i$Pr | 3-Br-5-Cl | O | |
| 5-95 | H | Me | Me | CO(Piperidin-1-yl) | 3-Br-5-Cl | O | |
| 5-96 | H | Me | Me | CONHPh | 3-Br-5-Cl | O | |
| 5-97 | H | Me | Me | CONH | 3-Br-5-Cl | O | |
| 5-98 | H | Me | Me | CONHCH$_2$CF$_3$ | 3-Br-5-Cl | O | |
| 5-99 | H | Me | Me | CONHCH$_2$$^c$Pr | 3-Br-5-Cl | O | |
| 5-100 | H | Me | Me | CONHBn | 3-Br-5-Cl | O | |
| 5-101 | H | Me | Me | CH$_2$NHCO$_2$Et | 3-Br-5-Cl | O | 121-124 |
| 5-102 | H | Me | Me | CONHCH$_2$C≡CH | 3-Br-5-Cl | O | |
| 5-103 | H | Me | Me | CH=N—OBn | 3-Br-5-Cl | O | 106-108 |
| 5-104 | H | Bn | H | CO$_2$Me | 3-Br-5-Cl | O | 119-121 |
| 5-105 | H | Me | Me | CH$_2$NHAc | 3-Br-5-Cl | O | 181-183 |
| 5-106 | H | Me | Me | CH$_2$NHCOPh | 3-Br-5-Cl | O | 114-117 |
| 5-107 | H | Me | Me | CONH$^c$Pr | 3-Br-5-Cl | O | |
| 5-108 | H | Me | Me | CONH$^c$Pen | 3-Br-5-Cl | O | |
| 5-109 | H | Me | H | CO$_2$Me | 3-Br-5-Cl | O | 140-142 |
| 5-110 | H | Me | Me | CO$_2$Et | 4-Br-3,5-Cl$_2$ | O | 142-144 |
| 5-111 | H | Me | Me | CO$_2$H | 4-Br-3,5-Cl$_2$ | O | |
| 5-112 | H | Me | Me | CONH$^s$Bu | 3-Br-5-Cl | O | |
| 5-113 | H | Me | Me | CONHCH$_2$CF$_3$ | 4-Br-3,5-Cl$_2$ | O | |
| 5-114 | H | Me | Me | CONH$^i$Pr | 4-Br-3,5-Cl$_2$ | O | |
| 5-115 | H | Me | Me | CONH$^c$Hex | 3-Br-5-Cl | O | |
| 5-116 | H | Me | Me | CONH$^t$Bu | 3-Br-5-Cl | O | |
| 5-117 | H | Me | H | CO$_2$H | 3-Br-5-Cl | O | |
| 5-118 | H | Me | Me | C(Me)=N—OMe | 3-Br-5-Cl | O | 146-147 |
| 5-119 | H | Me | H | CONH$^i$Pr | 3-Br-5-Cl | O | |
| 5-120 | H | Me | H | CONHCH$_2$CF$_3$ | 3-Br-5-Cl | O | |
| 5-121 | H | Me | Me | $^c$Hex | 3-Br-5-Cl | O | |
| 5-122 | H | Me | Me | Et | 3-Br-5-Cl | O | 87-88 |
| 5-123 | H | Me | Me | C(Me)=N—OCH$_2$$^c$Pr | 3-Br-5-Cl | O | 154-155 |
| 5-124 | H | Me | Me | C(Me)=N—OBn | 3-Br-5-Cl | O | 107-108 |
| 5-125 | H | Me | Me | $^n$Hex | 3-Br-5-Cl | O | |
| 5-126 | H | Me | Me | $^t$Bu | 3-Br-5-Cl | O | |
| 5-127 | H | Me | Me | CONHCH$_2$CF$_3$ | 3,4-Cl$_2$ | O | amo |
| 5-128 | H | Me | Me | CO$_2$Et | 3,4-Cl$_2$ | O | |
| 5-129 | H | Me | Me | CO$_2$H | 3,4-Cl$_2$ | O | |
| 5-130 | H | Me | Me | CONH$^i$Pr | 3,4-Cl$_2$ | O | |
| 5-131 | H | —CH$_2$CH$_2$— | | Ph | 3-Br-5-Cl | O | 196-198 |
| 5-132 | H | —(CH$_2$)$_4$— | | Ph | 3-Br-5-Cl | O | 145-147 |
| 5-133 | H | —(CH$_2$)$_5$— | | Ph | 3-Br-5-Cl | O | 184-186 |
| 5-134 | H | $^i$Pr | H | Ph | 3-Br-5-Cl | O | 122-124 |
| 5-135 | H | Ph | H | Ph | 3-Br-5-Cl | O | 184-186 |
| 5-136 | H | Ph | Me | Ph | 3-Br-5-Cl | O | 190-192 |
| 5-137 | H | Et | Et | Ph | 3-Br-5-Cl | O | 167-169 |
| 5-138 | H | Me | Me | 2-F—Ph | 3-Br-5-Cl | O | 109-111 |
| 5-139 | H | Me | Me | Py-2-yl | 3,4-Cl$_2$ | O | |
| 5-140 | H | Me | Me | Py-2-yl | 3,5-Br$_2$-4-CF$_3$CH$_2$O | O | |
| 5-141 | H | Me | Me | Py-2-yl | 3,5-Br$_2$-4-$^n$HexO | O | |
| 5-142 | H | Me | Me | Py-2-yl | 3,5-Cl$_2$-4-Ph | O | |
| 5-143 | H | Me | CN | Py-2-yl | 3-Br-5-Cl | O | 214-215 |
| 5-144 | H | —CH$_2$CH$_2$— | | Py-2-yl | 3-Br-5-Cl | O | 172-174 |
| 5-145 | H | Me | Me | Py-2-yl | 3-Cl-4-CN | O | |
| 5-146 | H | Me | Me | Py-2-yl | 4-MeSO$_2$ | O | |
| 5-147 | H | Me | Me | Py-2-yl | 3-Cl-4-Ac | O | |
| 5-148 | H | Me | Me | Py-2-yl | 3-Cl-4-CHO | O | |
| 5-149 | H | Me | Me | Py-2-yl | 3-Cl-4-CO$_2$Me | O | |
| 5-150 | H | Me | Me | Py-2-yl | 3-Cl-4-CO$_2$H | O | |
| 5-151 | H | Me | Me | Py-2-yl | 3-Cl-4-CHF$_2$ | O | |
| 5-152 | H | Me | Me | Py-2-yl | 3,4,5-Cl$_3$ | O | |
| 5-153 | H | Me | Me | Py-2-yl | 3-Cl-4-Br | O | |
| 5-154 | H | Me | Me | 4-MeO—Py-2-yl | 3-Br-5-Cl | O | 150-152 |
| 5-155 | H | Me | Me | Py-2-yl | 3-Cl-4-NO$_2$ | O | |
| 5-156 | H | Me | Me | Py-2-yl | 3-Br-5-I | O | |
| 5-157 | H | Me | Me | Py-2-yl | 3-Br-5-F | O | |
| 5-158 | H | Me | Me | Py-2-yl | 3-Me-4-NO$_2$ | O | |
| 5-159 | H | Me | Me | 4-CF$_3$—Py-2-yl | 3-Br-5-Cl | O | 129-131 |
| 5-160 | H | Me | Me | Py-2-yl | 3-Br-4,5-Cl$_2$ | O | |
| 5-161 | H | Me | Me | Py-2-yl | 3-Cl-5-CN | O | |
| 5-162 | H | Me | Me | Py-2-yl | 3,4-Br$_2$-5-Cl | O | |

TABLE 5-continued

| No. | R² | R³ | R⁴ | R⁵ | (X)n | Z | Melting Point (° C) |
|---|---|---|---|---|---|---|---|
| 5-163 | H | Me | Me | Py-2-yl | 3,5-Cl₂-4-CN | O | |
| 5-164 | H | Me | Me | Py-2-yl | 3-Cl-5-CF₃ | O | |
| 5-165 | H | Me | Me | Py-2-yl | 3-Br-5-MeO | O | |
| 5-166 | H | Me | Me | Py-2-yl | 3,4-Br₂ | O | |
| 5-167 | H | Me | Me | Py-2-yl | 3,4-Br₂-6-F | O | |
| 5-168 | H | Me | Me | Py-2-yl | — | O | 124-126 |
| 5-169 | H | Me | Me | Py-2-yl | 2-Cl-4-CF₃ | O | 59-61 |
| 5-170 | H | Me | Me | Py-2-yl | 3-Cl-4-Me | O | 156-158 |
| 5-171 | H | Me | Me | Py-2-yl | 2-CF₃-4-Cl | O | 123-125 |
| 5-172 | H | Me | Me | Py-2-yl | 3-F-4-Cl | O | 132-134 |
| 5-173 | H | Me | Me | Py-2-yl | 3-Br-6-Cl | O | |
| 5-174 | H | Me | Me | 4-Ph—Py-2-yl | 3-Br-5-Cl | O | 130-132 |
| 5-175 | H | Me | Me | Py-2-yl | 3-Me-4-Cl | O | 153-155 |
| 5-176 | H | Me | Me | Py-2-yl | 3,5-(CF₃)₂ | O | |
| 5-177 | H | Me | Me | 6-F—Py-2-yl | 3-Br-5-Cl | O | |
| 5-178 | H | Me | Me | 6-Cl—Py-2-yl | 3-Br-5-Cl | O | 108-110 |
| 5-179 | H | Me | Me | 3-F—Py-2-yl | 3-Br-5-Cl | O | |
| 5-180 | H | Me | Me | 6-Cl—Py-2-yl | 4-Br-3,5-Cl₂ | O | 160-162 |
| 5-181 | H | Me | Me | 5-F-Py-2-yl | 3-Br-5-Cl | O | |
| 5-182 | H | Me | Me | Thiophen-2-yl | 3-Br-5-Cl | O | 132-134 |
| 5-183 | H | Me | Me | Furan-2-yl | 3-Br-5-Cl | O | |
| 5-184 | H | Me | Me | Thiazol-2-yl | 3-Br-5-Cl | O | |
| 5-185 | H | Me | Me | Pyrazin-2-yl | 3-Br-5-Cl | O | 152-154 |
| 5-186 | H | Me | Me | Pyrimidin-2-yl | 3-Br-5-Cl | O | |
| 5-187 | H | Me | Me | [1,2,4]Oxadiazol-3-yl | 3-Br-5-Cl | O | 196-197 |
| 5-188 | H | Me | Me | 4-Me-thiazol-2-yl | 3-Br-5-Cl | O | |
| 5-189 | H | Me | Me | Pyrimidin-4-yl | 3-Br-5-Cl | O | 166-167 |
| 5-190 | H | Me | Me | 1H-Pyrazol-3-yl | 3-Br-5-Cl | O | |
| 5-191 | H | Me | Me | 1-Me-1H-pyrazol-3-yl | 3-Br-5-Cl | O | 160-161 |
| 5-192 | H | Me | Me | 1-Me-1H-pyrazol-5-yl | 3-Br-5-Cl | O | |
| 5-193 | H | Me | Me | Isoxazol-5-yl | 3-Br-5-Cl | O | |
| 5-194 | H | Me | Me | 4-Et-thiazol-2-yl | 3-Br-5-Cl | O | 117-119 |
| 5-195 | H | Me | Me | 4,5-Me₂-thiazol-2-yl | 3-Br-5-Cl | O | 136-138 |
| 5-196 | H | Me | Me | 1-ᵗBu-1H-pyrazol-3-yl | 3-Br-5-Cl | O | |
| 5-197 | H | Me | Me | 1-CF₃CH₂-1H-pyrazol-5-yl | 3-Br-5-Cl | O | |
| 5-198 | H | Me | Me | [1,2,4]Triazin-3-yl | 3-Br-5-Cl | O | 196-197 |
| 5-199 | H | Me | Me | 1-Et-1H-[1,2,4]triazin-3-yl | 3-Br-5-Cl | O | |
| 5-200 | H | Me | Me | Pyridazin-3-yl | 3-Br-5-Cl | O | amo |
| 5-201 | H | Me | Me | 2-Me-2H-tetrazol-5yl | 3-Br-5-Cl | O | 130-131 |
| 5-202 | H | Me | Me | Pyrimidin-2-yl | 4-Br-3,5-Cl₂ | O | |
| 5-203 | H | Me | Me | 4,5-Dihydro-oxazol-2-yl | 3-Br-5-Cl | O | 183-185 |
| 5-204 | H | Me | Me | 5-Me-Pypyrimidin-2-yl | 3-Br-5-Cl | O | 183-184 |
| 5-205 | H | Me | Me | Pyrimidin-2-yl | 3,4-Cl₂ | O | |
| 5-206 | H | Me | Me | 4,5-Me₂-thiazol-2-yl | 4-Br-3,5-Cl₂ | O | 174-175 |
| 5-207 | H | Me | Me | 4,5-Me₂-thiazol-2-yl | 3,4-Cl₂ | O | 170-171 |
| 5-208 | H | Me | Me | 4-Me-Pyrimidin-2-yl | 3-Br-5-Cl | O | |
| 5-209 | H | Me | Me | 4-Me-Pyrimidin-2-yl | 4-Br-3,5-Cl₂ | O | |
| 5-210 | H | Me | Me | Py-2-yl | 3-Cl-4-(Py-2-yl) | O | |
| 5-211 | H | Me | Me | Quinolin-2-yl | 3-Br-5-Cl | O | 129-131 |

[Chemical formula 25]

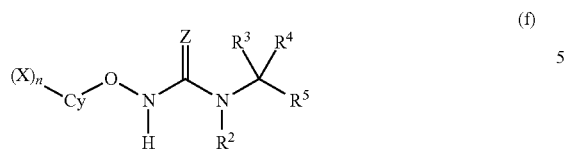

(f)

TABLE 6

| No. | R² | R³ | R⁴ | R⁵ | Cy | (X)n | Z | Melting Point (°C.) |
|---|---|---|---|---|---|---|---|---|
| 6-1 | H | Me | Me | Me | Quinolin-6-yl | 3-Br | O | 160-179 |
| 6-2 | H | Me | Me | Me | Quinolin-6-yl | — | O | |
| 6-3 | H | Me | Me | Me | Quinolin-7-yl | 6-OMe | O | |
| 6-4 | H | Me | Me | Me | Quinolin-6-yl | 3-Br-7-F | O | |
| 6-5 | H | Me | Me | $CH_2OCH_2CH=CH_2$ | Quinolin-6-yl | 3-Br | O | |
| 6-6 | H | Me | Me | C≡CMe | Quinolin-6-yl | 3-Br | O | |
| 6-7 | H | Me | Me | Me | Quinolin-2-yl | — | O | |
| 6-8 | H | Me | Me | Ph | Quinolin-6-yl | 3-Br | O | |
| 6-9 | H | Me | Me | CH=N—OMe | Quinolin-6-yl | 3-Br | O | |
| 6-10 | H | Me | Me | Me | Quinolin-4-yl | 7-Cl | O | |
| 6-11 | H | Me | Me | Py-2-yl | Quinolin-6-yl | 3-Br | O | |
| 6-12 | H | Me | Me | Bn | Quinolin-6-yl | 3-Br | O | |
| 6-13 | H | Me | Me | Me | Pyrimidin-2-yl | 4-CF₃ | O | |
| 6-14 | H | Me | Me | Me | Pyrimidin-4-yl | 6-CF₃ | O | |
| 6-15 | H | Me | Me | Me | Pyrimidin-4-yl | 2-CF₃ | O | |
| 6-16 | H | Me | Me | Ph | Pyrimidin-2-yl | 4,6-Me₂ | O | |
| 6-17 | H | Me | Me | Me | Py-2-yl | 6-CF₃ | O | |
| 6-18 | H | Me | Me | Me | Py-2-yl | 6-Cl-5-CN-4-Me | O | |
| 6-19 | H | Me | Me | Me | Py-2-yl | 6-Cl-3-CN-4-Me | O | |
| 6-20 | H | Me | Me | Me | Py-4-yl | 2,6-Cl₂ | O | |
| 6-21 | H | Me | Me | Ph | Py-2-yl | 4-CF₃ | O | |
| 6-22 | H | Me | Me | Ph | Py-2-yl | 6-Cl-4-CF₃ | O | |
| 6-23 | H | Me | Me | Ph | Py-2-yl | 6-Br | O | |
| 6-24 | H | Me | Me | Py-2-yl | Py-2-yl | 6-Cl-4-CF₃ | O | |
| 6-25 | H | Me | Me | Me | Pyridazin-3-yl | 6-CF₃ | O | |
| 6-26 | H | Me | Me | Ph | Pyridazin-3-yl | 6-CF₃ | O | |
| 6-27 | H | Me | Me | Ph | Pyridazin-3-yl | 6-Cl | O | |
| 6-28 | H | Me | Me | Ph | Naphthalen-2-yl | — | O | 125-127 |
| 6-29 | Ac | Me | Me | Me | Quinolin-6-yl | 3-Br | O | 166-168 |
| 6-30 | H | Me | Me | Me | Quinolin-3-yl | — | O | |
| 6-31 | H | Me | Me | Py-2-yl | Quinolin-3-yl | — | O | |
| 6-32 | H | Me | Me | Me | Quinolin-4-yl | — | O | |
| 6-33 | H | Me | Me | Py-2-yl | Quinolin-4-yl | — | O | |
| 6-34 | H | Me | Me | Py-2-yl | Quinoxalin-2-yl | — | O | |
| 6-35 | H | Me | Me | Py-2-yl | Quinolin-6-yl | — | O | 149-151 |
| 6-36 | H | Me | Me | Py-2-yl | Quinolin-2-yl | — | O | |
| 6-37 | H | Me | Me | Py-2-yl | Quinoxalin-6-yl | — | O | |
| 6-38 | H | Me | Me | Me | Isoquinolin-6-yl | — | O | |
| 6-39 | H | Me | Me | Py-2-yl | Isoquinolin-6-yl | — | O | |
| 6-40 | H | Me | Me | Py-2-yl | Quinolin-6-yl | 2-Me | O | |
| 6-41 | H | Me | Me | Py-2-yl | Quinolin-6-yl | 3-Me | O | |
| 6-42 | H | Me | Me | Py-2-yl | Isoquinolin-1-yl | 3-Cl | O | |
| 6-43 | H | Me | Me | Py-2-yl | Py-3-yl | 5-Br | O | |
| 6-44 | H | Me | Me | Py-2-yl | Py-2-yl | 5-CF₃-6-Cl | O | |
| 6-45 | H | Me | Me | Py-2-yl | Py-2-yl | 3-Cl-5-CF₃ | O | amo |
| 6-46 | H | Me | Me | Py-2-yl | Py-2-yl | 4-CO₂-Me-6-Cl | O | |
| 6-47 | H | Me | Me | Py-2-yl | Py-4-yl | 2,6-Cl₂ | O | |
| 6-48 | H | Me | Me | Py-2-yl | Py-2-yl | 4-Me-6-Cl | O | |
| 6-49 | H | Me | Me | Py-2-yl | Py-2-yl | 4-MeO-6-Cl | O | |
| 6-50 | H | Me | Me | Py-2-yl | Py-2-yl | 4-CN-6-Cl | O | |
| 6-51 | H | Me | Me | Py-2-yl | Py-2-yl | 6-Cl | O | |
| 6-52 | H | Me | Me | Pyrimidin-2-yl | Py-2-yl | 4-CF₃-6-Cl | O | 139-140 |
| 6-53 | H | Me | Me | 4,5-Me₂-thiazol-2-yl | Py-2-yl | 4-CF₃-6-Cl | O | 138-139 |

TABLE 6-continued

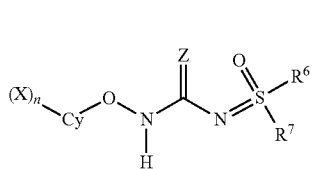

| No. | R² | R³ | R⁴ | R⁵ | Cy | (X)n | Z | Melting Point (° C.) |
|---|---|---|---|---|---|---|---|---|
| 6-54 | H | Me | Me | Py-2-yl | Py-4-yl | 2-Br-6-Me | O | |
| 6-55 | H | Me | Me | Py-2-yl | Py-4-yl | 4-CF₃ | O | |
| 6-56 | H | Me | Me | Py-2-yl | Py-4-yl | 2,6-Br₂ | O | |
| 6-57 | H | Me | Me | Pyrimidin-2-yl | Py-2-yl | 4,6-Cl₂ | O | 178-179 |
| 6-58 | H | Me | Me | Pyrimidin-2-yl | Py-4-yl | 2,6-Cl₂ | O | 155-156 |
| 6-59 | H | Me | Me | Py-2-yl | Py-2-yl | 4,6-Cl₂ | O | 136-137 |
| 6-60 | H | Me | Me | Py-2-yl | Py-4-yl | 2-Br-6-Cl | O | |
| 6-61 | H | Me | Me | Py-2-yl | Py-4-yl | 2-Cl | O | |
| 6-62 | H | Me | Me | Py-2-yl | Py-4-yl | 2-Cl-6-N(Me)₂ | O | |
| 6-63 | H | Me | Me | Py-2-yl | Py-2-yl | 4-CF₃-6-ⁱPr | O | |
| 6-64 | H | Me | Me | Py-2-yl | Py-4-yl | 2-CN-6-Me | O | |
| 6-65 | H | Me | Me | Py-2-yl | Pyrimidin-4-yl | 2-Me-6-Cl | O | |
| 6-66 | H | Me | Me | Py-2-yl | Pyrimidin-4-yl | 2,6-Cl₂ | O | |
| 6-67 | H | Me | Me | Py-2-yl | Py-3-yl | 5,6-Cl₂ | O | 111-113 |
| 6-68 | H | Me | Me | Py-2-yl | Py-4-yl | 2-Br-6-CF₃ | O | |
| 6-69 | H | Me | Me | Py-2-yl | Py-2-yl | 4-Br-6-CF₃ | O | |
| 6-70 | H | Me | Me | Py-2-yl | Py-3-yl | 6-Cl | O | 124-126 |
| 6-71 | H | Me | Me | Pyrimidin-2-yl | Py-3-yl | 6-Cl | O | 120-122 |

[Chemical formula 26]

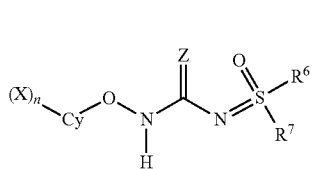

(g)

TABLE 7

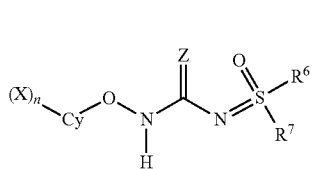

| No. | R⁶ | R⁷ | Cy | (X)n | Z | Melting Point (° C.) |
|---|---|---|---|---|---|---|
| 7-1 | Me | Me | Ph | 3-Br-5-Cl | O | |
| 7-2 | —C₄H₈— | | Ph | 3-Br-5-Cl | O | 137-139 |
| 7-3 | Me | Ph | Ph | 3-Br-5-Cl | O | 127-129 |
| 7-4 | Me | Py-2-yl | Ph | 3-Br-5-Cl | O | 158-160 |
| 7-5 | Me | ⁿBu | Ph | 3-Br-5-Cl | O | 114-116 |
| 7-6 | Me | Ph | Ph | 4-Br-3,5-Cl₂ | O | 193-195 |

[Chemical formula 27]

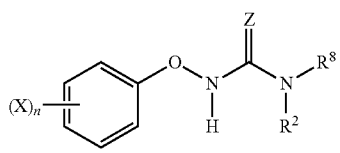

(h)

TABLE 8

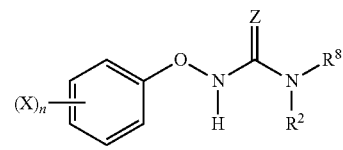

| No. | R² | R⁸ | (X)n | Z | Melting Point (° C.) |
|---|---|---|---|---|---|
| 8-1 | Me | Ph | 3-Br-5-Cl | O | 124-126 |
| 8-2 | H | Ph | 3-Br-5-Cl | O | 174-176 |
| 8-3 | H | Indan-1-yl | 3-Br-5-Cl | O | 192-193 |
| 8-4 | H | 1,2,3,4-Tetrahydro-naphthalen-1-yl | 3-Br-5-Cl | O | 181-184 |
| 8-5 | H | 5,6,7,8-Tetrahydro-quinolin-8-yl | 3-Br-5-Cl | O | 193- |
| 8-6 | H | 2-Ph—ᶜPr | 3-Br-5-Cl | O | 169-171 |
| 8-7 | H | Quinolin-8-yl | 3-Br-5-Cl | O | 188-189 |
| 8-8 | H | CO₂Et | 3-Br-5-Cl | O | 171-173 |

TABLE 9

| No. | Structure | Melting Point (° C.) |
|---|---|---|
| 9-1 | 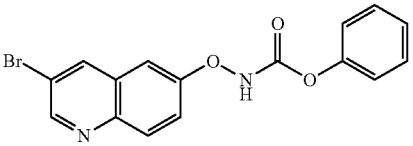 [SMILES: O=C(NOc1ccc2ncc(Br)cc2c1)Oc1ccccc1] | 118-120 |
| 9-2 | 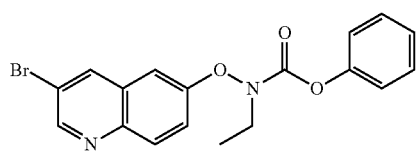 [SMILES: CCN(Oc1ccc2ncc(Br)cc2c1)C(=O)Oc1ccccc1] | amo |

TABLE 9-continued

| No. | Structure | Melting Point (° C.) |
|---|---|---|
| 9-3 | Br-, Cl, phenyl carbamate structure | 127-129 |
| 9-4 | methoxy urea pyridine structure | vis |
| 9-5 | HO-urea pyridine structure | 73-75 |
| 9-6 | HO-urea tert-butyl structure | 59-61 |
| 9-7 | Br, Cl-pyridyl phenyl carbamate structure | 131-133 |

Among the compounds shown in TABLES 5-9, $^1$H-NMR (CDCl$_3$) was measured for the following compounds. The measurement results are shown below.

| No. | $^1$H-NMR(CDCl$_3$, δ ppm) |
|---|---|
| 5-127 | 7.64~7.45(br, 1H), 7.39(d, 1H), 7.31(d, 1H), 7.02(dd, 1H), 6.90(br, 1H), 6.02(br, 1H), 3.96~3.88(m, 2H), 1..59(s, 6H) |
| 6-45 | 8.73(br, 1H), 8.48~8.45(m, 2H), 8.38(d, 1H), 7.95(br, 1H), 7.71(t, 1H), 7.37(d, 1H), 7.18(dd, 1H), 1.75(s, 6H) |
| 9-4 | 8.52(dd, 1H), 7.75(br, 1H), 7.66(t, 1H), 7.40(d, 1H), 7.16(dd, 1H), 3.73(s, 3H), 3.51(q, 2H), 1.75(s, 6H), 1.13(t, 3H) |

Some preparation examples of the pest control agent according to the present invention are shown below. However, additives and addition ratios are not limited to the preparation examples, and can be modified over a wide range. Moreover, the term "parts" used in the preparation examples indicates "weight parts." The following are the preparation examples for agricultural and horticultural use.

Preparation Example 1

Wettable Powder

| | |
|---|---|
| Compound of the present invention | 40 parts |
| Diatom earth | 53 parts |
| Fatty alcohol sulfate | 4 parts |
| Alkylnaphtalene sulfonate | 3 parts |

The foregoing is uniformly mixed and finely pulverized to obtain a wettable powder including 40% of active ingredient.

Preparation Example 2

Emulsion

| | |
|---|---|
| Compound of the present invention | 30 parts |
| Xylene | 33 parts |
| Dimethylform amid | 30 parts |
| Polyoxyethylene alkylallyl ether | 7 parts |

The foregoing is mixed and dissolved to obtain an emulsion including 30% of active ingredient.

The following are the preparation examples for epidemic-prevention and animals.

Preparation Example 3

Granulated Powder

| | |
|---|---|
| Compound of the present invention | 5 parts |
| Kaolin | 94 parts |
| White carbon | 1 part |

The compound of the present invention was dissolved in an organic solvent, and sprayed on a carrier, followed by evaporating the solvent under reduced pressure. This kind of granulated powder may be mixed with animal food.

Preparation Example 4

Impregnating Agent

| | |
|---|---|
| Compound of the present invention | 0.1-1 parts |
| Peanut oil | balance |

The impregnating agent is filter sterilized by a sterilizing filter after adjustment.

Preparation Example 5

Pour-on Agent

| | |
|---|---|
| Compound of the present invention | 5 parts |
| Myristic acid ester | 10 parts |
| Isopropanol | balance |

Preparation Example 6

Spot-on Agent

| | |
|---|---|
| Compound of the present invention | 10-15 parts |
| Palmitic acid ester | 10 parts |
| Isopropanol | balance |

Preparation Example 7

Spray-on Agent

| | |
|---|---|
| Compound of the present invention | 1 part |
| Propylene glycol | 10 parts |
| Isopropanol | balance |

[Experiments with Animals]

The following test examples demonstrate that the compound of the present invention is useful as an active ingredient of acaricide.

Test Example 1

Efficacy Test Against *Tetranychus urticae*

Ten organic phosphorous-resistant adult female *Tetranychus urticae acarus* were inoculated onto the first leaves of a kidney bean plant planted in a No. 3 pot 7 to 10 days after germination. Next, an emulsion was prepared having the formula indicated in the aforementioned Preparation example 2. This emulsion was diluted with water to a compound concentration of 125 ppm after which the diluted liquids were sprayed onto the kidney bean plant. The kidney bean plant was then placed in a temperature-controlled room at a temperature of 25° C. and humidity of 65%. The life and death of the adult insects were investigated 3 days after the spraying. The development from eggs laid to adult was investigated 14 days after the spraying.

The aforementioned test was carried out on the emulsions containing the Compound No. 1-3, 1-10, 1-20, 1-21, 1-24, 1-25, 1-26, 1-27, 1-28, 1-29, 1-30, 1-39, 1-41, 1-42, 1-50, 1-51, 1-54, 1-55, 1-56, 1-57, 1-60, 1-61, 1-62, 1-63, 1-65, 1-66, 1-67, 1-68, 1-71, 1-94, 1-96, 1-97, 1-98, 1-99, 1-101, 1-102, 1-103, 1-108, 1-109, 1-110, 1-111, 1-114, 1-116, 1-118, 1-119, 1-120, 1-121, 1-122, 1-124, 1-125, 1-126, 1-129, 1-130, 1-132, 1-133, 1-134, 1-135, 1-136, 1-137, 1-138, 1-140, 1-149, 1-152, 1-160, 1-161, 1-171, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-196, 1-197, 1-198, 1-199, 1-200, 1-201, 1-202, 1-203, 1-204, 1-205, 1-206, 1-207, 1-209, 1-211, 1-212, 1-213, 1-214, 1-215, 1-216, 1-217, 1-218, 1-220, 1-221, 1-222, 1-223, 1-224, 1-226, 1-227, 1-228, 1-229, 1-230, 1-232, 1-233, 1-234, 1-235, 1-236, 1-237, 2-1, 2-2, 2-4, 2-6, 2-7, 2-8, 2-10, 2-11, 2-13, 2-24, 2-26, 2-33, 2-37, 2-39, 2-40, 2-42, 2-44, 2-46, 2-47, 2-50, 2-51, 2-52, 2-53, 2-55, 2-56, 2-57, 2-58, 2-59, 2-60, 2-61, 2-62, 2-63, 2-64, 2-65, 2-66, 2-67, 2-68, 2-71, 2-72, 3-3, and 3-22. As a result, the insect mortality rates for all of the compounds in the case of diluting to a concentration of 125 ppm were 90% or higher.

Test Example 2

Efficacy Test Against *Panonychus citri*

Eight adult female *Panonychus citri acarus* from Kanagawa Prefecture were inoculated onto a mandarin orange leaf placed in a Petri dish. Next, an emulsion was prepared having the formula indicated in the aforementioned Preparation example 2. This emulsion was diluted with water to a compound concentration of 125 ppm after which the diluted liquids were sprayed onto the mandarin orange leaf with a rotary spraying tower. The mandarin orange leaf was then placed in a temperature-controlled room at a temperature of 25° C. and a humidity of 65%. The life and death of the adult insects were investigated 3 days after the spraying. The development from eggs laid to adult was investigated 10 days after the spraying.

The aforementioned test was carried out on the emulsions containing the Compound No. 1-3, 1-8, 1-10, 1-24, 1-50, 1-110, 1-111, 1-114, 1-116, 1-119, 1-120, 1-121, 1-122, 1-123, 1-124, 1-129, 1-134, 1-135, 1-149, 1-152, 1-161, 1-171, 1-177, 1-178, 1-179, 1-180, 1-181, 1-182, 1-183, 1-184, 1-185, 1-186, 1-187, 1-188, 1-189, 1-190, 1-192, 1-193, 1-194, 1-197, 1-199, 1-200, 1-201, 1-202, 1-204, 1-205, 1-206, 1-207, 1-209, 1-211, 1-212, 1-213, 1-214, 1-215, 1-216, 1-218, 1-220, 1-222, 1-224, 1-227, 1-229, 1-230, 1-233, 1-234, 1-235, 1-236, 1-237, 2-1, 2-2, 2-4, 2-6, 2-7, 2-10, 2-11, 2-21, 2-33, 2-37, 2-39, 2-40, 2-44, 2-50, 2-51, 2-52, 2-53, 2-55, 2-56, 2-57, 2-59, 2-60, 2-61, 2-62, 2-63, 2-64, 2-65, 2-66, 2-67, 2-68, and 2-71. As a result, the insect mortality rates for all of the compounds in the case of diluting to a concentration of 125 ppm were 90% or higher.

Test Example 3

Efficacy Test Against *Panonychus citri*

Eight acaricide-resistant adult female *Panonychus citri acarus* from Wakayama Prefecture were inoculated onto a mandarin orange leaf placed in a Petri dish. Next, an emulsion was prepared having the formula indicated in the aforementioned Preparation example 2. This emulsion was diluted with water to a compound concentration of 125 ppm after which the diluted liquids were sprayed onto the mandarin orange leaf with a rotary spraying tower. The mandarin orange leaf was then placed in a temperature-controlled room at a temperature of 25° C. and a humidity of 65%. The life and death of the adult insects were investigated 3 days after the spraying. The development from eggs laid to adult was investigated 10 days after the spraying.

The aforementioned test was carried out on the emulsions containing the Compound No. 1-20, 1-26, 1-27, 1-28, 1-29, 1-35, 1-41, 1-42, 1-51, 1-60, 1-61, 1-63, 1-65, 1-66, 1-67, 1-68, 1-98, 1-99, 1-101, 1-116, 1-124, 1-161, 1-186, 1-189, 1-230, 2-8, 2-13, 2-26, and 2-50. As a result, the insect mortality rates for all of the compounds in the case of diluting to a concentration of 125 ppm were 90% or higher.

Test Example 4

Efficacy Test Against *Tetranychus kanzawai*

Ten adult female *Tetranychus kanzawai acarus* from Okayama Prefecture were inoculated onto the first leaves of a kidney bean plant planted in a No. 3 pot 7 to 10 days after germination. Next, an emulsion was prepared having the formula indicated in the aforementioned Preparation example 2. This emulsion was diluted with water to a compound concentration of 500 ppm or 125 ppm after which the diluted liquids were sprayed onto the kidney bean plant. The kidney bean plant was then placed in a temperature-controlled room at a temperature of 25° C. and humidity of 65%. The life and death of the adult insects were investigated 3 days after the spraying. The development from eggs laid to adult was investigated 14 days after the spraying.

The aforementioned test was carried out on the emulsions containing the Compound No. 1-8, 1-10, 1-11, 1-13, 1-16, 1-19, 1-20, 1-21, 1-24, 1-26, 1-27, 1-28, 1-29, 1-30, 1-41, 1-42, 1-43, 1-46, 1-47, 1-48, 1-56, 1-57, 1-58, 1-60, 1-61, 1-62, 1-63, 1-67, 1-66, 1-71, 1-74, 1-80, 1-94, 1-95, 1-96, 1-98, 1-100, 1-102, 1-104, 1-106, 1-108, 1-109, 1-110, 1-111, 1-115, 1-118, 1-119, 1-121, 1-122, 1-123, 1-124, 1-125, 1-126, 1-127, 1-131, 1-140, 1-144, 1-209, 1-212, 1-218, 1-220, 1-224, 1-225, 1-232, 1-234, 1-235, 1-236, 2-12, 2-22, 2-23, 2-24, 2-34, 2-41, 2-47, 2-55, 2-56, 3-2, 3-3, 3-4, and 4-5. As a result, the insect mortality rates for all of the compounds in the case of diluting to a concentration of 500 ppm were 90% or higher.

The aforementioned test was carried out on the emulsions containing the Compound No. 1-3, 1-25, 1-39, 1-40, 1-50, 1-51, 1-53, 1-55, 1-64, 1-65, 1-66, 1-68, 1-93, 1-97, 1-99, 1-101, 1-103, 1-114, 1-116, 1-120, 1-129, 1-130, 1-132, 1-135, 1-136, 1-137, 1-149, 1-150, 1-152, 1-161, 1-162, 1-171, 1-177, 1-178, 1-179, 1-181, 1-182, 1-183, 1-184, 1-185, 1-186, 1-187, 1-188, 1-189, 1-190, 1-191, 1-192, 1-193, 1-194, 1-196, 1-197, 1-198, 1-199, 1-200, 1-201, 1-202, 1-203, 1-204, 1-205, 1-206, 1-207, 1-211, 1-213, 1-214, 1-215, 1-216, 1-222, 1-223, 1-226, 1-227, 1-228, 1-229, 1-230, 1-233, 1-237, 2-5, 2-6, 2-8, 2-10, 2-13, 2-21, 2-26, 2-33, 2-37, 2-39, 2-40, 2-42, 2-44, 2-46, 2-50, 2-51, 2-52, 2-53, 2-57, 2-58, 2-59, 2-60, 2-61, 2-62, 2-63, 2-64, 2-65, 2-66, 2-67, 2-68, 2-71, 2-72, 2-76 and 3-22. As a result, the insect mortality rates for all of the compounds in the case of diluting to a concentration of 125 ppm were 90% or higher.

Test Example 5

Efficacy Test Against *Aculops pelekassi*

Twenty acaricide-resistant adult female *Aculops pelekassi acarus* were inoculated onto a mandarin orange leaf placed in a Petri dish. Next, an emulsion was prepared having the formula indicated in the aforementioned Preparation example 2. This emulsion was diluted with water to a compound concentration of 125 ppm after which the diluted liquids were sprayed onto the mandarin orange leaf with a rotary spraying tower. The mandarin orange leaf was then placed in a temperature-controlled room at a temperature of 25° C. and a humidity of 65%. The life and death of the adult insects were investigated 3 days after the spraying. The development from eggs laid to adult was investigated 10 days after the spraying.

The aforementioned test was carried out on the emulsions containing the Compound No. 1-3, 1-8, 1-9, 1-10, 1-13, 1-24, 1-25, 1-26, 1-27, 1-28, 1-29, 1-30, 1-41, 1-42, 1-50, 1-51, 1-55, 2-1, 2-2, 2-4, 2-6, 2-7, 2-8, 2-9, 2-10, 2-11, 2-13, 2-21, 2-24, and 2-33. As a result, the insect mortality rates for all of the compounds in the case of diluting to a concentration of 125 ppm were 90% or higher.

Test Example 6

Insecticidal Potency Test Against *Haemaphysalis longicornis*

0.118 ml of acetone solution having 400 ppm concentration of the compound of the present invention was added to a 20-mL glass vial. Air was supplied to the inside of the glass vial using a dryer, while rotating the glass vial, thereby volatilizing acetone to form a thin film on the inside wall of the glass vial. Since the surface area of the inside wall of the glass vial was 47 cm$^2$, the amount of the drug solution per surface area was 1 μg/cm$^2$.

Fifteen to forty larval *Haemaphysalis longicornis* ticks were placed in the glass vial, followed by closing the glass vial and placing it in a temperature-controlled room (25° C., dark).

The insect mortality rate was calculated after 1 day and 2 days.

Insect mortality rate (%)=(the number of dead ticks/ the number of released ticks)×100

The aforementioned test was carried out on the Compound No. 1-161, 2-1, 2-13, and 2-26. As a result, all of the compounds demonstrated 100% of insect mortality rate.

According to aforementioned results, the compound of the present invention demonstrates a superior pesticidal activity against *acarus*.

INDUSTRIAL APPLICABILITY

The aryloxyurea compound or a salt thereof according to the present invention can protect agricultural crops against infection by harmful organisms. In addition, it also has hygiene applications. Particularly, the compound of the present invention is able to effectively reduce *acarus* and/or plant pathogen infection.

The invention claimed is:

1. An aryloxyurea compound of formula (I) or a salt thereof:

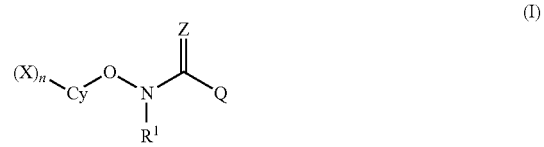

wherein in formula (I), Cy is a C6-10 aryl group;
X is an unsubstituted or substituted C1-6 alkyl group, unsubstituted or substituted C3-8 cycloalkyl group, unsubstituted or substituted C2-6 alkenyl group, unsubstituted or substituted C2-6 alkynyl group, hydroxy group, unsubstituted or substituted C1-6 alkoxy group, amino group, unsubstituted or substituted C1-6 alkyl amino group, unsubstituted or substituted C1-7 acyl group, unsubstituted or substituted C1-6 alkoxycarbonyl group, unsubstituted or substituted C1-6 alkyl sulfonyl group, unsubstituted or substituted C1-6 alkoxysulfonyl group, unsubstituted or substituted C6-10 aryl group, unsubstituted or substituted heteroaryl group, unsubstituted or substituted hydroxyimino C1-6 alkyl group, nitro group, cyano group, or halogen atom;
n is the number of X bonded to Cy and is an integer of 0 to 5; when n is 2 or more, X may be mutually the same or different, and when n is 2 or more, X may bond together to form a ring together with the carbon atoms or nitrogen atoms bonded thereto;
R$^1$ is an unsubstituted or substituted C1-6 alkyl group, unsubstituted or substituted C2-6 alkenyl group, or unsubstituted or substituted C2-6 alkynyl group, wherein R$^1$ is not an unsubstituted or substituted C1-7 acyl group;

Q is a group of formula (II):

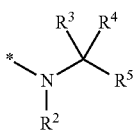

(II)

wherein in formula (II),
* is the bonding position;
$R^2$ is a hydrogen atom, unsubstituted or substituted C1-6 alkyl group, unsubstituted or substituted C2-6 alkenyl group, unsubstituted or substituted C2-6 alkynyl group, unsubstituted or substituted C1-7 acyl group, or unsubstituted or substituted C1-6 alkoxycarbonyl group, $R^1$ and $R^2$ may bond together to form an unsubstituted or substituted C2-4 alkylene group;
$R^3$ and $R^4$ each independently is an unsubstituted or substituted C1-6 alkyl group;
$R^5$ is an unsubstituted or substituted C6-10 aryl group, unsubstituted or substituted heteroaryl group, or unsubstituted or substituted aminocarbonyl group;
Z is an oxygen atom or sulfur atom.

2. A pest control agent, comprising at least one of the aryloxyurea compound or a salt thereof according to claim 1 as an active ingredient.

3. An acaricide, comprising at least one of the aryloxyurea compound or a salt thereof according to claim 1 as an active ingredient.

4. An aryloxyurea compound of formula (I) or a salt thereof:

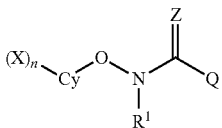

(I)

wherein in formula (I), Cy is a heteroaryl aryl group;
X is an unsubstituted or substituted C1-6 alkyl group, unsubstituted or substituted C3-8 cycloalkyl group, unsubstituted or substituted C2-6 alkenyl group, unsubstituted or substituted C2-6 alkynyl group, hydroxy group, unsubstituted or substituted C1-6 alkoxy group, amino group, unsubstituted or substituted C1-6 alkyl amino group, unsubstituted or substituted C1-7 acyl group, unsubstituted or substituted C1-6 alkoxycarbonyl group, unsubstituted or substituted C1-6 alkyl sulfonyl group, unsubstituted or substituted C1-6 alkoxysulfonyl group, unsubstituted or substituted C6-10 aryl group, unsubstituted or substituted heteroaryl group, unsubstituted or substituted hydroxyimino C1-6 alkyl group, nitro group, cyano group, or halogen atom;
n is the number of X bonded to Cy and is an integer of 0 to 5; when n is 2 or more, X may be mutually the same or different, and when n is 2 or more, X may bond together to form a ring together with the carbon atoms or nitrogen atoms bonded thereto;
$R^1$ is an unsubstituted or substituted C1-6 alkyl group, unsubstituted or substituted C2-6 alkenyl group, or unsubstituted or substituted C2-6 alkynyl group, wherein $R^1$ is not an unsubstituted or substituted C1-7 acyl group;
Q is a group of formula (II):

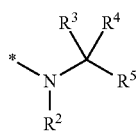

(II)

wherein in formula (II),
* is the bonding position;
$R^2$ is a hydrogen atom, unsubstituted or substituted C1-6 alkyl group, unsubstituted or substituted C2-6 alkenyl group, unsubstituted or substituted C2-6 alkynyl group, unsubstituted or substituted C1-7 acyl group, or unsubstituted or substituted C1-6 alkoxycarbonyl group, $R^1$ and $R^2$ may bond together to form an unsubstituted or substituted C2-4 alkylene group;
$R^3$ and $R^4$ each independently is an unsubstituted or substituted C1-6 alkyl group;
$R^5$ is an unsubstituted or substituted aminocarbonyl group;
Z is an oxygen atom or sulfur atom.

* * * * *